United States Patent
Forrest et al.

(10) Patent No.: US 12,364,403 B2
(45) Date of Patent: Jul. 22, 2025

(54) WEARABLE DEVICE FOR NONINVASIVE BODY TEMPERATURE MEASUREMENT

(71) Applicant: Masimo Corporation, Irvine, CA (US)

(72) Inventors: Kevin Forrest, Rancho Santa Margarita, CA (US); Ammar Al-Ali, San Juan Capistrano, CA (US); Valery G. Telfort, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/623,941

(22) Filed: Apr. 1, 2024

(65) Prior Publication Data

US 2024/0245309 A1  Jul. 25, 2024

Related U.S. Application Data

(62) Division of application No. 17/206,907, filed on Mar. 19, 2021, now Pat. No. 11,974,833.

(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0004* (2013.01); *A61B 5/0008* (2013.01);
(Continued)

(58) Field of Classification Search
CPC ....... A61B 5/0008; A61B 5/01; A61B 5/6801; A61B 5/02055; A61B 2562/0271; A61B 2562/166
See application file for complete search history.

(56) References Cited

U.S. PATENT DOCUMENTS

| | | |
|---|---|---|
| 3,646,606 A | 2/1972 | Buxton et al. |
| 3,690,313 A | 9/1972 | Weppner et al. |

(Continued)

FOREIGN PATENT DOCUMENTS

| | | |
|---|---|---|
| CN | 101401313 | 4/2009 |
| CN | 101534706 | 9/2009 |

(Continued)

OTHER PUBLICATIONS

US 8,845,543 B2, 09/2014, Diab et al. (withdrawn)

(Continued)

*Primary Examiner* — Tse W Chen
*Assistant Examiner* — Evelyn Grace Park
(74) *Attorney, Agent, or Firm* — Knobbe, Martens, Olson & Bear, LLP

(57) ABSTRACT

A wearable device for a noninvasive measurement of a user's body temperature can include a housing, a first substrate coupled to the housing and having an opening, a second substrate coupled to the first substrate and configured to secure to skin of a user, a mounting frame enclosed by the housing and the first substrate, a circuit board secured by the mounting frame, a temperature sensor coupled to the circuit board and configured to determine a body temperature of the user, and a thermally conductive probe. The thermally conductive probe is secured by the mounting frame and positioned proximate to the first temperature sensor. The thermally conductive probe extends at least partially through the opening in the first substrate and transmits a thermal energy from a portion of the user's skin to the first temperature sensor.

20 Claims, 18 Drawing Sheets

Related U.S. Application Data

(60) Provisional application No. 63/106,273, filed on Oct. 27, 2020, provisional application No. 63/065,961, filed on Aug. 14, 2020, provisional application No. 63/056,925, filed on Jul. 27, 2020, provisional application No. 63/049,478, filed on Jul. 8, 2020, provisional application No. 63/010,669, filed on Apr. 15, 2020, provisional application No. 62/992,808, filed on Mar. 20, 2020, provisional application No. 62/992,779, filed on Mar. 20, 2020.

(51) Int. Cl.

| | | |
|---|---|---|
| *A61B 5/01* | (2006.01) | |
| *A61B 5/024* | (2006.01) | |
| *A61B 5/026* | (2006.01) | |
| *A61B 5/08* | (2006.01) | |
| *A61B 5/145* | (2006.01) | |
| *A61B 5/1455* | (2006.01) | |
| *G06F 3/04842* | (2022.01) | |
| *G06F 9/451* | (2018.01) | |
| *G16H 10/60* | (2018.01) | |
| *G16H 15/00* | (2018.01) | |
| *G16H 40/20* | (2018.01) | |
| *G16H 40/67* | (2018.01) | |
| *G16H 50/20* | (2018.01) | |
| *G16H 50/30* | (2018.01) | |
| *G16H 50/70* | (2018.01) | |
| *G16H 50/80* | (2018.01) | |
| *H04B 17/318* | (2015.01) | |
| *H04W 4/021* | (2018.01) | |

(52) U.S. Cl.
CPC ............ *A61B 5/002* (2013.01); *A61B 5/0022* (2013.01); *A61B 5/01* (2013.01); *A61B 5/0205* (2013.01); *A61B 5/08* (2013.01); *A61B 5/0816* (2013.01); *A61B 5/14542* (2013.01); *A61B 5/6801* (2013.01); *A61B 5/6814* (2013.01); *A61B 5/6823* (2013.01); *A61B 5/6824* (2013.01); *A61B 5/6826* (2013.01); *A61B 5/7275* (2013.01); *A61B 5/7282* (2013.01); *A61B 5/7435* (2013.01); *A61B 5/746* (2013.01); *A61B 5/7465* (2013.01); *A61B 5/747* (2013.01); *A61B 5/7475* (2013.01); *G06F 9/451* (2018.02); *G16H 10/60* (2018.01); *G16H 15/00* (2018.01); *G16H 40/20* (2018.01); *G16H 40/67* (2018.01); *G16H 50/20* (2018.01); *G16H 50/30* (2018.01); *G16H 50/70* (2018.01); *G16H 50/80* (2018.01); *H04B 17/318* (2015.01); *H04W 4/021* (2013.01); *A61B 5/024* (2013.01); *A61B 5/026* (2013.01); *A61B 5/14551* (2013.01); *A61B 2562/0271* (2013.01); *G06F 3/04842* (2013.01)

(56) References Cited

U.S. PATENT DOCUMENTS

| | | | |
|---|---|---|---|
| 3,978,849 | A | 9/1976 | Geneen |
| 4,108,166 | A | 8/1978 | Schmid |
| 4,129,125 | A | 12/1978 | Lester et al. |
| 4,231,354 | A | 11/1980 | Kurtz et al. |
| D278,363 | S | 4/1985 | Schenkel et al. |
| 4,589,415 | A | 5/1986 | Haaga |
| 4,662,378 | A | 5/1987 | Thomis |
| D297,460 | S | 8/1988 | Inoue et al. |
| 4,838,275 | A | 6/1989 | Lee |
| 4,852,570 | A | 8/1989 | Levine |
| 4,960,128 | A | 10/1990 | Gordon et al. |
| 4,964,408 | A | 10/1990 | Hink et al. |
| 4,966,154 | A | 10/1990 | Cooper et al. |
| 5,092,340 | A | 3/1992 | Yamaguchi et al. |
| 5,140,519 | A | 8/1992 | Friesdorf et al. |
| 5,159,932 | A | 11/1992 | Zanetti et al. |
| 5,161,539 | A | 11/1992 | Evans et al. |
| 5,262,944 | A | 11/1993 | Weisner et al. |
| 5,277,189 | A | 1/1994 | Jacobs |
| 5,278,627 | A | 1/1994 | Aoyagi et al. |
| 5,282,474 | A | 2/1994 | Valdes Sosa et al. |
| 5,296,688 | A | 3/1994 | Hamilton et al. |
| 5,318,037 | A | 6/1994 | Evans et al. |
| 5,319,355 | A | 6/1994 | Russek |
| 5,331,549 | A | 7/1994 | Crawford, Jr. |
| 5,333,106 | A | 7/1994 | Lanpher et al. |
| 5,337,744 | A | 8/1994 | Branigan |
| 5,341,805 | A | 8/1994 | Stavridi et al. |
| 5,348,008 | A | 9/1994 | Bornn et al. |
| 5,358,519 | A | 10/1994 | Grandjean |
| 5,375,599 | A | 12/1994 | Shimizu |
| 5,377,676 | A | 1/1995 | Vari et al. |
| 5,400,794 | A | 3/1995 | Gorman |
| 5,416,695 | A | 5/1995 | Stutman et al. |
| D360,596 | S | 7/1995 | Moritz et al. |
| 5,431,170 | A | 7/1995 | Mathews |
| 5,434,611 | A | 7/1995 | Tamura |
| 5,436,499 | A | 7/1995 | Namavar et al. |
| 5,456,252 | A | 10/1995 | Vari et al. |
| 5,479,934 | A | 1/1996 | Imran |
| 5,482,036 | A | 1/1996 | Diab et al. |
| 5,483,968 | A | 1/1996 | Adam et al. |
| 5,494,041 | A | 2/1996 | Wilk |
| 5,494,043 | A | 2/1996 | O'Sullivan et al. |
| 5,503,149 | A | 4/1996 | Beavin |
| 5,505,202 | A | 4/1996 | Mogi et al. |
| 5,523,534 | A | 6/1996 | Meister et al. |
| 5,533,511 | A | 7/1996 | Kaspari et al. |
| D372,787 | S | 8/1996 | Dozier et al. |
| 5,544,649 | A | 8/1996 | David et al. |
| 5,553,609 | A | 9/1996 | Chen et al. |
| 5,558,638 | A | 9/1996 | Evers et al. |
| 5,566,676 | A | 10/1996 | Rosenfeldt et al. |
| 5,576,952 | A | 11/1996 | Stutman et al. |
| 5,579,001 | A | 11/1996 | Dempsey et al. |
| 5,590,649 | A | 1/1997 | Caro et al. |
| 5,602,924 | A | 2/1997 | Durand et al. |
| 5,619,991 | A | 4/1997 | Sloane |
| 5,638,816 | A | 6/1997 | Kiani-Azarbayjany et al. |
| 5,638,818 | A | 6/1997 | Diab et al. |
| 5,640,967 | A | 6/1997 | Fine et al. |
| 5,645,440 | A | 7/1997 | Tobler et al. |
| 5,671,914 | A | 9/1997 | Kalkhoran et al. |
| 5,685,314 | A | 11/1997 | Geheb et al. |
| 5,687,717 | A | 11/1997 | Halpern et al. |
| 5,694,020 | A | 12/1997 | Lang et al. |
| 5,724,580 | A | 3/1998 | Levin et al. |
| 5,724,983 | A | 3/1998 | Selker et al. |
| 5,725,308 | A | 3/1998 | Smith et al. |
| 5,726,440 | A | 3/1998 | Kalkhoran et al. |
| 5,732,146 | A | 3/1998 | Yamada et al. |
| 5,734,739 | A | 3/1998 | Sheehan et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,079 | A | 5/1998 | Ludwig et al. |
| 5,758,644 | A | 6/1998 | Diab et al. |
| 5,760,910 | A | 6/1998 | Lepper, Jr. et al. |
| 5,772,585 | A | 6/1998 | Lavin et al. |
| 5,782,805 | A | 7/1998 | Meinzer |
| 5,801,637 | A | 9/1998 | Lomholt |
| 5,813,403 | A | 9/1998 | Soller et al. |
| 5,822,544 | A | 10/1998 | Chaco et al. |
| 5,822,546 | A | 10/1998 | George |
| 5,855,550 | A | 1/1999 | Lai et al. |
| 5,890,929 | A | 4/1999 | Mills et al. |
| 5,910,139 | A | 6/1999 | Cochran et al. |
| 5,919,134 | A | 7/1999 | Diab |

(56) References Cited

U.S. PATENT DOCUMENTS

| | | |
|---|---|---|
| 5,921,920 A | 7/1999 | Marshall et al. |
| 5,924,074 A | 7/1999 | Evans |
| 5,931,160 A | 8/1999 | Gilmore et al. |
| 5,941,836 A | 8/1999 | Friedman |
| 5,942,986 A | 8/1999 | Shabot et al. |
| 5,950,189 A | 9/1999 | Cohen et al. |
| 5,987,343 A | 11/1999 | Kinast |
| 5,987,519 A | 11/1999 | Peifer et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,063 A | 2/2000 | Hoar et al. |
| 6,032,678 A | 3/2000 | Rottem |
| 6,035,230 A | 3/2000 | Kang et al. |
| 6,036,718 A | 3/2000 | Ledford et al. |
| 6,040,578 A | 3/2000 | Malin et al. |
| 6,066,204 A | 5/2000 | Haven |
| 6,093,146 A | 7/2000 | Filangeri |
| 6,101,478 A | 8/2000 | Brown |
| 6,106,463 A | 8/2000 | Wilk |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,129,686 A | 10/2000 | Friedman |
| 6,132,218 A | 10/2000 | Benja-Athon |
| 6,139,494 A | 10/2000 | Cairnes |
| 6,144,868 A | 11/2000 | Parker |
| 6,152,754 A | 11/2000 | Gerhardt et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,221,012 B1 | 4/2001 | Maschke et al. |
| 6,224,553 B1 | 5/2001 | Nevo |
| 6,230,142 B1 | 5/2001 | Benigno et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,267,723 B1 | 7/2001 | Matsumura et al. |
| 6,269,262 B1 | 7/2001 | Kandori et al. |
| 6,280,381 B1 | 8/2001 | Malin et al. |
| 6,285,896 B1 | 9/2001 | Tobler et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,354,235 B1 | 3/2002 | Davies |
| 6,360,114 B1 | 3/2002 | Diab et al. |
| 6,364,834 B1 | 4/2002 | Reuss et al. |
| 6,368,283 B1 | 4/2002 | Xu et al. |
| 6,385,476 B1 | 5/2002 | Osadchy et al. |
| 6,385,589 B1 | 5/2002 | Trusheim et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,487,429 B2 | 11/2002 | Hockersmith et al. |
| 6,505,059 B1 | 1/2003 | Kollias et al. |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,578,428 B1 | 6/2003 | Dromms et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,606,511 B1 | 8/2003 | Ali et al. |
| 6,616,606 B1 | 9/2003 | Peterson et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,646,556 B1 | 11/2003 | Smith et al. |
| 6,650,939 B2 | 11/2003 | Takpke et al. |
| D483,872 S | 12/2003 | Cruz et al. |
| 6,658,276 B2 | 12/2003 | Kianl et al. |
| 6,661,161 B1 | 12/2003 | Lanzo et al. |
| 6,694,180 B1 | 2/2004 | Boesen |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,719,694 B2 | 4/2004 | Weng et al. |
| 6,735,379 B2 | 5/2004 | Salmon et al. |
| 6,738,652 B2 | 5/2004 | Mattu et al. |
| 6,746,406 B2 | 6/2004 | Lia et al. |
| 6,751,492 B2 | 6/2004 | Ben-Haim |
| 6,760,607 B2 | 7/2004 | Al-Ali |
| 6,766,188 B2 | 7/2004 | Soller |
| 6,783,492 B2 | 8/2004 | Dominguez |
| 6,788,965 B2 | 9/2004 | Ruchti et al. |
| 6,790,178 B1 | 9/2004 | Mault et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,816,241 B2 | 11/2004 | Grubisic |
| 6,817,979 B2 | 11/2004 | Nihtila et al. |
| 6,822,564 B2 | 11/2004 | Al-Ali |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,855,112 B2 | 2/2005 | Kao et al. |
| 6,860,266 B2 | 3/2005 | Blike |
| 6,876,931 B2 | 4/2005 | Lorenz et al. |
| 6,897,788 B2 | 5/2005 | Khair et al. |
| 6,907,237 B1 | 6/2005 | Dorenbosch et al. |
| 6,915,149 B2 | 7/2005 | Ben-Haim |
| 6,920,345 B2 | 7/2005 | Al-Ali et al. |
| 6,934,570 B2 | 8/2005 | Kiani et al. |
| 6,943,348 B1 | 9/2005 | Coffin IV |
| D511,004 S | 10/2005 | Masuda |
| 6,952,340 B2 | 10/2005 | Son et al. |
| 6,956,649 B2 | 10/2005 | Acosta et al. |
| D511,384 S | 11/2005 | Masuda |
| 6,961,598 B2 | 11/2005 | Diab |
| 6,970,792 B1 | 11/2005 | Diab |
| 6,980,419 B2 | 12/2005 | Smith et al. |
| 6,983,179 B2 | 1/2006 | Ben-Haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,997,884 B2 | 2/2006 | Ulmsten |
| 6,998,247 B2 | 2/2006 | Monfre et al. |
| 7,003,338 B2 | 2/2006 | Weber et al. |

(56) References Cited

U.S. PATENT DOCUMENTS

| | | |
|---|---|---|
| 7,004,907 B2 | 2/2006 | Banet et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,033,761 B2 | 4/2006 | Shafer |
| 7,035,686 B2 | 4/2006 | Hogan |
| 7,063,666 B2 | 6/2006 | Weng et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,179,228 B2 | 2/2007 | Banet |
| 7,188,621 B2 | 3/2007 | DeVries et al. |
| 7,208,119 B1 | 4/2007 | Kurtock et al. |
| 7,225,006 B2 | 5/2007 | Al-Ali et al. |
| RE39,672 E | 6/2007 | Shehada et al. |
| 7,229,415 B2 | 6/2007 | Schwartz |
| 7,238,159 B2 | 7/2007 | Banet et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,248,172 B2 | 7/2007 | Clifford et al. |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,268,859 B2 | 9/2007 | Sage, Jr. et al. |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric et al. |
| 7,289,835 B2 | 10/2007 | Mansfield et al. |
| 7,292,883 B2 | 11/2007 | De Felice et al. |
| 7,307,543 B2 | 12/2007 | Rosenfeld |
| 7,313,423 B2 | 12/2007 | Griffin et al. |
| D558,882 S | 1/2008 | Brady |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,336,187 B2 | 2/2008 | Hubbard, Jr. et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,178 B2 | 4/2008 | Ziel et al. |
| 7,356,365 B2 | 4/2008 | Schurman |
| 7,361,155 B2 | 4/2008 | Sage, Jr. et al. |
| D569,280 S | 5/2008 | Chen |
| 7,371,981 B2 | 5/2008 | Abdul-Hafiz |
| 7,373,193 B2 | 5/2008 | Al-Ali et al. |
| 7,377,794 B2 | 5/2008 | Ali et al. |
| 7,378,975 B1 | 5/2008 | Smith et al. |
| 7,382,247 B2 | 6/2008 | Welch et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,396,330 B2 | 7/2008 | Banet et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,094 B2 | 12/2008 | Rosenfeld |
| 7,475,019 B2 | 1/2009 | Rosenfeld |
| 7,481,772 B2 | 1/2009 | Banet |
| 7,483,729 B2 | 1/2009 | Al-Ali et al. |
| 7,489,250 B2 | 2/2009 | Bock et al. |
| D587,657 S | 3/2009 | Al-Ali et al. |
| 7,497,828 B1 | 3/2009 | Wilk et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| D592,507 S | 5/2009 | Wachman et al. |
| 7,530,942 B1 | 5/2009 | Diab |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,577,475 B2 | 8/2009 | Consentino et al. |
| 7,588,558 B2 | 9/2009 | Sage, Jr. et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| D610,690 S | 2/2010 | Tokumoto et al. |
| 7,654,966 B2 | 2/2010 | Westinskow et al. |
| 7,658,716 B2 | 2/2010 | Banet et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| D617,463 S | 6/2010 | Tokumoto et al. |
| 7,729,733 B2 | 6/2010 | Al-Ali et al. |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,783,879 B2 | 8/2010 | Krummel et al. |
| 7,791,155 B2 | 9/2010 | Diab |
| 7,794,407 B2 | 9/2010 | Rothenberg |
| 7,803,120 B2 | 9/2010 | Banet et al. |
| 7,806,830 B2 | 10/2010 | Bernstein |
| 7,820,184 B2 | 10/2010 | Strizker et al. |
| RE41,912 E | 11/2010 | Parker |
| 7,831,450 B2 | 11/2010 | Schoenberg |
| 7,841,986 B2 | 11/2010 | He et al. |
| D629,524 S | 12/2010 | Zeller et al. |
| 7,848,935 B2 | 12/2010 | Gotlib |
| 7,858,322 B2 | 12/2010 | Tymianski et al. |
| 7,865,232 B1 | 1/2011 | Krishnaswamy et al. |
| 7,880,626 B2 | 2/2011 | Al-Ali et al. |
| 7,881,892 B2 | 2/2011 | Soyemi et al. |
| 7,890,156 B2 | 2/2011 | Ooi et al. |
| D634,017 S | 3/2011 | Tokumoto et al. |

(56) References Cited

U.S. PATENT DOCUMENTS

| | | |
|---|---|---|
| 7,899,518 B2 | 3/2011 | Trepagnier et al. |
| 7,904,133 B2 | 3/2011 | Gehman et al. |
| 7,909,772 B2 | 3/2011 | Popov et al. |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,987,069 B2 | 7/2011 | Rodgers et al. |
| 7,988,639 B2 | 8/2011 | Starks |
| 7,990,382 B2 | 8/2011 | Kiani |
| 7,991,463 B2 | 8/2011 | Kelleher et al. |
| 7,991,625 B2 | 8/2011 | Rosenfeld |
| 7,993,275 B2 | 8/2011 | Banet et al. |
| 8,008,088 B2 | 8/2011 | Bellott et al. |
| RE42,753 E | 9/2011 | Kiani-Azarbayjany et al. |
| 8,027,846 B2 | 9/2011 | Schoenberg |
| 8,028,701 B2 | 10/2011 | Al-Ali et al. |
| 8,033,996 B2 | 10/2011 | Behar |
| 8,036,736 B2 | 10/2011 | Snyder et al. |
| 8,038,625 B2 | 10/2011 | Afonso et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |
| 8,130,105 B2 | 3/2012 | Al-Ali et al. |
| D659,836 S | 5/2012 | Bensch et al. |
| 8,170,887 B2 | 5/2012 | Rosenfeld |
| 8,175,895 B2 | 5/2012 | Rosenfeld |
| 8,180,440 B2 | 5/2012 | McCombie et al. |
| 8,182,443 B1 | 5/2012 | Kiani |
| 8,190,223 B2 | 5/2012 | Al-Ali et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| D665,085 S | 8/2012 | Strother et al. |
| 8,235,907 B2 | 8/2012 | Wilk et al. |
| 8,239,010 B2 | 8/2012 | Banet et al. |
| 8,239,780 B2 | 8/2012 | Manetta et al. |
| 8,241,213 B2 | 8/2012 | Lynn et al. |
| 8,249,815 B2 | 8/2012 | Taylor |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,290,574 B2 | 10/2012 | Field et al. |
| 8,294,588 B2 | 10/2012 | Fisher et al. |
| 8,294,716 B2 | 10/2012 | Lord et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,687 B2 | 11/2012 | Cross et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,004 B2 | 11/2012 | Moon et al. |
| 8,321,150 B2 | 11/2012 | Taylor |
| RE43,860 E | 12/2012 | Parker |
| 8,326,649 B2 | 12/2012 | Rosenfeld |
| 8,346,330 B2 | 1/2013 | Lamego |
| 8,348,840 B2 | 1/2013 | Heit et al. |
| 8,353,842 B2 | 1/2013 | Al-Ali et al. |
| 8,355,766 B2 | 1/2013 | MacNeish, III et al. |
| 8,360,936 B2 | 1/2013 | Dibenedetto et al. |
| 8,364,250 B2 | 1/2013 | Moon et al. |
| 8,374,665 B2 | 2/2013 | Lamego |
| D679,018 S | 3/2013 | Fullerton et al. |
| 8,388,353 B2 | 3/2013 | Kiani |
| 8,401,602 B2 | 3/2013 | Kiani |
| 8,401,874 B2 | 3/2013 | Rosenfeld |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,428,967 B2 | 4/2013 | Olsen et al. |
| 8,430,317 B2 | 4/2013 | Ross |
| 8,430,817 B1 | 4/2013 | Al-Ali et al. |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| D684,071 S | 6/2013 | Greenwood et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,475,370 B2 | 7/2013 | McCombie et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| D692,145 S | 10/2013 | Al-Ali et al. |
| 8,545,417 B2 | 10/2013 | Banet et al. |
| 8,554,297 B2 | 10/2013 | Moon et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,161 B2 | 11/2013 | Banet et al. |
| 8,577,431 B2 | 11/2013 | Lamego et al. |
| 8,579,813 B2 | 11/2013 | Causey, III et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,600,777 B2 | 12/2013 | Schoenberg |
| 8,602,997 B2 | 12/2013 | Banet et al. |
| 8,614,630 B2 | 12/2013 | Narasimhan et al. |
| 8,620,678 B2 | 12/2013 | Gotlib |
| 8,622,922 B2 | 1/2014 | Banet et al. |
| 8,630,691 B2 | 1/2014 | Lamego et al. |
| 8,639,319 B2 | 1/2014 | Hugh et al. |
| D699,255 S | 2/2014 | Kim |
| 8,641,631 B2 | 2/2014 | Sierra et al. |
| 8,652,060 B2 | 2/2014 | Al-Ali |
| 8,663,106 B2 | 3/2014 | Stivoric et al. |
| 8,666,468 B1 | 3/2014 | Al-Ali |
| 8,670,811 B2 | 3/2014 | O'Reilly |
| 8,672,854 B2 | 3/2014 | McCombie et al. |
| RE44,823 E | 4/2014 | Parker |
| RE44,875 E | 4/2014 | Kiani et al. |
| D701,964 S | 4/2014 | Yoneta et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,716,629 B2 | 5/2014 | Klewer et al. |
| 8,723,677 B1 | 5/2014 | Kiani |
| 8,727,977 B2 | 5/2014 | Banet et al. |
| 8,738,118 B2 | 5/2014 | Moon et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,755,535 B2 | 6/2014 | Telfort et al. |
| 8,755,872 B1 | 6/2014 | Marinow |
| D709,846 S | 7/2014 | Oswaks |
| 8,764,671 B2 | 7/2014 | Kiani |
| 8,768,423 B2 | 7/2014 | Shakespeare et al. |

(56) References Cited

U.S. PATENT DOCUMENTS

| | | |
|---|---|---|
| 8,771,204 B2 | 7/2014 | Telfort et al. |
| 8,781,544 B2 | 7/2014 | Al-Ali et al. |
| 8,790,268 B2 | 7/2014 | Al-Ali |
| D711,905 S | 8/2014 | Morrison |
| 8,801,613 B2 | 8/2014 | Al-Ali et al. |
| 8,808,188 B2 | 8/2014 | Banet et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,873,035 B2 | 10/2014 | Yang et al. |
| 8,878,888 B2 | 11/2014 | Rosenfeld |
| 8,888,700 B2 | 11/2014 | Banet et al. |
| 8,897,847 B2 | 11/2014 | Al-Ali |
| 8,898,369 B1 | 11/2014 | Yang |
| D719,267 S | 12/2014 | Vaccarella et al. |
| 8,907,287 B2 | 12/2014 | Vanderpohl |
| 8,909,330 B2 | 12/2014 | McCombie et al. |
| 8,911,377 B2 | 12/2014 | Al-Ali |
| 8,956,293 B2 | 2/2015 | McCombie et al. |
| 8,956,294 B2 | 2/2015 | McCombie et al. |
| 8,974,115 B2 | 3/2015 | Segal et al. |
| 8,979,765 B2 | 3/2015 | Banet et al. |
| 8,989,831 B2 | 3/2015 | Al-Ali et al. |
| 8,998,809 B2 | 4/2015 | Kiani |
| 9,035,794 B2 | 5/2015 | Narasimhan et al. |
| 9,055,928 B2 | 6/2015 | McCombie et al. |
| 9,057,689 B2 | 6/2015 | Soller |
| 9,066,666 B2 | 6/2015 | Kiani |
| 9,066,680 B1 | 6/2015 | Al-Ali et al. |
| 9,095,291 B2 | 8/2015 | Soller |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,149,192 B2 | 10/2015 | Banet et al. |
| 9,153,112 B1 | 10/2015 | Kiani et al. |
| 9,161,700 B2 | 10/2015 | Banet et al. |
| D743,817 S | 11/2015 | Singh et al. |
| 9,173,593 B2 | 11/2015 | Banet et al. |
| 9,173,594 B2 | 11/2015 | Banet et al. |
| 9,183,738 B1 | 11/2015 | Allen, Sr. et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| D746,161 S | 12/2015 | Vardi |
| 9,204,816 B2 | 12/2015 | Aga et al. |
| 9,211,095 B1 | 12/2015 | Al-Ali |
| 9,214,196 B2 | 12/2015 | Aga et al. |
| 9,215,986 B2 | 12/2015 | Banet et al. |
| 9,218,454 B2 | 12/2015 | Kiani et al. |
| 9,245,668 B1 | 1/2016 | Vo et al. |
| 9,247,004 B2 | 1/2016 | Azimi |
| 9,267,572 B2 | 2/2016 | Barker et al. |
| 9,277,864 B2 | 3/2016 | Yang et al. |
| 9,277,880 B2 | 3/2016 | Poeze et al. |
| 9,299,036 B2 | 3/2016 | Ross et al. |
| 9,307,908 B2 | 4/2016 | Chan et al. |
| 9,307,915 B2 | 4/2016 | McCombie et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,339,209 B2 | 5/2016 | Banet et al. |
| 9,339,211 B2 | 5/2016 | Banet et al. |
| D759,828 S | 6/2016 | Riedle |
| 9,364,158 B2 | 6/2016 | Banet et al. |
| 9,378,450 B1 | 6/2016 | Mei et al. |
| 9,380,952 B2 | 7/2016 | Banet et al. |
| 9,392,945 B2 | 7/2016 | Al-Ali et al. |
| 9,408,542 B1 | 8/2016 | Kinast et al. |
| 9,408,573 B2 | 8/2016 | Welch et al. |
| D766,113 S | 9/2016 | Dohi et al. |
| 9,436,645 B2 | 9/2016 | Al-Ali et al. |
| 9,439,574 B2 | 9/2016 | McCombie et al. |
| 9,445,759 B2 | 9/2016 | Lamego et al. |
| 9,459,089 B2 | 10/2016 | Ganton et al. |
| 9,471,541 B1 | 10/2016 | Chan et al. |
| 9,474,474 B2 | 10/2016 | Lamego et al. |
| 9,480,435 B2 | 11/2016 | Olsen |
| 9,483,726 B2 | 11/2016 | Mei et al. |
| 9,486,138 B2 | 11/2016 | Simpson et al. |
| 9,492,092 B2 | 11/2016 | McCombie et al. |
| D773,529 S | 12/2016 | Cabrera |
| D775,148 S | 12/2016 | Anzures |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,545,227 B2 | 1/2017 | Selvaraj et al. |
| 9,560,996 B2 | 2/2017 | Kiani |
| 9,563,836 B2 | 2/2017 | Mei et al. |
| 9,566,007 B2 | 2/2017 | McCombie et al. |
| 9,579,039 B2 | 2/2017 | Jansen et al. |
| D781,314 S | 3/2017 | Aström |
| 9,588,135 B1 | 3/2017 | Narasimhan et al. |
| 9,593,985 B2 | 3/2017 | Segal et al. |
| 9,622,692 B2 | 4/2017 | Lamego et al. |
| 9,632,533 B2 | 4/2017 | Li et al. |
| 9,632,981 B2 | 4/2017 | Chan et al. |
| D788,312 S | 5/2017 | Al-Ali et al. |
| 9,636,029 B1 | 5/2017 | Narasimhan et al. |
| 9,649,054 B2 | 5/2017 | Lamego et al. |
| 9,655,546 B2 | 5/2017 | Shen et al. |
| 9,655,559 B2 | 5/2017 | Chan et al. |
| D789,391 S | 6/2017 | Cabrera |
| D789,809 S | 6/2017 | Kang |
| 9,681,205 B1 | 6/2017 | Yang |
| 9,697,928 B2 | 7/2017 | Al-Ali et al. |
| D795,100 S | 8/2017 | Alla |
| D795,252 S | 8/2017 | Chung et al. |
| D795,713 S | 8/2017 | Griffin et al. |
| D795,714 S | 8/2017 | Pugmire et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,728,061 B2 | 8/2017 | Shen et al. |
| 9,749,232 B2 | 8/2017 | Sampath et al. |
| D796,350 S | 9/2017 | Bone |
| D796,363 S | 9/2017 | Ross et al. |
| 9,750,442 B2 | 9/2017 | Olsen |
| 9,750,461 B1 | 9/2017 | Telfort |
| 9,762,581 B1 | 9/2017 | Wang et al. |
| 9,762,673 B2 | 9/2017 | Azimi |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,788,778 B2 | 10/2017 | Chan et al. |
| 9,808,188 B1 | 11/2017 | Perea et al. |
| 9,814,405 B2 | 11/2017 | Yang et al. |
| 9,818,281 B2 | 11/2017 | Narasimhan |
| D805,926 S | 12/2017 | Im et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,855,003 B2 | 1/2018 | Chan et al. |
| 9,861,289 B2 | 1/2018 | Li et al. |
| 9,861,298 B2 | 1/2018 | Eckerbom et al. |
| 9,861,305 B1 | 1/2018 | Weber et al. |
| 9,870,533 B2 | 1/2018 | Ross |
| 9,872,619 B2 | 1/2018 | Lee |
| 9,872,634 B2 | 1/2018 | Chan et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,382 B2 | 4/2018 | Yang et al. |

(56) References Cited

U.S. PATENT DOCUMENTS

| | | |
|---|---|---|
| 9,936,917 B2 | 4/2018 | Poeze et al. |
| D817,784 S | 5/2018 | Swenson et al. |
| 9,955,937 B2 | 5/2018 | Telfort |
| 9,965,946 B2 | 5/2018 | Al-Ali et al. |
| 9,980,678 B2 | 5/2018 | Chan et al. |
| D819,660 S | 6/2018 | Cabrera |
| D820,311 S | 6/2018 | Cabrera |
| D820,865 S | 6/2018 | Muhsin et al. |
| D821,593 S | 6/2018 | Perez |
| 9,986,951 B1 | 6/2018 | Ferdosi et al. |
| 9,986,952 B2 | 6/2018 | Dalvi et al. |
| 9,993,203 B2 | 6/2018 | Mei et al. |
| 9,999,376 B2 | 6/2018 | Chan et al. |
| D822,215 S | 7/2018 | Al-Ali et al. |
| D822,216 S | 7/2018 | Barker et al. |
| 10,010,276 B2 | 7/2018 | Al-Ali et al. |
| 10,020,075 B2 | 7/2018 | Perlman et al. |
| 10,039,463 B1 | 8/2018 | Selvaraj et al. |
| 10,080,524 B1 | 9/2018 | Xi |
| 10,086,138 B1 | 10/2018 | Novak, Jr. |
| 10,111,591 B2 | 10/2018 | Dyell et al. |
| D833,305 S | 11/2018 | Jang et al. |
| D833,624 S | 11/2018 | DeJong et al. |
| 10,123,716 B2 | 11/2018 | Narasimhan et al. |
| 10,123,729 B2 | 11/2018 | Dyell et al. |
| 10,140,837 B2 | 11/2018 | Shen et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,143,383 B2 | 12/2018 | Tseng et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| D838,372 S | 1/2019 | Goering et al. |
| 10,182,750 B1 | 1/2019 | Philippine et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,834 B2 | 2/2019 | Selvaraj et al. |
| 10,205,291 B2 | 2/2019 | Scruggs et al. |
| 10,212,165 B1 | 2/2019 | Petersen et al. |
| 10,213,146 B2 | 2/2019 | Aga et al. |
| 10,213,163 B2 | 2/2019 | Ferdosi et al. |
| D842,136 S | 3/2019 | Jang et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D844,642 S | 4/2019 | Cabrera |
| D846,746 S | 4/2019 | Lee |
| D847,159 S | 4/2019 | Cabrera |
| 10,262,506 B2 | 4/2019 | Aga et al. |
| 10,279,247 B2 | 5/2019 | Kiani |
| 10,292,664 B2 | 5/2019 | Al-Ali |
| 10,299,720 B2 | 5/2019 | Brown et al. |
| 10,317,427 B2 | 6/2019 | Chan et al. |
| 10,321,872 B2 | 6/2019 | Li |
| 10,324,109 B2 | 6/2019 | Chan et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,357,163 B1 | 7/2019 | Selvaraj et al. |
| 10,362,002 B2 | 7/2019 | Ross et al. |
| 10,373,714 B1 | 8/2019 | Selvaraj et al. |
| 10,383,520 B2 | 8/2019 | Wojitczuk et al. |
| 10,383,527 B2 | 8/2019 | Al-Ali |
| 10,383,562 B2 | 8/2019 | Chan et al. |
| 10,388,120 B2 | 8/2019 | Muhsin et al. |
| 10,420,473 B2 | 9/2019 | Shi |
| 10,422,814 B2 | 9/2019 | Chan et al. |
| D861,508 S | 10/2019 | Ejiri et al. |
| D864,120 S | 10/2019 | Forrest et al. |
| 10,433,781 B2 | 10/2019 | Chan et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,849 B2 | 10/2019 | Ferdosi et al. |
| 10,448,871 B2 | 10/2019 | Al-Ali |
| 10,456,038 B2 | 10/2019 | Lamego et al. |
| D867,906 S | 11/2019 | Chang |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,506,953 B2 | 12/2019 | Ross et al. |
| D873,294 S | 1/2020 | Anzures |
| 10,524,726 B2 | 1/2020 | Wang et al. |
| 10,524,738 B2 | 1/2020 | Olsen |
| 10,532,174 B2 | 1/2020 | Al-Ali |
| 10,537,285 B2 | 1/2020 | Sherim et al. |
| 10,542,903 B2 | 1/2020 | Al-Ali et al. |
| 10,554,756 B2 | 2/2020 | Azimi |
| 10,555,678 B2 | 2/2020 | Dalvi et al. |
| 10,568,553 B2 | 2/2020 | O'Neil et al. |
| RE47,882 E | 3/2020 | Al-Ali |
| 10,582,854 B2 | 3/2020 | Liou et al. |
| 10,582,862 B1 | 3/2020 | Selvaraj et al. |
| 10,588,565 B2 | 3/2020 | Larson et al. |
| 10,595,776 B1 | 3/2020 | Selvaraj et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,325 B2 | 4/2020 | Chan et al. |
| 10,617,335 B2 | 4/2020 | Al-Ali et al. |
| 10,631,732 B2 | 4/2020 | Larson et al. |
| 10,637,181 B2 | 4/2020 | Al-Ali et al. |
| D883,819 S | 5/2020 | Singh et al. |
| D884,165 S | 5/2020 | deBock |
| D886,303 S | 6/2020 | Huang et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| D888,731 S | 6/2020 | Momchilov |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,739,205 B2 | 8/2020 | Jang et al. |
| 10,743,091 B1 | 8/2020 | Wang et al. |
| 10,750,951 B1 | 8/2020 | Prachar |
| 10,750,984 B2 | 8/2020 | Pauley et al. |
| D896,825 S | 9/2020 | Abel |
| D897,098 S | 9/2020 | Al-Ali |
| 10,758,164 B2 | 9/2020 | Derkx et al. |
| 10,772,522 B2 | 9/2020 | Zadig |
| 10,779,098 B2 | 9/2020 | Iswanto et al. |
| D898,924 S | 10/2020 | Hinds et al. |
| D901,538 S | 11/2020 | Cabrera |
| 10,827,958 B2 | 11/2020 | Biederman et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,741 B2 | 12/2020 | Damania et al. |
| 10,856,750 B2 | 12/2020 | Indorf |
| D906,970 S | 1/2021 | Forrest et al. |
| D907,219 S | 1/2021 | Neri |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| D920,138 S | 5/2021 | Kuwashiro et al. |

(56) References Cited

U.S. PATENT DOCUMENTS

| | | |
|---|---|---|
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| 11,064,948 B2 | 7/2021 | Peabody |
| D927,533 S | 8/2021 | Clymer |
| D927,699 S | 8/2021 | Al-Ali et al. |
| 11,076,777 B2 | 8/2021 | Lee et al. |
| 11,083,371 B1 | 8/2021 | Szabados et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| D933,508 S | 10/2021 | Wolff |
| 11,145,408 B2 | 10/2021 | Sampath et al. |
| 11,147,518 B1 | 10/2021 | Al-Ali et al. |
| 11,172,909 B2 | 11/2021 | Chan et al. |
| 11,185,262 B2 | 11/2021 | Al-Ali et al. |
| 11,191,484 B2 | 12/2021 | Kiani et al. |
| 11,234,623 B2 | 2/2022 | Frick |
| 11,253,190 B2 | 2/2022 | Ortiz et al. |
| D946,425 S | 3/2022 | Chang et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,492 S | 5/2022 | Wang et al. |
| D950,580 S | 5/2022 | Ahmed |
| D950,599 S | 5/2022 | Ahmed |
| D950,738 S | 5/2022 | Al-Ali et al. |
| D956,785 S | 7/2022 | Liu |
| D957,648 S | 7/2022 | Al-Ali |
| 11,382,567 B2 | 7/2022 | O'Brien et al. |
| 11,389,093 B2 | 7/2022 | Triman et al. |
| D960,913 S | 8/2022 | Kiikkala |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D966,914 S | 10/2022 | Avellera |
| D967,433 S | 10/2022 | Al-Ali et al. |
| 11,457,810 B2 | 10/2022 | Van Tassel et al. |
| 11,464,410 B2 | 10/2022 | Muhsin |
| 11,484,265 B2 | 11/2022 | Wang et al. |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| 11,517,229 B2 | 12/2022 | Huang et al. |
| 11,534,086 B2 | 12/2022 | Garai et al. |
| D974,193 S | 1/2023 | Forrest et al. |
| D978,884 S | 2/2023 | Cabrera |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,198 B2 | 10/2023 | Weiler |
| 11,803,623 B2 | 10/2023 | Kiani et al. |
| 11,832,940 B2 | 12/2023 | Diab et al. |
| D1,010,816 S | 1/2024 | Cook |
| D1,011,730 S | 1/2024 | Jagroop |
| D1,013,179 S | 1/2024 | Al-Ali et al. |
| 11,872,156 B2 | 1/2024 | Telfort et al. |
| 11,872,369 B1 | 1/2024 | Schiff |
| 11,879,960 B2 | 1/2024 | Ranasinghe et al. |
| 11,883,129 B2 | 1/2024 | Olsen |
| D1,019,674 S | 3/2024 | Yang |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,034,546 S | 7/2024 | Lange |
| D1,034,655 S | 7/2024 | Chen |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,040,852 S | 9/2024 | Bache |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| 2001/0011355 A1 | 8/2001 | Kawai |
| 2001/0034477 A1 | 10/2001 | Mansfield et al. |
| 2001/0039483 A1 | 11/2001 | Brand et al. |
| 2001/0046366 A1 | 11/2001 | Susskind |
| 2002/0010401 A1 | 1/2002 | Bushmakin et al. |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0133080 A1 | 9/2002 | Apruzzese et al. |
| 2002/0177758 A1 | 11/2002 | Schoenberg |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |

(56) References Cited

U.S. PATENT DOCUMENTS

| | | |
|---|---|---|
| 2003/0156288 A1 | 8/2003 | Barnum et al. |
| 2003/0158466 A1 | 8/2003 | Lynn et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0015103 A1 | 1/2004 | Aminian et al. |
| 2004/0064072 A1 | 4/2004 | Shapira |
| 2004/0090742 A1 | 5/2004 | Son et al. |
| 2004/0106163 A1 | 6/2004 | Workman, Jr. et al. |
| 2004/0122787 A1 | 6/2004 | Avinash et al. |
| 2004/0126007 A1 | 7/2004 | Ziel et al. |
| 2004/0147818 A1 | 7/2004 | Levy et al. |
| 2004/0179332 A1 | 9/2004 | Smith et al. |
| 2004/0186357 A1 | 9/2004 | Soderberg et al. |
| 2004/0230179 A1 | 11/2004 | Shehada et al. |
| 2004/0243017 A1 | 12/2004 | Causevic |
| 2004/0254431 A1 | 12/2004 | Shehada et al. |
| 2004/0254432 A1 | 12/2004 | Shehada et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0234317 A1 | 10/2005 | Kiani |
| 2005/0242946 A1 | 11/2005 | Hubbard, Jr. et al. |
| 2005/0245831 A1 | 11/2005 | Banet |
| 2005/0245839 A1 | 11/2005 | Stivoric et al. |
| 2005/0261594 A1 | 11/2005 | Banet |
| 2005/0261598 A1 | 11/2005 | Banet et al. |
| 2005/0268401 A1 | 12/2005 | Dixon et al. |
| 2005/0277872 A1 | 12/2005 | Colby, Jr. et al. |
| 2006/0009697 A1 | 1/2006 | Banet et al. |
| 2006/0009698 A1 | 1/2006 | Banet et al. |
| 2006/0049936 A1 | 3/2006 | Collins, Jr. et al. |
| 2006/0056487 A1 | 3/2006 | Kuroda et al. |
| 2006/0058647 A1 | 3/2006 | Strommer et al. |
| 2006/0064037 A1 | 3/2006 | Shalon et al. |
| 2006/0073719 A1 | 4/2006 | Kiani |
| 2006/0084878 A1 | 4/2006 | Banet et al. |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2006/0279426 A1 | 12/2006 | Bonnet et al. |
| 2006/0282021 A1 | 12/2006 | DeVaul et al. |
| 2006/0286861 A1 | 12/2006 | Avevor et al. |
| 2007/0000490 A1 | 1/2007 | DeVries et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0032748 A1 | 2/2007 | McNeil et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0132597 A1 | 6/2007 | Rodgers |
| 2007/0140475 A1 | 6/2007 | Kurtock et al. |
| 2007/0142715 A1 | 6/2007 | Banet et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185393 A1 | 8/2007 | Zhou et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0250286 A1 | 10/2007 | Duncan et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg et al. |
| 2007/0276261 A1 | 11/2007 | Banet et al. |
| 2007/0276262 A1 | 11/2007 | Banet et al. |
| 2007/0276632 A1 | 11/2007 | Banet et al. |
| 2007/0288263 A1 | 12/2007 | Rodgers |
| 2008/0000479 A1 | 1/2008 | Elaz et al. |
| 2008/0003200 A1 | 1/2008 | Arap et al. |
| 2008/0021731 A1 | 1/2008 | Rodgers |
| 2008/0021854 A1 | 1/2008 | Jung et al. |
| 2008/0033661 A1 | 2/2008 | Syroid et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0058657 A1 | 3/2008 | Schwartz et al. |
| 2008/0064965 A1 | 3/2008 | Jay et al. |
| 2008/0077026 A1 | 3/2008 | Banet et al. |
| 2008/0082004 A1 | 4/2008 | Banet et al. |
| 2008/0082145 A1 | 4/2008 | Skwarek |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0103375 A1 | 5/2008 | Kiani |
| 2008/0114220 A1 | 5/2008 | Banet et al. |
| 2008/0119412 A1 | 5/2008 | Tymianski et al. |
| 2008/0129518 A1 | 6/2008 | Carlton-Foss |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0214949 A1 | 9/2008 | Stivoric et al. |
| 2008/0221396 A1 | 9/2008 | Garces et al. |
| 2008/0221399 A1 | 9/2008 | Zhou et al. |
| 2008/0221418 A1 | 9/2008 | Al-Ali et al. |
| 2008/0221461 A1 | 9/2008 | Zhou et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0312542 A1 | 12/2008 | Banet et al. |
| 2008/0319275 A1 | 12/2008 | Chiu et al. |
| 2008/0319282 A1 | 12/2008 | Tran |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018409 A1 | 1/2009 | Banet et al. |
| 2009/0018422 A1 | 1/2009 | Banet et al. |
| 2009/0018453 A1 | 1/2009 | Banet et al. |
| 2009/0018808 A1 | 1/2009 | Bronstein et al. |

(56) References Cited

U.S. PATENT DOCUMENTS

| | | |
|---|---|---|
| 2009/0024008 A1 | 1/2009 | Brunner et al. |
| 2009/0036759 A1 | 2/2009 | Ault et al. |
| 2009/0044334 A1 | 2/2009 | Parsell et al. |
| 2009/0052623 A1 | 2/2009 | Tome et al. |
| 2009/0054735 A1 | 2/2009 | Higgins et al. |
| 2009/0054743 A1 | 2/2009 | Wekell et al. |
| 2009/0062682 A1 | 3/2009 | Bland et al. |
| 2009/0069642 A1 | 3/2009 | Gao et al. |
| 2009/0069868 A1 | 3/2009 | Bengtsson et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0112072 A1 | 4/2009 | Banet et al. |
| 2009/0118628 A1 | 5/2009 | Zhou et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0221937 A1 | 9/2009 | Smith |
| 2009/0226372 A1 | 9/2009 | Ruoslahti et al. |
| 2009/0247984 A1 | 10/2009 | Lamego et al. |
| 2009/0254003 A1 | 10/2009 | Buckman |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0309755 A1 | 12/2009 | Williamson |
| 2009/0322540 A1 | 12/2009 | Richardson et al. |
| 2010/0004518 A1 | 1/2010 | Vo et al. |
| 2010/0010385 A1 | 1/2010 | Skelton et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0063365 A1 | 3/2010 | Pisani et al. |
| 2010/0099964 A1 | 4/2010 | O'Reilly et al. |
| 2010/0113894 A1 | 5/2010 | Padiy |
| 2010/0121217 A1 | 5/2010 | Padiy et al. |
| 2010/0121226 A1 | 5/2010 | Ten Kate et al. |
| 2010/0125217 A1 | 5/2010 | Kuo et al. |
| 2010/0130875 A1 | 5/2010 | Banet et al. |
| 2010/0144627 A1 | 6/2010 | Vitek et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0261982 A1 | 10/2010 | Noury et al. |
| 2010/0270257 A1 | 10/2010 | Wachman et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317951 A1 | 12/2010 | Rutkowski et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0046498 A1 | 2/2011 | Klap et al. |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105956 A1 | 5/2011 | Hirth |
| 2011/0110560 A1 | 5/2011 | Adhikari |
| 2011/0118561 A1 | 5/2011 | Tari et al. |
| 2011/0118573 A1 | 5/2011 | Mckenna |
| 2011/0137297 A1 | 6/2011 | Kiani et al. |
| 2011/0152629 A1 | 6/2011 | Eaton et al. |
| 2011/0172498 A1 | 7/2011 | Olsen et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0201972 A1 | 8/2011 | Ten Kate |
| 2011/0208073 A1 | 8/2011 | Matsukawa et al. |
| 2011/0212090 A1 | 9/2011 | Pedersen et al. |
| 2011/0213225 A1 | 9/2011 | Bernstein et al. |
| 2011/0214501 A1 | 9/2011 | Ross et al. |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0227739 A1 | 9/2011 | Gilham et al. |
| 2011/0230733 A1 | 9/2011 | Al-Ali |
| 2011/0230791 A1 | 9/2011 | Ten Kate et al. |
| 2011/0257489 A1 | 10/2011 | Banet et al. |
| 2011/0257544 A1 | 10/2011 | Kaasinen et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0263950 A1 | 10/2011 | Larson et al. |
| 2011/0264035 A1 | 10/2011 | Yodfat et al. |
| 2011/0288421 A1 | 11/2011 | Banet et al. |
| 2011/0295094 A1 | 12/2011 | Doyle et al. |
| 2012/0001751 A1 | 1/2012 | Baker et al. |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0059230 A1 | 3/2012 | Teller et al. |
| 2012/0059283 A1 | 3/2012 | Gravem et al. |
| 2012/0071771 A1 | 3/2012 | Behar |
| 2012/0075464 A1 | 3/2012 | Derenne et al. |
| 2012/0088999 A1 | 4/2012 | Bishay et al. |
| 2012/0095352 A1 | 4/2012 | Tran |
| 2012/0095778 A1 | 4/2012 | Gross et al. |
| 2012/0101353 A1 | 4/2012 | Reggiardo et al. |
| 2012/0101411 A1 | 4/2012 | Hausdorff et al. |
| 2012/0101770 A1 | 4/2012 | Grabiner et al. |
| 2012/0108983 A1 | 5/2012 | Banet et al. |
| 2012/0117209 A1 | 5/2012 | Sinha |

(56) References Cited

U.S. PATENT DOCUMENTS

| | | |
|---|---|---|
| 2012/0123231 A1 | 5/2012 | O'Reilly |
| 2012/0123799 A1 | 5/2012 | Nolen et al. |
| 2012/0136221 A1 | 5/2012 | Killen et al. |
| 2012/0165629 A1 | 6/2012 | Merritt et al. |
| 2012/0179011 A1 | 7/2012 | Moon et al. |
| 2012/0184120 A1 | 7/2012 | Basta et al. |
| 2012/0190949 A1 | 7/2012 | McCombie et al. |
| 2012/0197619 A1 | 8/2012 | Namer Yelin et al. |
| 2012/0203078 A1 | 8/2012 | Sze et al. |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0239434 A1 | 9/2012 | Breslow et al. |
| 2012/0242501 A1 | 9/2012 | Tran et al. |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0294801 A1 | 11/2012 | Scherz et al. |
| 2012/0314901 A1 | 12/2012 | Hanson |
| 2012/0315867 A1 | 12/2012 | Davis et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0046197 A1 | 2/2013 | Dlugos, Jr. et al. |
| 2013/0052620 A1 | 2/2013 | Franklin et al. |
| 2013/0054180 A1 | 2/2013 | Barfield |
| 2013/0060147 A1 | 3/2013 | Welch et al. |
| 2013/0096405 A1 | 4/2013 | Garfio |
| 2013/0099936 A1 | 4/2013 | Azimi |
| 2013/0099937 A1 | 4/2013 | Azimi |
| 2013/0109929 A1 | 5/2013 | Menzel |
| 2013/0109937 A1 | 5/2013 | Banet et al. |
| 2013/0116515 A1 | 5/2013 | Banet et al. |
| 2013/0120147 A1 | 5/2013 | Narasimhan et al. |
| 2013/0120152 A1 | 5/2013 | Narasimhan et al. |
| 2013/0122849 A1 | 5/2013 | Doezema |
| 2013/0130622 A1 | 5/2013 | Yang et al. |
| 2013/0138395 A1 | 5/2013 | Baggen et al. |
| 2013/0155889 A1 | 6/2013 | Brownworth et al. |
| 2013/0214850 A1 | 8/2013 | Aga et al. |
| 2013/0245487 A1 | 9/2013 | Aga et al. |
| 2013/0261494 A1 | 10/2013 | Bloom et al. |
| 2013/0281875 A1 | 10/2013 | Narasimhan et al. |
| 2013/0296672 A1 | 11/2013 | O'Neil et al. |
| 2013/0317333 A1 | 11/2013 | Yun et al. |
| 2013/0317393 A1 | 11/2013 | Weiss et al. |
| 2013/0340176 A1 | 12/2013 | Stevens et al. |
| 2013/0342691 A1 | 12/2013 | Lewis et al. |
| 2013/0345921 A1 | 12/2013 | Al-Ali et al. |
| 2014/0005502 A1 | 1/2014 | Klap et al. |
| 2014/0015687 A1 | 1/2014 | Narasimhan et al. |
| 2014/0019080 A1 | 1/2014 | Chan et al. |
| 2014/0022081 A1 | 1/2014 | Ribble et al. |
| 2014/0025010 A1 | 1/2014 | Stroup et al. |
| 2014/0046674 A1 | 2/2014 | Rosenfeld |
| 2014/0051946 A1 | 2/2014 | Arne |
| 2014/0066795 A1 | 3/2014 | Ferdosi et al. |
| 2014/0073982 A1 | 3/2014 | Yang et al. |
| 2014/0081099 A1 | 3/2014 | Banet et al. |
| 2014/0088385 A1 | 3/2014 | Moon et al. |
| 2014/0121543 A1 | 5/2014 | Chan et al. |
| 2014/0128778 A1 | 5/2014 | Chan et al. |
| 2014/0129178 A1 | 5/2014 | Meduna et al. |
| 2014/0142445 A1 | 5/2014 | Banet et al. |
| 2014/0152673 A1 | 6/2014 | Lynn et al. |
| 2014/0163393 A1 | 6/2014 | McCombie et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0200415 A1 | 7/2014 | McCombie et al. |
| 2014/0200474 A1 | 7/2014 | Selvaraj et al. |
| 2014/0228692 A1 | 8/2014 | Chan et al. |
| 2014/0235964 A1 | 8/2014 | Banet et al. |
| 2014/0249431 A1 | 9/2014 | Banet et al. |
| 2014/0249432 A1 | 9/2014 | Banet et al. |
| 2014/0249433 A1 | 9/2014 | Banet et al. |
| 2014/0249434 A1 | 9/2014 | Banet et al. |
| 2014/0249435 A1 | 9/2014 | Banet et al. |
| 2014/0249440 A1 | 9/2014 | Banet et al. |
| 2014/0249441 A1 | 9/2014 | Banet et al. |
| 2014/0249442 A1 | 9/2014 | Banet et al. |
| 2014/0257056 A1 | 9/2014 | Moon et al. |
| 2014/0257057 A1 | 9/2014 | Reis Cunha et al. |
| 2014/0257850 A1 | 9/2014 | Walker et al. |
| 2014/0266690 A1 | 9/2014 | McKinley |
| 2014/0266787 A1 | 9/2014 | Tran |
| 2014/0275845 A1 | 9/2014 | Eagon et al. |
| 2014/0275871 A1 | 9/2014 | Lamego et al. |
| 2014/0275872 A1 | 9/2014 | Merritt et al. |
| 2014/0275888 A1 | 9/2014 | Wegerich et al. |
| 2014/0275932 A1 | 9/2014 | Zadig |
| 2014/0276127 A1 | 9/2014 | Ferdosi et al. |
| 2014/0276145 A1 | 9/2014 | Banet et al. |
| 2014/0276175 A1 | 9/2014 | Banet et al. |
| 2014/0276238 A1 | 9/2014 | Osorio |
| 2014/0288947 A1 | 9/2014 | Simpson et al. |
| 2014/0301893 A1 | 10/2014 | Stroup et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0343889 A1 | 11/2014 | Ben Shalom et al. |
| 2014/0375428 A1 | 12/2014 | Park |
| 2015/0005600 A1 | 1/2015 | Blank et al. |
| 2015/0011907 A1 | 1/2015 | Purdon et al. |
| 2015/0020571 A1 | 1/2015 | Chan et al. |
| 2015/0045628 A1 | 2/2015 | Moghadam et al. |
| 2015/0055681 A1 | 2/2015 | Tsuchida |
| 2015/0057562 A1 | 2/2015 | Linders et al. |
| 2015/0073241 A1 | 3/2015 | Lamego |
| 2015/0080754 A1 | 3/2015 | Purdon et al. |
| 2015/0087923 A1 | 3/2015 | Bardy et al. |
| 2015/0094559 A1 | 4/2015 | Russell |
| 2015/0094618 A1 | 4/2015 | Russell et al. |
| 2015/0099950 A1 | 4/2015 | Al-Ali et al. |
| 2015/0106121 A1 | 4/2015 | Muhsin et al. |
| 2015/0109442 A1 | 4/2015 | Derenne et al. |
| 2015/0112264 A1 | 4/2015 | Kamen et al. |
| 2015/0126822 A1 | 5/2015 | Chavan et al. |
| 2015/0126882 A1 | 5/2015 | Chavan et al. |
| 2015/0130613 A1 | 5/2015 | Fullam |
| 2015/0164410 A1 | 6/2015 | Selvaraj et al. |
| 2015/0164411 A1 | 6/2015 | Selvaraj et al. |
| 2015/0164417 A1 | 6/2015 | Tupin, Jr. |
| 2015/0164437 A1 | 6/2015 | McCombie et al. |
| 2015/0173654 A1 | 6/2015 | Bélanger et al. |
| 2015/0190086 A1 | 7/2015 | Chan et al. |
| 2015/0219542 A1 | 8/2015 | Kent |
| 2015/0221202 A1 | 8/2015 | Russell et al. |
| 2015/0254956 A1 | 9/2015 | Shen et al. |
| 2015/0272481 A1 | 10/2015 | Glaser et al. |
| 2015/0282717 A1 | 10/2015 | McCombie et al. |
| 2015/0320339 A1 | 11/2015 | Larson et al. |
| 2016/0004952 A1 | 1/2016 | Mei |
| 2016/0022224 A1 | 1/2016 | Banet et al. |
| 2016/0038061 A1 | 2/2016 | Kechichian et al. |
| 2016/0045163 A1 | 2/2016 | Weisner et al. |
| 2016/0095549 A1 | 4/2016 | Chang |
| 2016/0100776 A1 | 4/2016 | Najafi |
| 2016/0119210 A1 | 4/2016 | Koehler |
| 2016/0143546 A1 | 5/2016 | McCombie et al. |
| 2016/0183794 A1 | 6/2016 | Gannon et al. |
| 2016/0183875 A1 | 6/2016 | Yang et al. |
| 2016/0196388 A1 | 7/2016 | Lamego |
| 2016/0206277 A1 | 7/2016 | Bidichandani et al. |
| 2016/0228050 A1 | 8/2016 | Sugla et al. |
| 2016/0242654 A1 | 8/2016 | Quinlan |
| 2016/0242681 A1 | 8/2016 | Shen et al. |
| 2016/0256080 A1 | 9/2016 | Shen et al. |
| 2016/0275776 A1 | 9/2016 | Shen et al. |
| 2016/0278652 A1 | 9/2016 | Kaib et al. |
| 2016/0278691 A1 | 9/2016 | Larson et al. |

(56) References Cited

U.S. PATENT DOCUMENTS

| | | |
|---|---|---|
| 2016/0278692 A1 | 9/2016 | Larson et al. |
| 2016/0283665 A1 | 9/2016 | Sampath et al. |
| 2016/0296159 A1 | 10/2016 | Larson et al. |
| 2016/0296160 A1 | 10/2016 | Larson et al. |
| 2016/0302698 A1 | 10/2016 | Perlman |
| 2016/0302715 A1 | 10/2016 | Larson et al. |
| 2016/0328991 A1 | 11/2016 | Simpson |
| 2016/0338640 A1 | 11/2016 | Chan et al. |
| 2016/0338641 A1 | 11/2016 | Chan et al. |
| 2016/0367170 A1 | 12/2016 | Larson et al. |
| 2016/0367173 A1 | 12/2016 | Dalvi et al. |
| 2017/0000410 A1 | 1/2017 | Chan et al. |
| 2017/0020429 A1 | 1/2017 | Chan et al. |
| 2017/0024748 A1 | 1/2017 | Haider |
| 2017/0027498 A1 | 2/2017 | Larson et al. |
| 2017/0042488 A1 | 2/2017 | Muhsin |
| 2017/0049365 A1 | 2/2017 | Perlman et al. |
| 2017/0053083 A1 | 2/2017 | Perlman |
| 2017/0150893 A1 | 6/2017 | McCombie et al. |
| 2017/0156618 A1 | 6/2017 | Narasimhan et al. |
| 2017/0173632 A1 | 6/2017 | Al-Ali |
| 2017/0184630 A1 | 6/2017 | Chan et al. |
| 2017/0202473 A1 | 7/2017 | Narasimhan et al. |
| 2017/0238812 A1 | 8/2017 | Atlas |
| 2017/0251974 A1 | 9/2017 | Shreim et al. |
| 2017/0311116 A1 | 10/2017 | Aga et al. |
| 2017/0311862 A1 | 11/2017 | Aga et al. |
| 2017/0311891 A1 | 11/2017 | Kiani et al. |
| 2017/0311904 A1 | 11/2017 | Davis |
| 2017/0366615 A1 | 12/2017 | Azimi |
| 2018/0028072 A1* | 2/2018 | Shi ............... A61B 5/6833 |
| 2018/0035889 A1 | 2/2018 | Liou et al. |
| 2018/0035909 A1 | 2/2018 | Hadley et al. |
| 2018/0042559 A1 | 2/2018 | Cabrera |
| 2018/0064348 A1 | 3/2018 | Tsuchimoto |
| 2018/0064361 A1 | 3/2018 | Yang et al. |
| 2018/0064595 A1 | 3/2018 | Srinivasan |
| 2018/0078174 A1 | 3/2018 | Chan et al. |
| 2018/0078189 A1 | 3/2018 | Chan et al. |
| 2018/0078190 A1 | 3/2018 | Chan et al. |
| 2018/0078219 A1 | 3/2018 | Selvaraj |
| 2018/0103874 A1 | 4/2018 | Lee et al. |
| 2018/0146862 A1 | 5/2018 | Moon et al. |
| 2018/0160909 A1 | 6/2018 | Damania et al. |
| 2018/0189235 A1 | 7/2018 | Chan et al. |
| 2018/0199871 A1 | 7/2018 | Pauley et al. |
| 2018/0213583 A1 | 7/2018 | Ai-Ali |
| 2018/0220966 A1 | 8/2018 | Cohen |
| 2018/0242926 A1 | 8/2018 | Muhsin et al. |
| 2018/0246639 A1 | 8/2018 | Han |
| 2018/0247353 A1 | 8/2018 | Al-Ali et al. |
| 2018/0247712 A1 | 8/2018 | Muhsin et al. |
| 2018/0249961 A1 | 9/2018 | Ferdosi et al. |
| 2018/0256087 A1 | 9/2018 | Al-Ali et al. |
| 2018/0289289 A1 | 10/2018 | Chan et al. |
| 2018/0296161 A1 | 10/2018 | Shreim et al. |
| 2018/0300919 A1 | 10/2018 | Muhsin et al. |
| 2018/0303365 A1 | 10/2018 | Selvaraj et al. |
| 2018/0303434 A1 | 10/2018 | Selvaraj et al. |
| 2018/0310822 A1 | 11/2018 | Indorf et al. |
| 2018/0310823 A1 | 11/2018 | Al-Ali et al. |
| 2018/0310879 A1 | 11/2018 | Chan et al. |
| 2018/0317826 A1 | 11/2018 | Muhsin |
| 2018/0338708 A1 | 11/2018 | Chan et al. |
| 2019/0015023 A1 | 1/2019 | Monfre |
| 2019/0038455 A1 | 2/2019 | Heitz et al. |
| 2019/0042614 A1 | 2/2019 | Wickenhauser |
| 2019/0059777 A1 | 2/2019 | Aga et al. |
| 2019/0082968 A1 | 3/2019 | Karnik et al. |
| 2019/0090760 A1 | 3/2019 | Kinast et al. |
| 2019/0090781 A1 | 3/2019 | Selvaraj et al. |
| 2019/0117070 A1 | 4/2019 | Muhsin et al. |
| 2019/0150788 A1 | 5/2019 | Selvaraj et al. |
| 2019/0183425 A1 | 6/2019 | Ferdosi et al. |
| 2019/0200941 A1 | 7/2019 | Chandran et al. |
| 2019/0221803 A1 | 7/2019 | Moore et al. |
| 2019/0223722 A1 | 7/2019 | Xi |
| 2019/0238546 A1 | 8/2019 | Petersen et al. |
| 2019/0239787 A1 | 8/2019 | Pauley et al. |
| 2019/0272916 A1 | 9/2019 | Selvaraj et al. |
| 2019/0320906 A1 | 10/2019 | Olsen |
| 2019/0336010 A1 | 11/2019 | Selvaraj et al. |
| 2019/0350665 A1* | 11/2019 | Furutani ............ H01M 10/0585 |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0388013 A1 | 12/2019 | Achmann et al. |
| 2019/0388030 A1 | 12/2019 | Colliou et al. |
| 2020/0011746 A1 | 1/2020 | Allen et al. |
| 2020/0021930 A1 | 1/2020 | Iswanto et al. |
| 2020/0046231 A1 | 2/2020 | Ferdosi et al. |
| 2020/0054218 A1 | 2/2020 | Xi |
| 2020/0054246 A1 | 2/2020 | Banet et al. |
| 2020/0060869 A1 | 2/2020 | Telfort et al. |
| 2020/0069252 A1 | 3/2020 | Upadhya et al. |
| 2020/0069281 A1 | 3/2020 | Chan et al. |
| 2020/0077951 A1 | 3/2020 | Nallathambi et al. |
| 2020/0085310 A1 | 3/2020 | Zahner et al. |
| 2020/0086133 A1 | 3/2020 | Wang et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138314 A1 | 5/2020 | Doctor et al. |
| 2020/0138368 A1 | 5/2020 | Kiani et al. |
| 2020/0138399 A1 | 5/2020 | Li et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0390336 A1 | 12/2020 | Mensch et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0177305 A1 | 6/2021 | Shen et al. |
| 2021/0186337 A1 | 6/2021 | Matsunaga et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275095 A1 | 9/2021 | Sarussi et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0321917 A1 | 10/2021 | Choi et al. |
| 2021/0330228 A1 | 10/2021 | Olsen et al. |
| 2021/0386368 A1 | 12/2021 | Carlsson et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0026946 A1 | 1/2022 | Wen |
| 2022/0031171 A1 | 2/2022 | van der Linden et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0095930 A1 | 3/2022 | Li et al. |

(56) References Cited

U.S. PATENT DOCUMENTS

| | | |
|---|---|---|
| 2022/0096603 A1 | 3/2022 | Kiani et al. |
| 2022/0117520 A1 | 4/2022 | Wang et al. |
| 2022/0133184 A1 | 5/2022 | Garai |
| 2022/0151521 A1 | 5/2022 | Krishnamani et al. |
| 2022/0218244 A1 | 7/2022 | Kiani et al. |
| 2022/0273924 A1 | 9/2022 | Kamen |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0370012 A1 | 11/2022 | Golenberg et al. |
| 2022/0379059 A1 | 12/2022 | Yu et al. |
| 2022/0392610 A1 | 12/2022 | Kiani et al. |
| 2022/0395402 A1 | 12/2022 | Trabish |
| 2022/0401037 A1 | 12/2022 | Sadeghzadeh et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0106359 A1 | 4/2023 | Wang et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0148928 A1 | 5/2023 | O'Dane |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0293047 A1 | 9/2023 | Chun |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkvist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |

FOREIGN PATENT DOCUMENTS

| | | |
|---|---|---|
| CN | 104127181 | 11/2014 |
| CN | 203914879 | 11/2014 |
| CN | 104586398 | 5/2015 |
| CN | 103308069 | 6/2015 |
| CN | 104688196 | 6/2015 |
| CN | 204394477 | 6/2015 |
| CN | 104739420 | 7/2015 |
| CN | 204468059 | 7/2015 |
| CN | 106934444 | 7/2017 |
| EP | 0 735 499 | 10/1996 |
| GB | 6115451 | 1/2021 |
| JP | 10-336064 | 12/1998 |
| JP | 2002-513602 | 5/2002 |
| JP | 2002-542493 | 12/2002 |
| JP | 2003-521985 | 7/2003 |
| JP | 2003-322569 | 11/2003 |
| JP | 2005-218036 | 8/2005 |
| JP | 2005-237479 | 9/2005 |
| JP | 2005-295375 | 10/2005 |
| JP | 2007-095365 | 4/2007 |
| JP | 2007-174051 | 7/2007 |
| JP | 2007-296266 | 11/2007 |
| JP | 2008-027030 | 2/2008 |
| JP | 2008-519635 | 6/2008 |
| JP | 2009-017959 | 1/2009 |
| JP | 2009-529930 | 8/2009 |
| JP | 2010-000286 | 1/2010 |
| JP | 2010-524510 | 7/2010 |
| JP | 2011-510363 | 3/2011 |
| JP | 2012-502671 | 2/2012 |
| JP | 2012-237670 | 12/2012 |
| JP | 2013-034511 | 2/2013 |
| JP | 2013-526900 | 6/2013 |
| JP | 2013-544616 | 12/2013 |
| JP | D1531996 | 7/2015 |
| JP | D1700151 | 1/2021 |
| JP | 2002-065640 | 3/2022 |
| JP | D1751168 | 10/2022 |
| KR | 301000495.0000 | 10/2018 |
| KR | 301222494.0000 | 10/2022 |
| WO | WO 98/029790 | 7/1998 |
| WO | WO 99/013766 | 3/1999 |
| WO | WO 00/063713 | 10/2000 |
| WO | WO 2004/056266 | 7/2004 |
| WO | WO 2004/059551 | 7/2004 |
| WO | WO 2009/036313 | 3/2009 |
| WO | WO 2010/125096 | 11/2010 |
| WO | WO 2010/135518 | 11/2010 |
| WO | WO 2011/002904 | 1/2011 |
| WO | WO 2013/033631 | 3/2013 |
| WO | WO 2013/056160 | 4/2013 |
| WO | WO 2013/119982 | 8/2013 |
| WO | WO 2013/120014 | 8/2013 |
| WO | WO 2014/047205 | 3/2014 |
| WO | WO 2014/083888 | 6/2014 |
| WO | WO 2014/197822 | 12/2014 |
| WO | WO 2015/054665 | 4/2015 |
| WO | WO 2015/074007 | 5/2015 |
| WO | WO 2015/123157 | 8/2015 |
| WO | WO 2015/172246 | 11/2015 |
| WO | WO 2016/058032 | 4/2016 |
| WO | WO 2016/185905 | 11/2016 |
| WO | WO 2017/040700 | 3/2017 |
| WO | WO 2018/071715 | 4/2018 |
| WO | WO 2018/152566 | 8/2018 |
| WO | WO 2019/005801 | 1/2019 |
| WO | WO 2019/161277 | 8/2019 |
| WO | WO 2021/189002 | 9/2021 |
| WO | WO 2023/049712 | 3/2023 |
| WO | WO 2024/036327 | 2/2024 |

OTHER PUBLICATIONS

US 9,167,986 B2, 10/2015, Aga et al. (withdrawn)
US 9,241,629 B2, 01/2016, Yang et al. (withdrawn)
US 2022/0192529 A1, 06/2022, Al-Ali et al. (withdrawn)
US 2024/0016391 A1, 01/2024, Lapotko et al. (withdrawn)
Larsen, Katrina, "The 4 Best CGM Devices for Measuring Blood Sugar in 2024", https://www.nutrisense.io/blog/best-continuous-glucose-monitors?utm_source=google&utm_medium=cpc&utm_campaign=ggl_search_us_dsa_purchas, Jan. 5, 2024, pp. 10.
Milberger, Carol, "The Best Continuous Glucose Monitors", https://www.wired.com/gallery/the-best-continuous-glucose-monitors/, Nov. 27, 2023, pp. 9.

(56) References Cited

OTHER PUBLICATIONS

Letter from Payal Patel to Masimo Corporation re 510(k) No. K203215, U.S. Food & Drug Administration, dated Jun. 11, 2021 in 13 pages.
Aminian et al., "Spatio-Temporal Parameters of Gait Measured by an Ambulatory System Using Miniature Gyroscopes", Journal of Biomechanics, 2002, vol. 35, pp. 689-699.
Anliker et al., "AMON: A Wearable Multiparameter Medical Monitoring and Alert System", IEEE Transactions on Information Technology in Biomedicine, vol. 8, No. 4, Dec. 2004, pp. 415-427.
Asada et al., "Mobile Monitoring with Wearable Photoplethysmographic Biosensors", IEEE Engineering in Medicine and Biology Magazine, May/Jun. 2003, pp. 28-40.
Ayello et al., "How and Why to Do Pressure Ulcer Risk Assessment", Advances in Skin & Wound Care, May/Jun. 2002, vol. 15, No. 3, pp. 125-133.
Bergstrom et al., "A Prospective Study of Pressure Sore Risk Among Institutionalized Elderly", Journal of the American Geriatrics Society, Aug. 1992, vol. 40, No. 8, pp. 747-758.
Bourke et al., "Evaluation of a Threshold-Based Tri-Axial Accelerometer Fall Detection Algorithm", Gait & Posture, vol. 26, 2007, pp. 194-199.
Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.
Caporusso et al., "A Pervasive Solution for Risk Awareness in the Context of Fall Prevention", Pervasive Health, 2009, pp. 8.
Capuano et al., "Remote Telemetry—New Twists for Old Technology", Nursing Management, Jul. 1995, vol. 26, No. 7, pp. 26-32.
Chen et al., "In-Bed Fibre Optic Breathing and Movement Sensor for Non-Intrusive Monitoring", Proceedings of SPIE vol. 7173, 2009, pp. 6.
Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.
Degen et al., "SPEEDY: A Fall Detector in a Wrist Watch", Proceedings of the Seventh IEEE International Symposium on Wearable Computers (ISWC'03), 2003, pp. 184-187.
Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, August 28-Sep. 1, 2012, pp. 4513-4516.
Di Rienzo et al., "MagIC System: a New Textile-Based Wearable Device for Biological Signal Monitoring. Applicability in Daily Life and Clinical Setting", Proceedings of the 2005 IEEE Engineering in Medicine and Biology 27th Annual Conference Shanghai, China, Sep. 1-4, 2005, pp. 7167-7169.
Dinh et al., "A Fall and Near-Fall Assessment and Evaluation System", The Open Biomedical Engineering Journal, 2009, vol. 3, pp. 1-7.
Elmer-Dewitt, Philip, "Apple's iWatch: The killer apps may be in hospitals, not health clubs", Fortune.com, Feb. 3, 2014, http://fortune.com/2014/02/03/apples-iwatch-the-killer-apps-may-be-in-hospitals-not-health-clubs/, 4 pages.
Giansanti et al., "Assessment of Fall-Risk by Means of a Neural Network Based on Parameters Assessed by a Wearable Device During Posturography", Medical Engineering & Physics, vol. 30, 2008, pp. 367-372.
Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.
Grundy et al., "Telemedicine in Critical Care: An Experiment in Health Care Delivery", JACEP, Oct. 1977, vol. 6, No. 10, pp. 439-444.
Grundy et al., "Telemedicine in Critical Care: Problems in Design, Implementation and Assessment", Jul. 1982, vol. 10, No. 7, pp. 471-475.
Gunningberg et al., "Accuracy in the Recording of Pressure Ulcers and Prevention after Implementing an Electronic Health Record in Hospital Care", Quality Safe Health Care, 2008, vol. 17, pp. 281-285.
Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.
Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.
Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.
Kang et al., "A Wrist-Worn Integrated Health Monitoring Instrument with a Tele-Reporting Device for Telemedicine and Telecare", IEEE Transaction on Instrumentation and Measurement, vol. 55, No. 5, Oct. 2006, pp. 1655-1661.
Kärki et al., "Pressure Mapping System for Physiological Measurements", XVIII IMEKO World Congress, Metrology for a Sustainable Development, Sep. 17-22, 2006, Rio de Janeiro, Brazil, pp. 5.
Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.
Lindemann et al., "Evaluation of a Fall Detector Based on Accelerometers: A Pilot Study", Medical & Biological Engineering & Computing, vol. 43, 2005, pp. 548-551.
Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, pp. 2.
Luo et al., "A Dynamic Motion Pattern Analysis Approach to Fall Detection", 2004 IEEE International Workshop on Biomedical Circuits & Systems, Dec. 1-3, 2004, pp. S2.1-5-S2.1-8.
"Masimo Announces FDA Clearance of Centroid™", Business Wire, Jun. 25, 2020, pp. 3.
Mathie et al., "A System for Monitoring Posture and Physical Activity Using Accelerometers", Engineering in Medicine and Biology Society, 2001. Proceedings of the 23rd Annual International Conference of the IEEE, Oct. 25-28, 2001, pp. 3654-3657.
McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.
Merbitz et al., "Wheelchair Push-ups: Measuring Pressure Relief Frequency", Archives of Physical Medicine and Rehabilitation, vol. 66, No. 7, Jul. 1985, pp. 433-438.
Narayanan et al., "Falls Management: Detection and Prevention, Using a Waist-Mounted Triaxial Accelerometer", Proceedings of the 29th Annual International Conference of the IEEE EMBS Cité Internationale, Lyon, France, Aug. 23-26, 2007, pp. 4037-4040.
Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.
Nyan et al., "A Wearable System for Pre-Impact Fall Detection", Journal of Biomechanics, vol. 41, 2008, pp. 3475-3481.
Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.
O'Donovan et al., "A Context Aware Wireless Body Area Network", Pervasive Health, 2009, pp. 8.
Pannurat et al., "Automatic Fall Monitoring: A Review", Sensors, 2014, vol. 14, pp. 12900-12936.
Pérolle et al., "Automatic Fall Detection and Activity Monitoring for Elderly", Jan. 2007, pp. 5.

(56) References Cited

OTHER PUBLICATIONS

Po et al., "Overview of MEMSWear II—Incorporating MEMS Technology Into Smart Shirt for Geriatric Care", Institute of Physics Publishing, International MEMS Conference 2006, Journal of Physics: Conference Series 34, 2006, pp. 1079-1085.

Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.

Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.

Rysavy, Peter, "Making the Call with Two-Way Paging", Network Computing, Published Jan. 15, 1997, www.rysavy.com/Articles/twoway.htm, pp. 5.

Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.

Spillman Jr., et al., "A 'Smart' Bed for Non-Intrusive Monitoring of Patient Physiological Factors", Measurement Science and Technology, Aug. 2004, vol. 15, No. 8, pp. 1614-1620.

Lötters et al., "Procedure for in-use Calibration of Triaxial Accelerometers in Medical Applications", Sensors and Actuators A: Physical, Jun. 15, 1998, vol. 68, No. 1-3, pp. 221-228.

Virtual EXPO Group, Home Page. (HJ30049031) in 1 page.

Wachter et al., "The Employment of an Iterative Design Process to Develop a Pulmonary Graphical Display", Journal of the American Medical Informatics Association, vol. 10, No. 4, Jul./Aug. 2003, pp. 363-372.

Webster, John G., "A Pressure Mat for Preventing Pressure Sores", IEEE Engineering in Medicine & Biology Society 11th Annual International Conference, 1989, pp. 2.

Williams et al., "A Remote Electronic Monitoring System for the Prevention of Pressure Sores", Proceedings of the 19th International Conference, IEEE/EMBS Oct. 30-Nov. 2, 1997, Chicago, IL, pp. 1076-1079.

Wu et al., "Portable Preimpact Fall Detector with Inertial Sensors", IEEE Transactions on Neural Systems and Rehabilitation Engineering, vol. 16, No. 2, Apr. 2008, pp. 178-183.

International Search Report & Written Opinion in PCT Application No. PCT/US2013/025384, dated Aug. 6, 2013.

International Preliminary Report on Patentability & Written Opinion in PCT/US2013/025384, dated Aug. 21, 2014.

International Search Report & Written Opinion in PCT Application No. PCT/US2016/049751, dated Mar. 13, 2017.

International Preliminary Report on Patentability & Written Opinion in PCT Application No. PCT/US2016/049751, dated Mar. 6, 2018.

International Search Report & Written Opinion in PCT Application No. PCT/US2017/056405, dated Jan. 26, 2018.

International Preliminary Report on Patentability & Written Opinion in PCT Application No. PCT/US2017/056405, dated Apr. 25, 2019.

International Search Report & Written Opinion in PCT Application No. PCT/US2021/023331, dated Jun. 22, 2021.

International Search Report & Written Opinion in PCT Application No. PCT/US2022/076733, dated Dec. 16, 2022.

"Diabetic Danica Explains Dexcom Share", YouTube.com, https://www.youtube.com/watch?v=5YZKK34ELeg, May 24, 2017, 1 page.

Masimo, "Radius T°™ Wearable Thermometer", Oct. 9, 2020, https://www.masimo.com/en-us/product/all-brands/137728.html, retrieved Jul. 17, 2024, pp. 2.

\* cited by examiner

WEARABLE DEVICE FOR NONINVASIVE BODY TEMPERATURE MEASUREMENT

INCORPORATION BY REFERENCE TO ANY PRIORITY APPLICATIONS

This application is a divisional of U.S. patent application Ser. No. 17/206,907, entitled "WEARABLE DEVICE FOR NONINVASIVE BODY TEMPERATURE MEASUREMENT," filed Mar. 19, 2021, which claims the benefit of priority under 35 U.S.C. § 119(e) to U.S. Patent Application No. 63/106,273, entitled "WEARABLE DEVICE FOR NONINVASIVE BODY TEMPERATURE MEASUREMENT," filed Oct. 27, 2020, U.S. Patent Application No. 63/056,925, entitled "WEARABLE DEVICE FOR NONINVASIVE BODY TEMPERATURE MEASUREMENT," filed Jul. 27, 2020, U.S. Patent Application No. 63/065,961, entitled "HEALTH SCREENING AND MONITORING SYSTEM," filed Aug. 14, 2020, U.S. Patent Application No. 63/049,478, entitled "REMOTE PATIENT MANAGEMENT AND MONITORING SYSTEMS AND METHODS," filed Jul. 8, 2020, U.S. Patent Application No. 62/992,808, entitled "REMOTE PATIENT MANAGEMENT AND MONITORING," filed Mar. 20, 2020, U.S. Patent Application No. 62/992,779, entitled "OPIOID OVERDOSE MONITORING USER INTERFACE," filed Mar. 20, 2020, and U.S. Patent Application No. 63/010,669, entitled "REMOTE PATIENT MANAGEMENT AND MONITORING," filed Apr. 15, 2020. All of the above-mentioned applications are hereby incorporated by reference herein in their entireties. Any and all applications for which a foreign or domestic priority claim is identified in the Application Data Sheet as filed with the present application are hereby incorporated by reference under 37 CFR 1.57.

TECHNICAL FIELD

The present disclosure relates to devices, methods, and/or systems for monitoring a subject's physiological information. More specifically, the present disclosure describes, among other things, a wearable device that measures a subject's body temperature.

BACKGROUND

Core body temperature is an important vital sign used by clinicians to monitor and/or manage the condition of a subject (for example, a patient). Core body temperature is the internal temperature of a subject. Internal body temperatures are typically maintained within a specific range in order for the body to carry out essential functions. Variations in core body temperature can be indicative of a deteriorating condition of a subject and can negatively impact the body's ability to maintain critical life-sustaining functions. Despite the importance of core body temperature as a vital sign, some commonly employed devices, methods, and/or systems for estimating core body temperature based on skin surface or peripheral measurements are lacking. Skin surface temperature, typically measured using single point measurement devices or heat flux measurement devices, can vary dramatically from core body temperature in some cases, depending on, for example, physiology of the subject (for example, skin thickness), environment of the user, perfusion, and/or other conditions. "Clinical temperature" measurements—temperature measurements typically obtained with a thermometer at a subject's periphery (such as at the subject's armpit, rectum, or under a subject's tongue)—do not represent a true measurement of internal body temperature, but rather, simply an approximation. There is a great need for improved devices, methods, and systems for non-invasively measuring (continuously or periodically) and/or transmitting (for example, wirelessly) a subject's core body temperature.

SUMMARY

Various implementations of the wearable devices disclosed herein provide improved devices, methods, and systems for non-invasively measuring (continuously or periodically) and/or transmitting (for example, wirelessly) a subject's core body temperature. Various embodiments of the disclosed wearable devices can be comfortably worn by a user over a long period of time (for example, 1 day, 2 days, 3 days, 4 days, 5 days, 6 days, 7 days, 8 days, 9 days, or 10 days), can monitor (continuously or periodically) the user's core body temperature alone or in combination with other physiological parameters, and can transmit (for example, wirelessly) such physiological information to separate devices (for example, a mobile device). Some embodiments of the disclosed wearable devices can be configured to be removed and reapplied/re-secured in order to position the devices in various locations on the user's body. Some embodiments of the disclosed wearable devices (or portions of such devices) can be disposable, which can reduce the risk of cross-contamination between multiple users. Some embodiments of the disclosed wearable devices (or portions of such devices) can be waterproof, thereby providing minimal disruption to ordinary activities of the user (for example, showering).

A wearable device configured for noninvasive measurement of a user's body temperature can comprise: a housing; a first substrate coupled to the housing and comprising an opening; a second substrate coupled to the first substrate and configured to secure to skin of a user when the wearable device is in use; a mounting frame enclosed by the housing and the first substrate; a circuit board secured by the mounting frame; a first temperature sensor coupled to the circuit board and configured to determine a body temperature of the user; and a thermally conductive probe secured by the mounting frame and positioned proximate to the first temperature sensor, the thermally conductive probe configured to extend at least partially through the opening in the first substrate and further configured to transmit a thermal energy from a portion of the user's skin to the first temperature sensor when the wearable device is in use. The wearable device can be configured to secure to skin of the user and/or can be configured for continuous noninvasive measurement of the user's body temperature. In some variants, the only type of physiological parameter measured and/or monitored by the wearable device is body temperature. In some variants, the only type of physiological parameter measured and/or monitored by the wearable device is body temperature. In some variants, the wearable device does not include an accelerometer, a gyroscope, a magnetometer, an oximetry sensor, a moisture sensor, an impedance sensor, an acoustic/respiration sensor, and/or an ECG sensor. In some variants, the first and second substrates are integrally formed with one another.

The circuit board can comprise a first surface, a second surface opposite the first surface, and one or more openings extending through the circuit board from the first surface to the second surface, the second surface positioned closer to the second substrate than the first surface. The thermally conductive probe can be positioned adjacent the one or more openings and the second surface of the circuit board. The first temperature sensor can be mounted to the first surface of the circuit board adjacent the one or more openings in the circuit board. The one or more openings of the circuit board can be configured to allow said thermal energy to pass through the circuit board to the first temperature sensor. The one or more openings of the circuit board can be filled with a thermally conductive material. The one or more openings of the circuit board can be not filled with a material. The one or more openings of the circuit board can comprise a plurality of openings. Each of the one or more openings of the circuit board can be circular. The first temperature sensor can be configured to determine the body temperature of the user in one minute intervals.

The wearable device can further comprise at least one thermally conductive material positioned between the one or more openings of the circuit board and the thermally conductive probe. The at least one thermally conductive material can comprise a first thermally conductive material and a second thermally conductive material, the first thermally conductive material comprising a thermal paste and the second thermally conductive material comprising a metallic material. The thermal paste can comprise zinc oxide. The metallic material can comprise at least one of gold and copper.

When the wearable device is secured to the user's skin via the second substrate, the second substrate can be positioned between the user's skin and the thermally conductive probe. In some variants, the thermally conductive probe does not contact the portion of the skin of the user when the wearable device is secured to the user's skin during use. An axis extending through a center of a cross-section of the thermally conductive probe and along a height of the thermally conductive probe can be oriented perpendicular with respect to a plane of the circuit board. The thermally conductive probe can comprise a width that is smaller than the height. The thermally conductive probe can comprise a first end, a second end opposite the first end, and a height extending between the first and second ends, and wherein the second end is configured to apply pressure to the portion of the skin of the user when the wearable device is secured to the user. When the wearable device is secured to the user's skin via the second substrate, the second substrate can be positioned between the user's skin and the second end of the thermally conductive probe.

The mounting frame can comprise one or more posts and the housing can comprise one or more cavities. Each of the one or more posts can be configured to secure within one of the one or more cavities. The one or more posts can comprise two posts positioned on opposite sides of the mounting frame and the one or more cavities can comprise two cavities. The circuit board can comprise one or more notches along one or more sides of the circuit board, the one or more notches sized and shaped to receive a portion of the one or more posts. The mounting frame can comprise a slot configured to receive and secure the thermally conductive probe. The slot can be configured to surround a portion of a perimeter of a cross-section of the thermally conductive probe. The slot can be configured to surround less than an entire perimeter of a cross-section of the thermally conductive probe. The thermally conductive probe can comprises a metallic material. The thermally conductive probe can comprise aluminum. The thermally conductive probe can be rigid.

The first substrate can comprise foam. The second substrate can comprise a fabric material and an adhesive material. The housing can comprise a main body and a rim extending around a perimeter of the main body, and the wearable device can further comprises a third substrate including an opening configured to receive the main body of the housing, wherein the third substrate is coupled to the first substrate, and wherein the rim of the housing is secured between the first and third substrates. The wearable device can further comprise a release liner configured to removably secure to the second substrate.

The opening in the first substrate can be sized and shaped to correspond to a size and shape of a perimeter of a cross-section of the thermally conductive probe. The opening in the first substrate and the cross-section of the thermally conductive probe can be circular.

The wearable device can further comprise a second temperature sensor coupled to the circuit board and spaced away from the first temperature sensor by a first distance, the second temperature sensor configured to measure an ambient temperature outside an interior of the housing. The wearable device can further comprise a thermally conductive material extending between the second temperature sensor and an interior surface of the housing, wherein the thermally conductive material is configured to transfer ambient thermal energy from the interior surface of the housing to the second temperature sensor. The second thermally conductive material can comprise a thermal putty configured to at least partially conform to a shape of a portion of the interior surface of the housing. The thermal putty can comprise a ceramic filled silicone sheet.

The wearable device can further comprise a wireless transceiver coupled to the circuit board and configured to wirelessly transmit one or more signals responsive to the determined body temperature over a wireless communication protocol. The wearable device can further comprise a third substrate positioned between the circuit board and the second substrate, wherein the third substrate is configured to reflect at least a portion of the one or more signals wirelessly transmitted from the wireless transceiver away from the user's skin when the wearable device is in use. The third substrate can comprise metallized polypropylene.

The wearable device can further comprise a near field communication (NFC) tag configured to communicate with an NFC reader of a separate computing device. The NFC tag can be secured to an interior surface of the housing. The wearable device can further comprise a battery configured to provide power to the circuit board. The wearable device can further comprise a battery holder configured to couple the battery to the circuit board.

A wearable device configured for noninvasive measurement of a user's body temperature can comprise: a housing; a circuit board; a temperature sensor coupled to the circuit board and configured to generate one or more signals responsive to a thermal energy of a user; a battery configured to provide power to the circuit board; and a mounting frame configured to secure the circuit board to the housing, the mounting frame comprising a first end and a second end opposite the first end, the second end positioned adjacent the battery. The mounting frame, the circuit board, the temperature sensor, and the battery can be at least partially enclosed by the housing. The second end of the mounting frame can be sized and shaped to conform to a size and shape of a portion of the battery, thereby maximizing a size of the battery within the housing of the wearable device.

The second end of the mounting frame can be sized and shaped to surround approximately half of a perimeter of the battery. The second end of the mounting frame can be sized and shaped to surround less than half of a perimeter of the battery. The battery can comprise a circular shape and wherein the second end of the mounting frame can at least partially comprise a half-circle shape configured to surround a portion of a perimeter of the battery. The wearable device can further comprise a battery holder configured to couple the battery to the circuit board, the battery holder comprising opposing arms configured to electrically connect to electrical contacts of the circuit board. The mounting frame can comprise notches at corners of the second end, the notches configured to facilitate alignment of the battery holder and the mounting frame.

A wearable device configured for noninvasive measurement of a user's body temperature can comprise: a housing; a circuit board at least partially enclosed by the housing, the circuit board comprising a first surface, a second surface opposite the first surface, and at least one hole extending through the circuit board from the first surface to the second surface; a first temperature sensor electrically coupled with the circuit board and positioned adjacent the first surface and the at least one hole of the circuit board; a thermally conductive probe comprising a first end and a second end opposite the first end, wherein the first end is positioned adjacent the second surface of the circuit board proximate the at least one hole and aligned with the first temperature sensor; a mounting frame configured to secure the thermally conductive probe and the circuit board to the housing; and one or more substrates operatively connected to the housing and configured to be positioned proximate skin of a user when the wearable device is in use, wherein at least one of the one or more substrates comprises an opening configured to allow at least a portion of the thermally conductive probe to pass at least partially therethrough. The second end of the thermally conductive probe can be configured to be positioned proximate to a portion of the skin of the user when the wearable device is secured to the user, the thermally conductive probe configured to transmit a thermal energy of the user to the first temperature sensor via the at least one hole extending through the circuit board, the first temperature sensor configured to determine a body temperature of the user based on said transmitted thermal energy.

The wearable device can further comprise a first thermally conductive material positioned between the first end of the thermally conductive probe and the first temperature sensor. The first thermally conductive material can comprise a thermal paste positioned between the first end of the thermally conductive probe and the second surface of the circuit board. The thermal paste can comprise zinc oxide. The wearable device can further comprise a second thermally conductive material positioned between the first end of the thermally conductive probe and the first temperature sensor. The first thermally conductive material can comprise a thermal paste positioned between the first end of the thermally conductive probe and the second surface of the circuit board. The second thermally conductive material can comprise a metallic material. The thermal paste can comprise zinc oxide. The metallic material can comprise at least one of gold and copper. The at least one hole of the circuit board can be filled with a thermally conductive material. The at least one hole of the circuit board can be not filled with a thermally conductive material. The at least one hole of the circuit board can comprise a plurality of holes. An axis extending through a center of a cross-section of the thermally conductive probe and along a height of the thermally conductive probe can be oriented perpendicular with respect to a plane of the circuit board. The one or more substrates can comprise a first substrate and a second substrate, said first substrate comprising said opening and coupled to the second substrate, said second substrate configured to secure to the skin of the user when the wearable device is in use. When the wearable device is secured to the user's skin via the second substrate, the second substrate can be positioned between the user's skin and the second end of the thermally conductive probe. The second end of the thermally conductive probe can be configured to apply pressure to the portion of the skin of the user when the wearable device is secured to the user. When the wearable device is secured to the user's skin via the second substrate, the second substrate can be positioned between the user's skin and the second end of the thermally conductive probe. The housing can comprise a main body and a rim extending around a perimeter of the main body. The wearable device can further comprise a third substrate including an opening configured to receive the main body of the housing. The third substrate can be coupled to the first substrate and the rim of the housing can be secured between the first and third substrates. The mounting frame can comprise a slot configured to receive and secure the thermally conductive probe. The slot can be configured to surround a portion of a perimeter of a cross-section of the thermally conductive probe. The slot can be configured to surround less than an entire perimeter of a cross-section of the thermally conductive probe. The thermally conductive probe can comprise a metallic material. The thermally conductive probe can comprise aluminum. The thermally conductive probe can rigid.

A wearable device configured for continuous and noninvasive measurement of a user's body temperature can comprise: a housing; a circuit board at least partially enclosed by the housing, the circuit board comprising a first surface, a second surface opposite the first surface, and at least one hole extending through the circuit board from the first surface to the second surface; a first temperature sensor electrically coupled with the circuit board and positioned adjacent the first surface and the at least one hole of the circuit board; a thermally conductive probe comprising a first end and a second end opposite the first end, wherein the first end is positioned adjacent the second surface of the circuit board proximate the at least one hole and aligned with the first temperature sensor; a first thermally conductive material positioned between the first end of the probe and the first temperature sensor; a mounting frame configured to secure the thermally conductive probe and the circuit board to the housing; and one or more substrates operatively connected to the housing and configured to be positioned proximate skin of the user when the wearable physiological sensor is in use, wherein at least one of the one or more substrates comprises an opening configured to allow at least a portion of the probe to pass therethrough. The second end of the thermally conductive probe can be positioned proximate to a portion of the skin of the user when the wearable physiological sensor is secured to the user during use. The thermally conductive probe can be configured to transmit a thermal energy of the user to the first temperature sensor, and the first temperature sensor can be configured to determine a body temperature of the user based on said received thermal energy.

A wearable device configured for continuous and noninvasive measurement of a user's body temperature can comprise: a housing; a circuit board at least partially enclosed by the housing; a first temperature sensor coupled to the circuit board; a thermally conductive probe vertically aligned with the first temperature sensor and comprising a first end and a second end opposite the first end, the first end positioned closer to the circuit board than the second end; a mounting frame configured to at least partially secure the thermally conductive probe and the circuit board to the housing; and one or more substrates coupled to the housing and configured to contact skin of a user when the wearable device is in use, wherein, when the one or more substrates contact the user's skin, the second end of the thermally conductive probe is positioned proximate to a portion of the skin. The thermally conductive probe can be configured to transmit a thermal energy of the user to the first temperature sensor and the first temperature sensor can be configured to determine a body temperature of the user based on said thermal energy.

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

BRIEF DESCRIPTION OF THE DRAWINGS

Certain features of this disclosure are described below with reference to the drawings. The illustrated embodiments are intended to illustrate, but not to limit, the embodiments. Various features of the different disclosed embodiments can be combined to form further embodiments, which are part of this disclosure.

DETAILED DESCRIPTION

Various features and advantages of this disclosure will now be described with reference to the accompanying figures. The following description is merely illustrative in nature and is in no way intended to limit the disclosure, its application, or uses. This disclosure extends beyond the specifically disclosed embodiments and/or uses and obvious modifications and equivalents thereof. Thus, it is intended that the scope of this disclosure should not be limited by any particular embodiments described below. The features of the illustrated embodiments can be modified, combined, removed, and/or substituted as will be apparent to those of ordinary skill in the art upon consideration of the principles disclosed herein.

Figure 1:
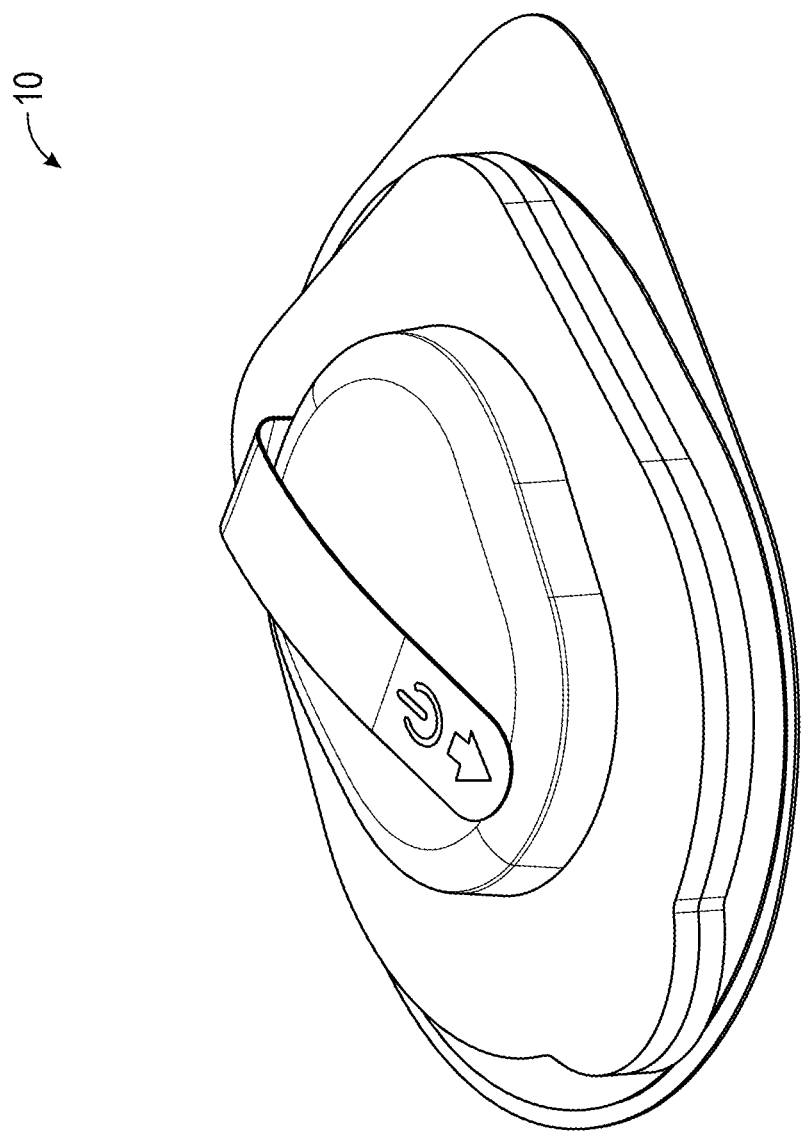
FIG. 1 illustrates a top perspective view of a wearable device in accordance with aspects of this disclosure.
Figure 7:
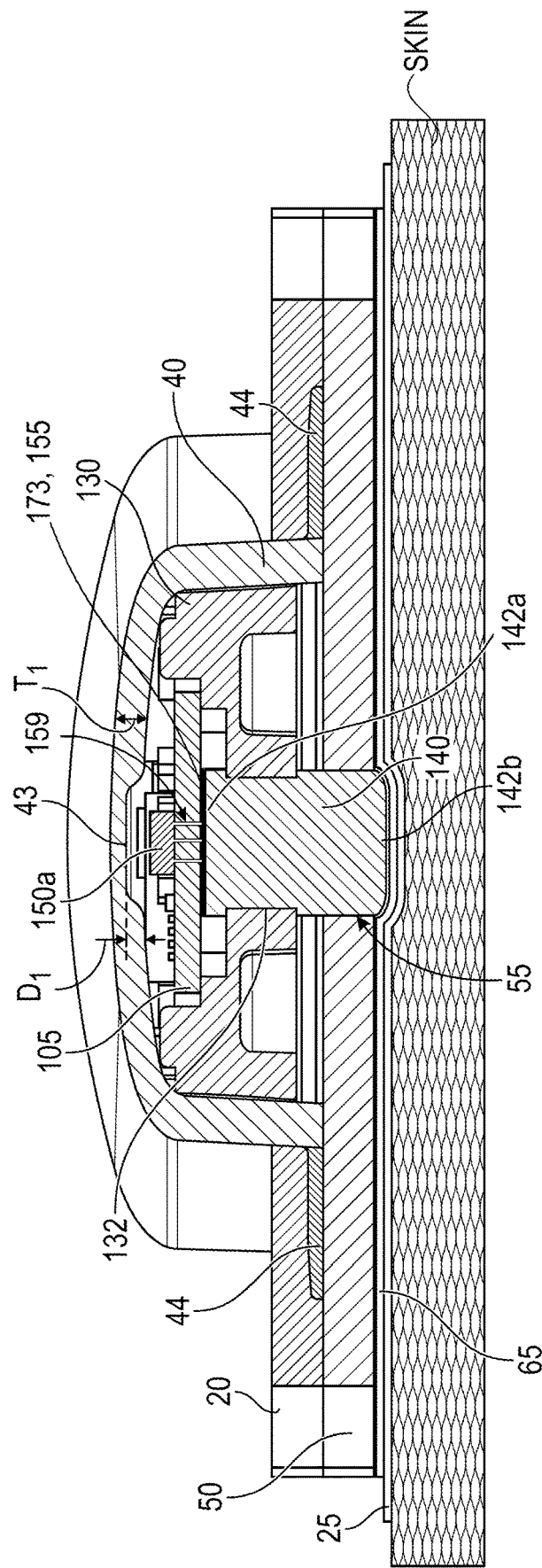
FIG. 7 illustrates a cross-section taken through a portion of the wearable device as shown in FIG. 2C in accordance with aspects of this disclosure.

FIG. 1 illustrates a top perspective view of a wearable device 10 (which may also be referred to herein as "physiological measurement device", "physiological monitoring device", "wearable physiological sensor", "wearable physiological device") that can measure and/or monitor one or more physiological parameters of a subject, as discussed further below. The wearable device 10 can secure to a portion of a subject's body, such as a torso, chest, back, arm, neck, leg, under the arm (e.g., armpit), among other portions of the subject's body. The wearable device 10 can secure (for example, removably secure) to skin of a subject and continuously and/or noninvasively measure the subject's temperature with one or more temperature sensors. Additionally, as discussed below, the wearable device 10 can continuously or periodically wirelessly transmit temperature data of the subject to a separate device. FIG. 7, which is discussed in more detail below, illustrates a cross-section taken through the wearable device 10 when the wearable device 10 is secured to skin of a subject.

As illustrated in FIG. 7 and as discussed further below, the wearable device 10 can include a thermally conductive probe 140 (or 240) that extends toward the subject's skin and transmits thermal energy from the skin in a direction towards a temperature sensor of the wearable device 10 (such as temperature sensor 150a discussed further below). As also discussed below, the thermally conductive probe 140 (or thermally conductive probe 240) can contact (for example, indirectly via substrate 25) and/or apply pressure to the subject's skin, which can facilitate thermal transmissivity. In some variants, the thermally conductive probe 140 does not contact the subject's skin when the wearable device 10 is secured to the subject. For example, the substrate 25 can be positioned between the thermally conductive probe 140 and the subject's skin when the wearable device 10 is secured to the subject.

Figure 2A:
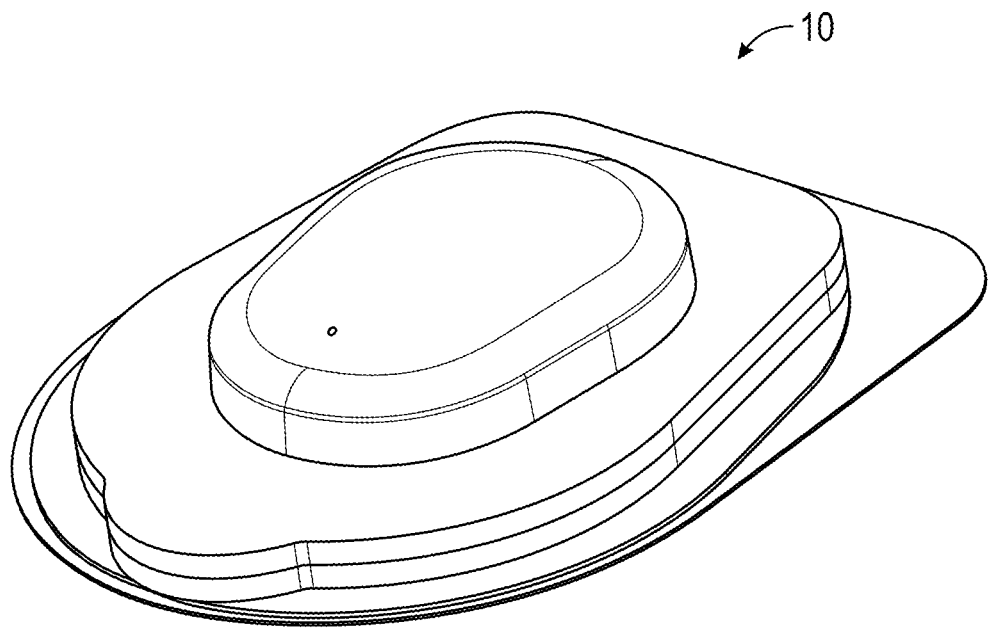
FIGS. 2A and 2B illustrate top perspective views of the wearable device of FIG. 1 in accordance with aspects of this disclosure.
Figure 2B:
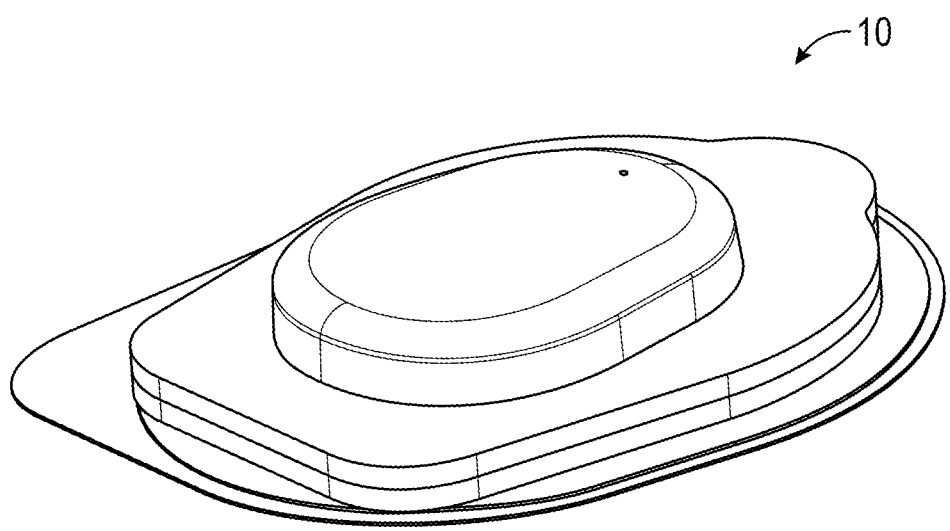
Figure 2C:
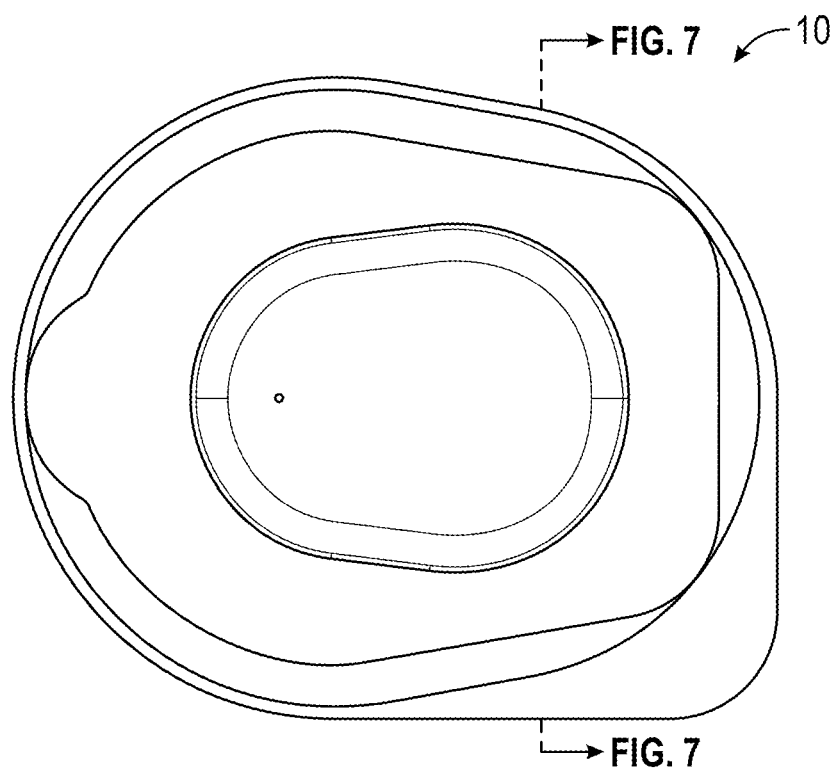
FIG. 2C illustrates a top view of the wearable device of FIG. 1 in accordance with aspects of this disclosure.
Figure 2D:
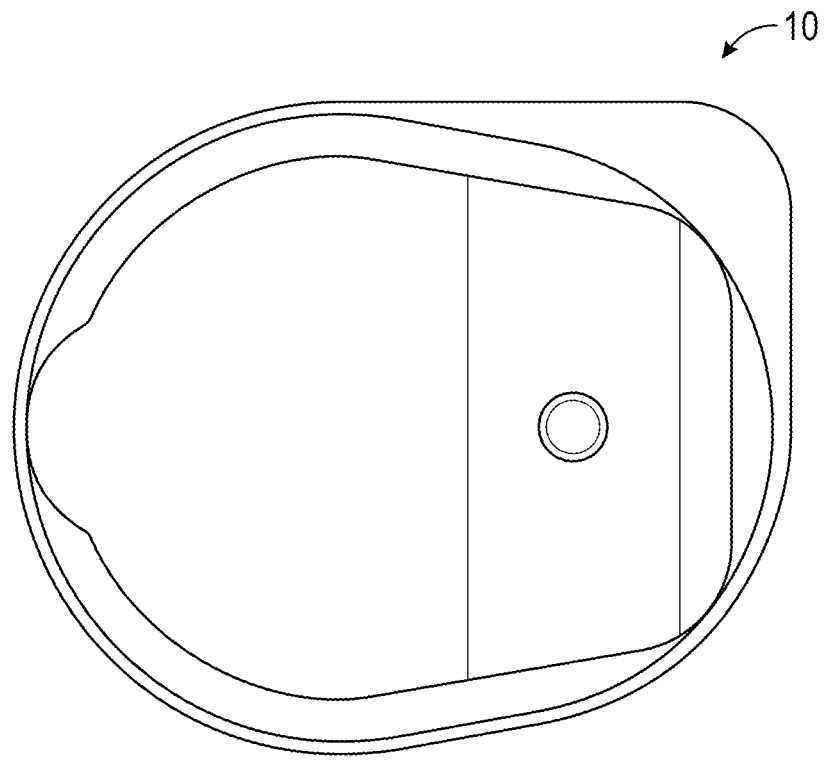
FIG. 2D illustrates a bottom view of the wearable device of FIG. 1 in accordance with aspects of this disclosure.
Figure 2E:
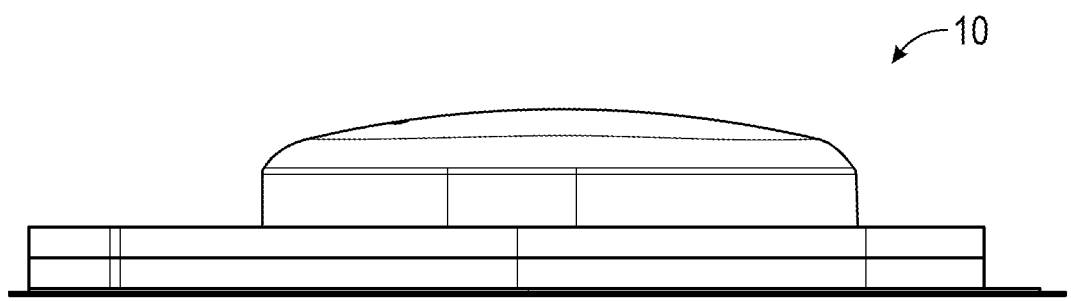
FIG. 2E illustrates a side view of the wearable device of FIG. 1 in accordance with aspects of this disclosure.
Figure 2F:
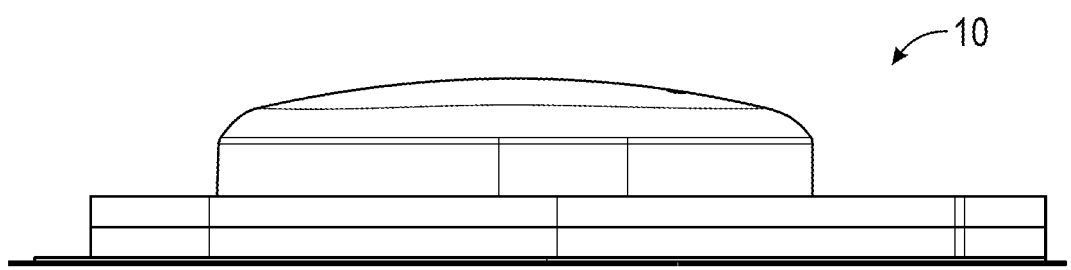
FIG. 2F illustrates another side view of the wearable device of FIG. 1 in accordance with aspects of this disclosure.
Figure 2G:
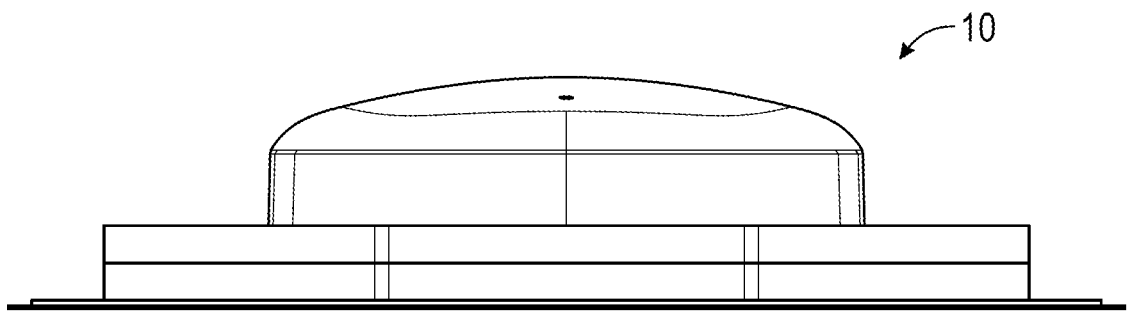
FIG. 2G illustrates a front view of the wearable device of FIG. 1 in accordance with aspects of this disclosure.
Figure 2H:
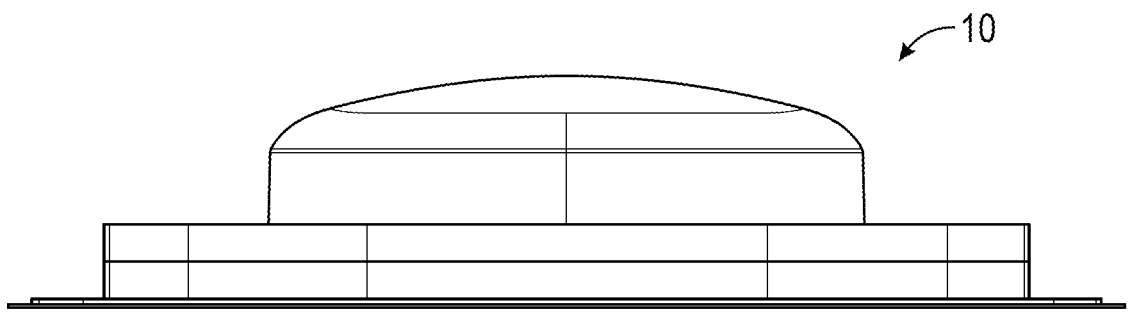
FIG. 2H illustrates a back view of the wearable device of FIG. 1 in accordance with aspects of this disclosure.
Figure 3A:
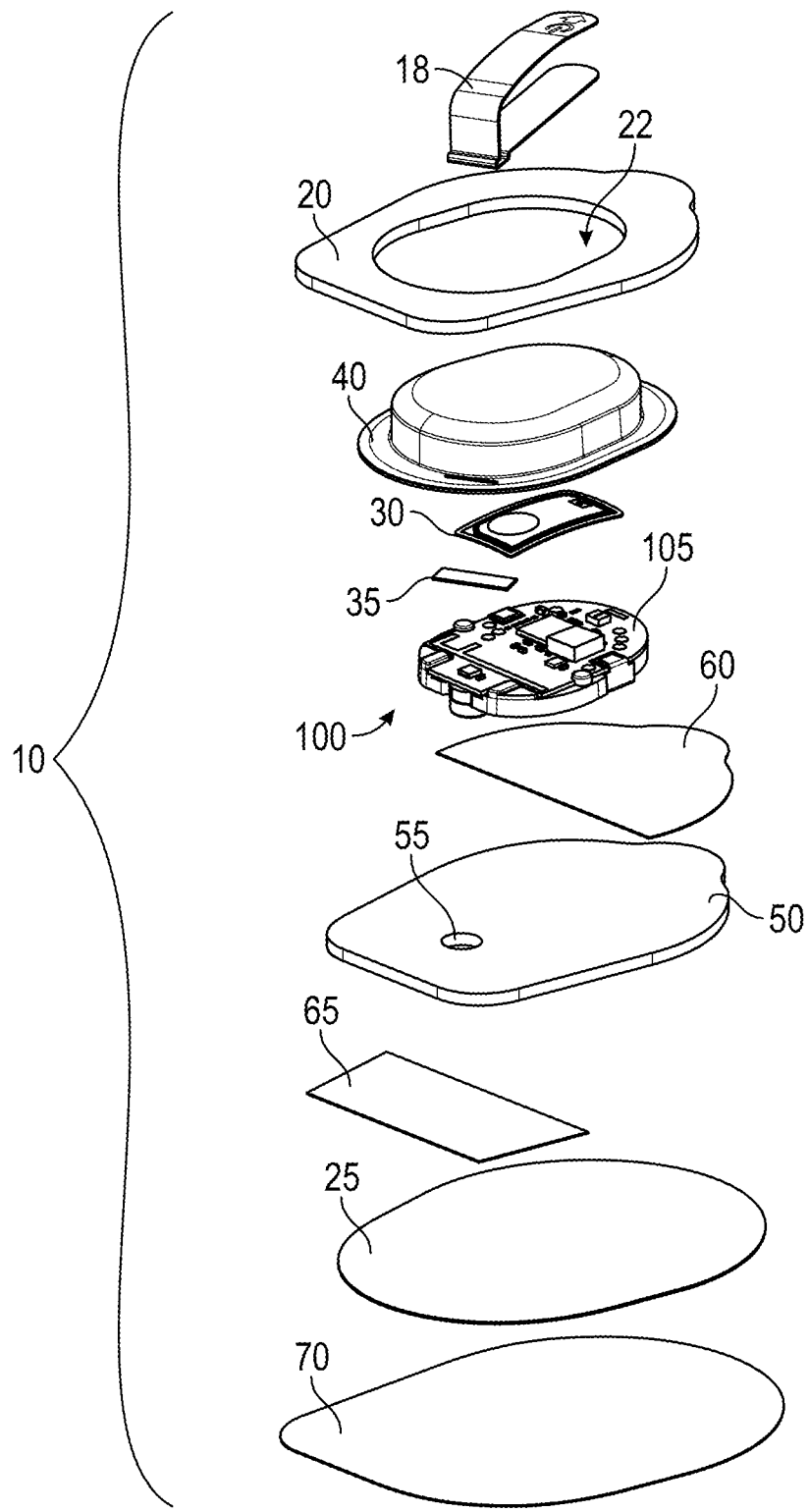
FIGS. 3A and 3B illustrate top and bottom exploded perspective views of the wearable device of FIG. 1 in accordance with aspects of this disclosure.
Figure 3B:
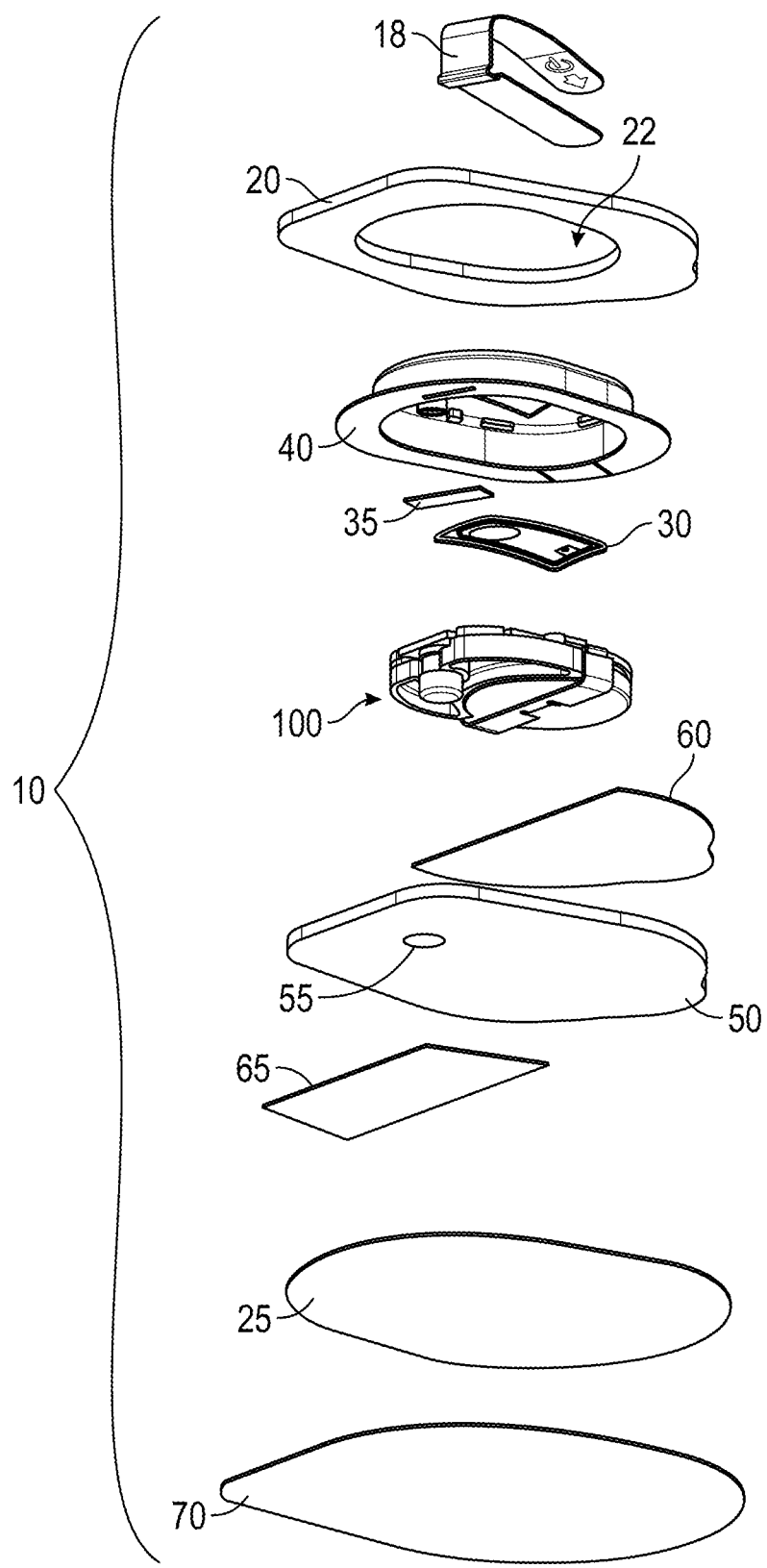

FIGS. 3A-3B illustrate exploded perspective views of the wearable device 10. FIGS. 2A-2H illustrate various views of the wearable device 10 without a battery isolator 18 (see FIGS. 3A-3B) attached to better illustrate aspects of the wearable device 10.

Figure 2I:
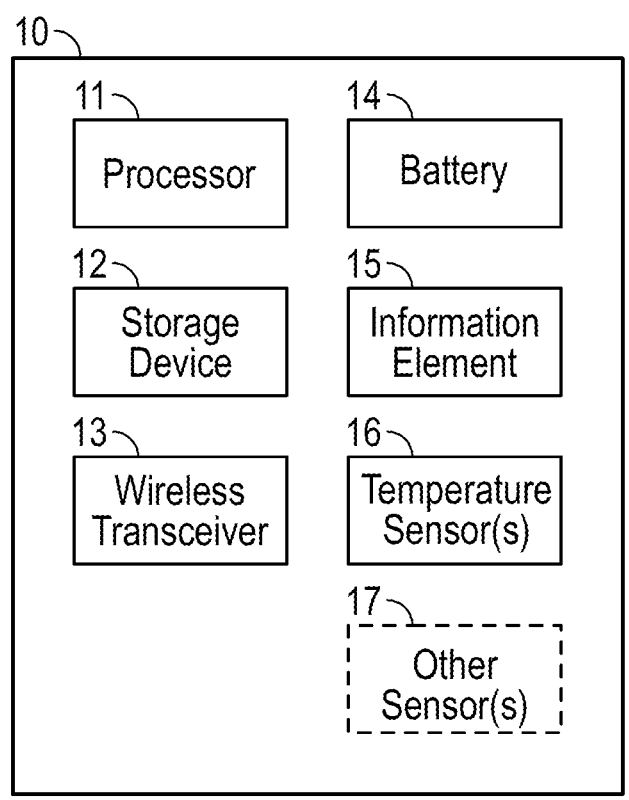
FIG. 2I illustrates a schematic block diagram of the wearable device of FIG. 1 in accordance with aspects of this disclosure.

FIG. 2I illustrates an exemplary schematic block diagram of the wearable device 10. As shown, the wearable device 10 can include a processor 11, a storage device 12, a wireless transceiver 13, a battery 14, an information element 15, and/or one or more temperature sensors 16. The processor 11 can be configured, among other things, to process data, execute instructions to perform one or more functions, and/or control the operation of the wearable device 10. For example, the processor 11 can process physiological data obtained from the wearable device 10 and can execute instructions to perform functions related to storing and/or transmitting such physiological data. For example, the processor 11 can process data received from one or more temperature sensors 16 and/or one or more other physiological parameter sensors 17 and can execute instructions to perform functions related to storing and/or transmitting such received data.

The storage device 12 can include one or more memory devices that store data, including without limitation, dynamic and/or static random access memory (RAM), programmable read-only memory (PROM), erasable programmable read-only memory (EPROM), electrically erasable programmable read-only memory (EEPROM), and the like. Such stored data can be processed and/or unprocessed physiological data obtained from the wearable device 10, for example. The wireless transceiver 13 can be configured to allow the wearable device 10 to wirelessly communicate with other devices, systems, and/or networks over a communication protocol. The wireless transceiver 13 can be configured to use any of a variety of wireless communication protocols, such as Wi-Fi (802.11x), Bluetooth®, Zig-Bee®, Z-wave®, cellular telephony, infrared, RFID, satellite transmission, proprietary protocols, combinations of the same, and the like.

The wearable device 10 can include a battery 14. The battery 14 can provide power for the hardware components of the wearable device 10 described herein. The battery 14 can be, for example, battery 110, described in more detail below. The battery 14 can be, for example, a lithium battery. Additionally or alternatively, the wearable device 10 can be configured to obtain power from a power source that is external to the wearable device 10. For example, the wearable device 10 can include or can be configured to connect to a cable which can itself connect to an external power source to provide power to the wearable device 10.

The wearable device 10 can include an information element 15. The information element 15 can be a memory storage element that stores, in non-volatile memory, information used to help maintain a standard of quality associated with the wearable device 10. Illustratively, the information element 15 can store information regarding whether the wearable device 10 has been previously activated and whether the wearable device 10 has been previously operational for a prolonged period of time, such as, for example, four hours. The information stored in the information element 15 can be used to help detect improper re-use of the wearable device 10, for example.

As shown in FIG. 2I, the wearable device 10 can include one or more temperature sensors 16 that can continuously or periodically obtain temperature data of the subject. Advantageously, in some implementations, the processor 11 can compare temperature data from more than one temperature sensor 16 to more accurately determine core body temperature of the subject. In some variants, the wearable device 10 includes one or more temperature sensors 16 and also includes one or more other sensors 17, such as one or more of an accelerometer, a gyroscope, a magnetometer, an oximetry sensor, a moisture sensor, an impedance sensor, an acoustic/respiration sensor, and/or an ECG sensor. In some variants, the wearable device 10 includes one or more temperature sensors 16 and does not include an accelerometer, a gyroscope, a magnetometer, an oximetry sensor, a moisture sensor, an impedance sensor, an acoustic/respiration sensor, or an ECG sensor, which can advantageously help conserve battery and processing power and preserve processing capabilities of the wearable device 10 where continuous or periodic core body temperature values are being determined and/or transmitted. In some variants, the only type of physiological parameter measured and/or monitored by the wearable device 10 is body temperature. The one or more temperature sensors 16 can be, for example, any of temperature sensors 150a, 150b, 150c, each of which are discussed in more detail below.

The processor 11 of the wearable device 10 can be configured to process obtained physiological information. For example, the processor 11 can be configured to determine a core body temperature of a user based on thermal energy obtained by one or more temperature sensors 16 of the wearable device 10. The wireless transceiver 13 can be configured to wirelessly transmit the processed physiological information (and/or unprocessed physiological information) to a separate computing device, such as a patient monitor, a mobile device (for example, an iOS or Android enabled smartphone, tablet, laptop), a server or other computing or processing device for display and/or further processing, among other things. The computing device can be configured to store and/or further process the received physiological information, to display information indicative of or derived from the received physiological information, and/or to transmit information—including displays, alarms, alerts, and notifications—to computing devices or systems including a patient monitoring system associated with a hospital, a caregiver (for example, a primary provider), or a user (for example, an employer, a school, friends, family) that have permission to access the subject's (for example, patient's) data. As another example, the wireless transceiver 13 of the wearable device 10 can be configured to wirelessly transmit processed or unprocessed obtained physiological information to a mobile phone which can include one or more hardware processors configured to execute an application that generates a graphical user interface displaying information representative of the processed or unprocessed physiological information obtained from the wearable device 10. In some variants, the wearable device 10 is configured to measure and/or monitor only one type of physiological parameter, that being body temperature.

FIGS. 3A and 3B illustrate exploded views of the wearable device 10. The wearable device 10 can include a housing 40 and one or more substrates, such as one or more of substrates 20, 25, 50, 60, 65, 70, which are described in more detail below. As discussed above, the wearable device 10 can include a processor 11, storage device 12, wireless transceiver 13, battery 14, information element 15, and/or one or more temperature sensors 16. The processor 11, storage device 12, wireless transceiver 13, battery 14, information element 15, and/or one or more temperature sensors 16 can be mounted and/or coupled with a circuit layer of the wearable device 10. The circuit layer can be enclosed or at least partially enclosed by the housing 40 (and/or a portion of the housing 40) and/or one or more of substrates 20, 25, 50, 60, 65, 70. The circuit layer can be positioned between or at least partially between the housing 40 (or a portion of the housing 40) and one or more of the substrates of the wearable device 10, such as any of substrates 20, 25, 50, 60, 65, 70. The circuit layer can be, for example, a circuit board, such as circuit board 105 which is illustrated in at least FIGS. 3A-3B, 5A-5D, 7, and 8A-8D. The circuit board 105 can be a printed circuit board, for example. The battery 14 can be, for example, the battery 110 shown in at least FIGS. 5A-5D and 8A-8D and described elsewhere herein. As shown and as discussed further below, the battery 110 can be mechanically and/or electronically coupled with the circuit board 105, for example, via the battery holder 115.

The wearable device 10 can include a probe that acts as a conduit to transmit thermal energy from the subject to and/or toward one or more temperature sensors 16 of the wearable device 10. The probe can be rigid or flexible. The probe can comprise thermally conductive material. For example, the probe can comprise a metallic material, such as aluminum. The probe can be the probe 140 or the probe 240 which are discussed in more detail below.

The wearable device 10 can include a mounting frame that secures one or more components of the wearable device 10 to the housing 40. The mounting frame can be, for example, mounting frame 130 shown in at least FIGS. 5A-5D and 8A-8D and further discussed below. The mounting frame 130 can secure the circuit board 105 and/or the probe 140 (or probe 240) to the housing 40 and/or to one or more of substrates 20, 25, 50, 60, 65, 70. Where the battery 110 is coupled with the circuit board 105 via the battery holder 115 as described below, the mounting frame 130 can secure the circuit board 105, battery holder 115, and the battery 110 to the housing 40 and/or to one or more of substrates 20, 25, 50, 60, 65, 70.

With reference to FIGS. 3A-3B and 5A-5D, the circuit board 105, the probe 140, the mounting frame 130, the battery 110, the battery holder 115, and/or one or more temperature sensors coupled to the circuit board 105 (such as temperature sensors 150a, 150b) can form an electronics assembly of the wearable device 10, which is generally represented by the numeral "100" in FIGS. 3A-3B. The electronics assembly 100, and any or all of the above-listed components that can form the electronics assembly 100, can be enclosed (or partially enclosed) by the housing 40 (or a portion thereof) and one or more of substrates 20, 25, 50, 60, 65, 70. The electronics assembly 100, and any or all of the above-listed components that can form the electronics assembly 100, can be positioned between or at least partially between the housing 40 (or a portion of the housing 40) and one or more of substrates 20, 25, 50, 60, 65, 70. The use of the phrase "electronics assembly" or the reference numeral "100" in the present disclosure is not intended to be limiting, but rather, is merely intended as a convenient method to refer to one or more components of the wearable device 10 which can be enclosed by the housing 40 and/or one or more of substrates 70, 25, 65, 50, 65, and/or 20.

As discussed above, the wearable device 10 can be configured to wirelessly communicate with a separate computing device. For example, the wearable device 10 can be configured to wirelessly transmit and/or receive information from a separate computing device. As another example, the wearable device 10 can be configured to wirelessly transmit processed and/or unprocessed physiological information obtained by the wearable device 10. As discussed above, the wearable device 10 can include a wireless transceiver 13. The wireless transceiver 13 can be coupled with (for example, mounted on a surface of) the circuit board 105. As discussed above, the wireless transceiver 13 can be configured to use any of a variety of wireless protocols, such as Wi-Fi (802.11x), Bluetooth®, ZigBee®, Z-wave®, cellular telephony, infrared, RFID, satellite transmission, proprietary protocols, combinations of the same, and the like.

The wearable device 10 can include near field communication (NFC) functional capabilities (for example, RFID) that can enable the wearable device 10 to interact and/or communicate with separate computing devices. Such NFC functional capabilities can enable the wearable device 10 to, among other things: confirm or verify that it is and/or is made up of authentic components; transfer data (for example, physiological data obtained by wearable device 10; and determine a lifespan of the wearable device 10. The wearable device 10 can include an RFID tag (for example, in the form of a sticker, label, layer, and/or inlay) that can interact with an RFID reader of a separate computing device that emits a radio frequency. For example, with reference to FIGS. 3A-3B, the wearable device 10 can include a NFC tag 30 that can communicate and/or interact with an NFC reader of a separate computing device. The NFC tag 30 can comprise a layer or inlay that can be secured to a portion of the wearable device 10. For example, as discussed in more detail below, the NFC tag 30 can be secured to a portion of the housing 40, such as to an interior surface of the housing 40. The NFC tag 30 can be secured to a portion of the housing 40 such that, when the wearable device 10 is assembled (as shown in FIGS. 1-2H), the NFC tag 30 is positioned at or near a top portion of the wearable device 10, such as a top portion 41a of the housing 40 which is discussed below. Such positioning can advantageously facilitate communication between the NFC tag 30 and an NFC reader of a separate computing device when brought in proximity to each other. The NFC tag 30 can be an active or passive RFID tag, for example. The NFC tag 30 can allow an NFC reader of a separate device to register, track, and/or determine information about the wearable device 10 such as date and/or location of manufacture, among other things.

Figure 4A:
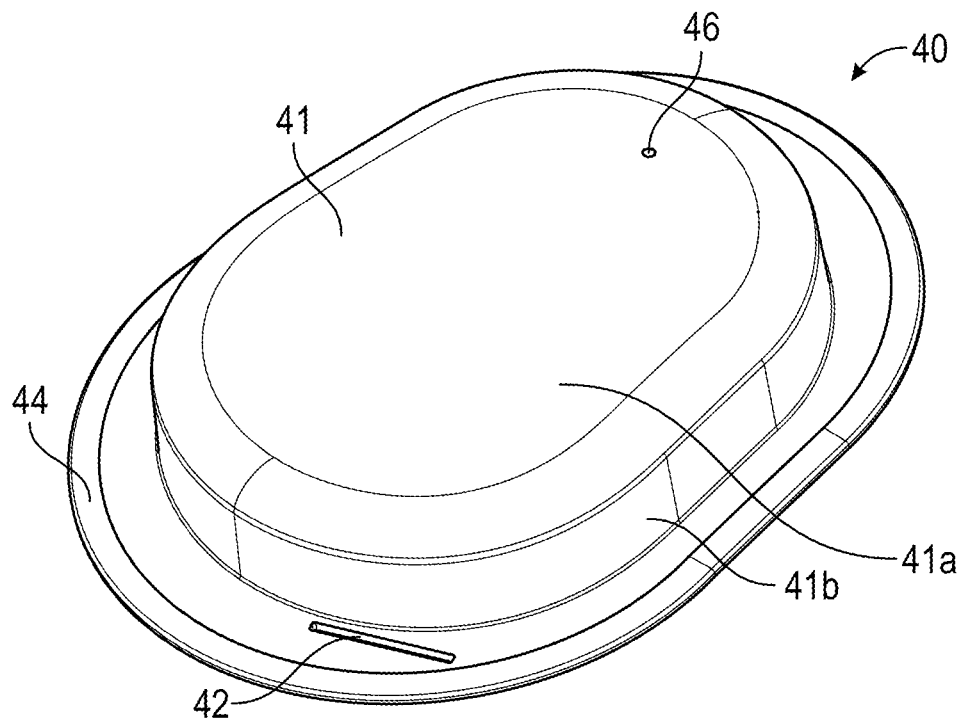
FIGS. 4A and 4B illustrate top and bottom perspective views of a housing of the wearable device of FIG. 1 in accordance with aspects of this disclosure.
Figure 4B:
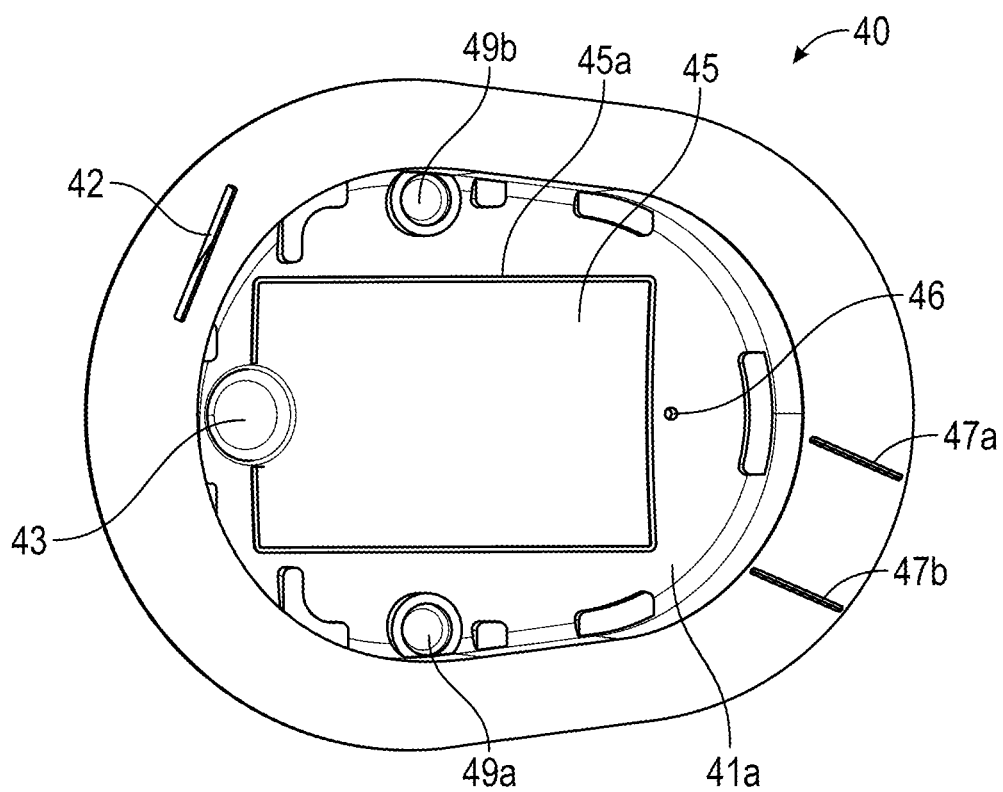
Figure 5A:
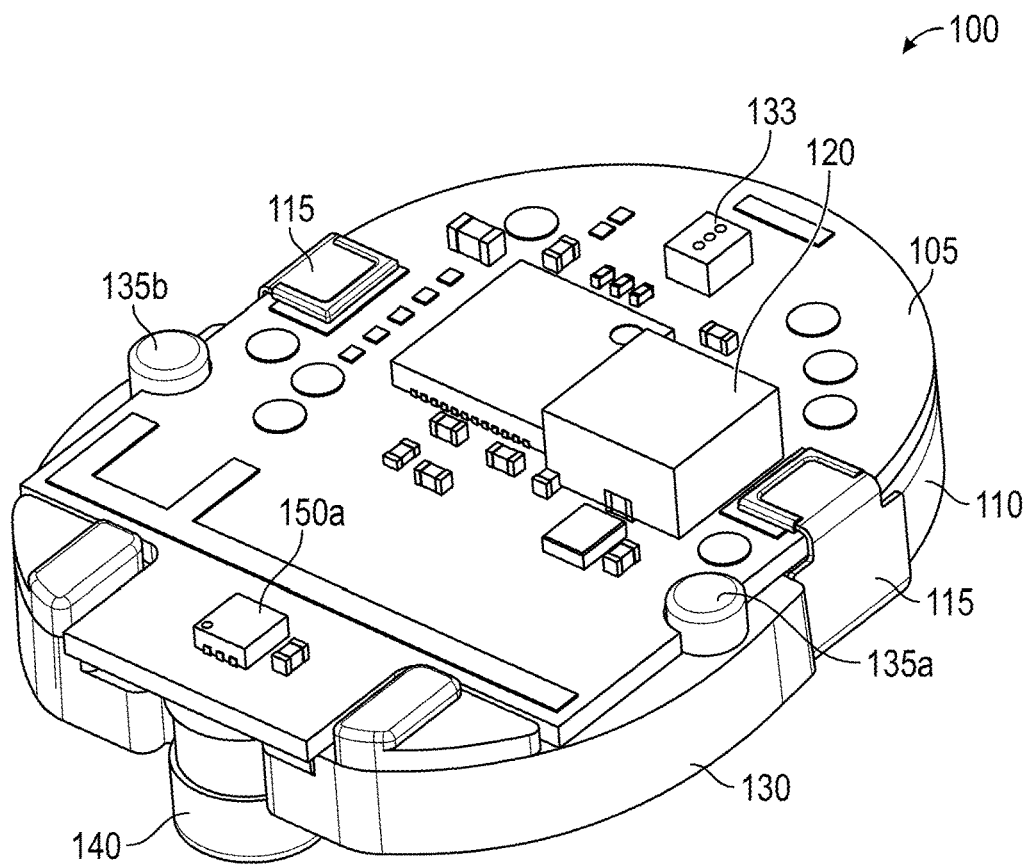
FIGS. 5A and 5B illustrate top and bottom perspective views of a portion of the wearable device of FIG. 1 in accordance with aspects of this disclosure.
Figure 5B:
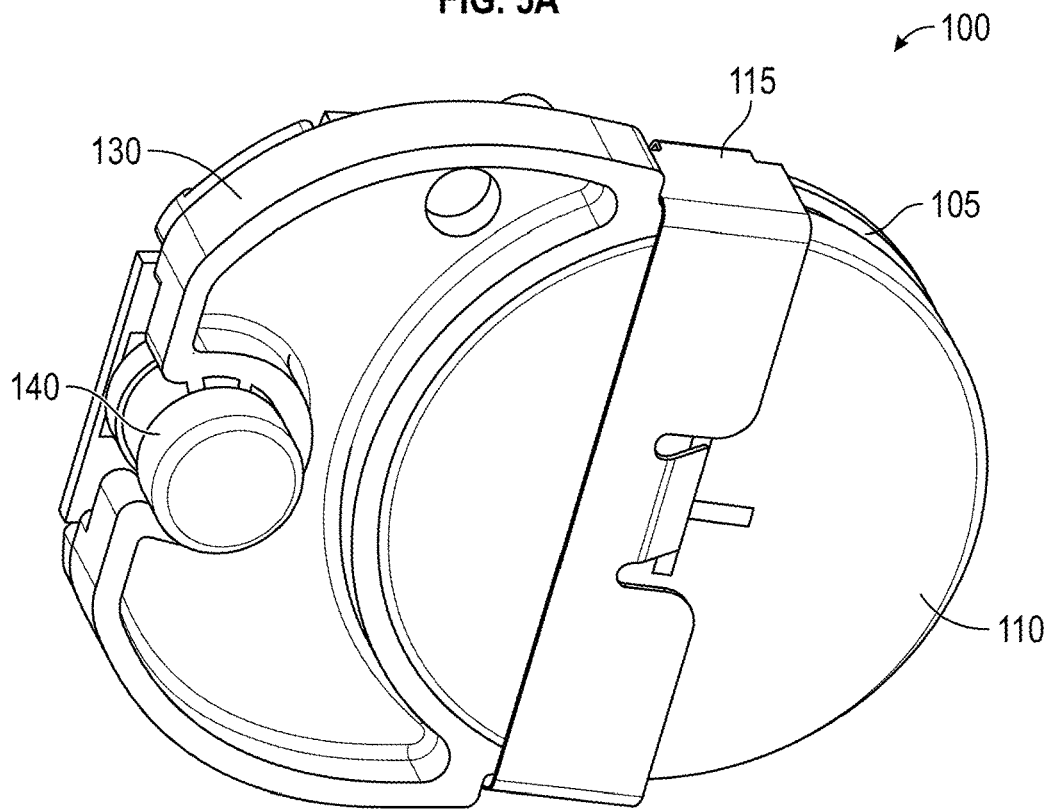

The wearable device 10 can include a battery isolator that can block electrical communication between the battery 110 and one or more electrical contacts on the circuit board 105. For example, as shown in FIGS. 3A-3B, the wearable device 10 can include battery isolator 18 (which can also be referred to as a "battery isolator tab"). The battery isolator 18 can be used to preserve battery power until the wearable device 10 is ready for use. The battery isolator 18 can be configured to block electrical connection between the battery 110 and the circuit board 105 until the battery isolator 18 is removed from the wearable device 10. The battery isolator 18 can be made of any material that possesses adequate flexibility to be slidably removed from its initial position and adequate dielectric properties so as to electrically isolate the battery 110 (or a portion thereof) from the circuit board 105. For example, the battery isolator 18 can be made of plastic, polymer film, paper, foam, combinations of such materials, or the like. The battery isolator 18 can extend through a slot of the housing 40 when the wearable device 10 is assembled. For example, the battery isolator 18 can extend through slot 42 of housing 40 discussed below with reference to FIGS. 4A-4B. With reference to FIGS. 3A-3B and FIG. 5B, an end of the battery isolator 18 can be positioned between an electrical contact on a bottom surface of the battery 110 and a portion of the battery holder 115 which is electrically connected to the circuit board 105. Such positioning can allow the battery isolator 18 to block electrical communication between the battery 110 and the circuit board 105. In some variants, the battery isolator 18 is textured (for example, at or near an end thereof that is external to the housing 40) to provide a frictional surface to aid a user in gripping and sliding the battery isolator 18 out of its original assembled position. Once the battery isolator 18 is removed, electrical communication between the battery 110 and the circuit board 105 can be initiated to energize the electronic components of the wearable device 10.

With reference to FIGS. 3A-3B and 4A-4B, the battery isolator 18 can be secured (for example, partially secured) to a portion of the housing 40 with a securement tab 35 (see FIGS. 3A-3B). For example, the securement tab 35 can secure a portion of the battery isolator 18 to a rim 44 of the housing 40 (see FIGS. 4A-4B), and/or can position the battery isolator 18 with respect to the housing 40. The battery isolator 18 can be inserted through a slot of the housing 40 (such as slot 42 extending through a rim 44 of the housing 40). The securement tab 35 can secure a portion of the battery isolator 18 to the rim 44 of the housing 40 proximate the slot 42. For example, the securement tab 35 can secure the battery isolator 18 to the rim 44 over and/or around the slot 42. The securement tab 35 can be and/or comprise, for example, an adhesive tape on one or more sides of the securement tab 35. The securement tab 35 can keep at least a portion of the battery isolator 18 in place (for example, stationary) with respect to the housing 40 until a sufficient force is applied to the battery isolator 18 which causes the securement tab 35 and/or the portion of the battery isolator 18 secured to the housing 40 by the securement tab 35 to "break free" (for example, move). The securement tab 35 can aid in maintaining a position of ends of the battery isolator 18 relative to the wearable device 10. For example, the securement tab 35 can advantageously help maintain a position of a first end of the battery isolator 18 in between the battery 110 and a portion of the battery holder 115 in electrical communication with the circuit board 105 and/or help maintain a position of a second end of the battery isolator 18 external to the housing 40 to facilitate visibility and/or grasping by a user.

The wearable device 10 can include one or more substrates that can secure and/or secure to other portions of the wearable device 10 and/or that can allow the wearable device 10 to secure to a subject (for example, skin of the subject). For example, with reference to FIGS. 3A-3B, the wearable device 10 can include one or more of substrates 20, 50, 60, 65, 25, and/or 70.

Substrate 20 can be configured to surround a portion of the housing 40. For example, substrate 20 can include an opening 22 through which the housing 40 fits during assembly. The opening 22 can be sized and/or shaped to match a size and/or shape of a portion of the housing 40. For example, the opening 22 can be sized and/or shaped to match a size and/or shape of a main body 41 of the housing 40 which can be interior to and/or within the rim 44 of the housing 40. Substrate 50 can be positioned adjacent (for example, underneath) the housing 40 (or a portion thereof) and/or between the substrate 25 and the housing 40 (or a portion thereof). The substrates 20, 50 can sandwich a portion of the housing 40 therebetween. For example, when the wearable device 10 is assembled, the substrates 20, 50 can sandwich the rim 44 of the housing 40. Such configuration can secure the housing 40 (and other components of the wearable device 10 that are directly or indirectly connected to the housing 40) to the substrates 20, 50 and any other of the substrates 70, 25, 65, and/or 60 which can be incorporated in the wearable device 10. As illustrated in FIG. 3A, the substrates 20, 50 can have substantially similar shapes. For example, substrates 20, 50 can have substantially matching perimeters. Substrates 20, 50 can be made of foam material such as white polyethylene, polyurethane, or reticulated polyurethane foams, to name a few. Substrates 20, 50 can be made of medical-grade foam material.

With reference to FIGS. 3A-3B and 5A-5B, substrate 50 can include an opening 55 sized and/or shaped to match a size and/or shape of the probe 140, or probe 240. For example, the opening 55 can have a size and/or shape that matches a size and/or shape of a perimeter of a cross-section of the probe 140 (or a portion of the probe 140), or probe 240 (or a portion of the probe 240). As discussed further below, this can advantageously allow a portion of the probe 140 (or probe 240) to extend through at least a portion of the opening 55 and be in closer proximity to a portion of the subject's skin surface when the wearable device 10 is in use, which can allow the probe 140 (or probe 240) to transmit thermal energy from the subject near, to, and/or toward one or more temperature sensors of the wearable device 10 (for example, temperature sensors 150a and/or 150c). The opening 55 can allow the probe 140 (or a portion of the probe 140), or probe 240 (or a portion of the probe 240) to extend through the opening 55 to contact (directly or indirectly via substrate 25) and/or apply pressure to a portion of the subject's skin surface, which can also increase thermal transmissibility. Opening 55 can extend through a thickness of substrate 50 and/or can extend between opposing surfaces of the substrate 50 (for example, top and bottom surfaces of the substrate 50). Opening 55 can be spaced from a perimeter of the substrate 50. Substrate 50 can include a first end, a second end opposite the first end, and first and second sides extending between the first and second ends and opposite one another. In such configurations, opening 55 can be positioned closer to one of the first or second ends and/or can be positioned equidistantly or non-equidistantly from the first and second sides.

Any of the above mentioned substrates 20, 60, 50, 65, 25 can be integrally formed with one or more of each other. For example, in some variants, substrate 25 (described above) is integrally formed with substrate 50, substrate 60, and/or substrate 65. In some variants, wearable device 10 does not include substrate 65 and/or substrate 60. In some variants, wearable device 10 does not include a substrate 25 but rather includes a substrate 50 that can include the features and/or characteristics described above with respect to substrate 25 (for example, substrate 50 can be configured to secure (e.g., adhere) to skin of a user).

The wearable device 10 can include a substrate configured to contact the subject and/or help secure (for example, removably secure) the wearable device 10 (or portions thereof) to the subject. For example, with reference to FIGS. 3A-3B, the wearable device 10 can include a substrate 25 that can contact and/or secure to skin of a subject when the wearable device 10 is in use. Substrate 25 can be a bottom-most one of the one or more substrates (and/or of the wearable device 10) when the wearable device 10 is in use (for example, after the release liner 70 is removed). Substrate 25 can be or include a material configured to secure to skin of a user. Substrate 25 can comprise a material configured to allow for removable securement of the wearable device 10 to the user's skin. For example, the substrate 25 can be coated with a high tack, medical-grade adhesive, which when in contact with the subject's skin, is suitable for long-term monitoring, such as, for example two days or longer, such as 3 days, 4 days, 5 days, 6 days, 7 days, 8 days, 9 days, or 10 days or longer. Additionally or alternatively, the substrate 25 can be or include a soft, comfortable, and/or breathable material. For example, substrate 25 can be or include fabric, such as non-woven fabric having holes or openings. The substrate 25 can be fabric and include an adhesive material or layer (such as adhesive tape) on one or both surfaces of the substrate 25. Such configuration can allow the wearable device 10 to comfortably secure to the user's skin.

The wearable device 10 can include a substrate that is a release liner 70. The release liner 70 can secure to one or more of the above-described substrates (such as substrate 25) and can be removed prior to securement of the wearable device 10 to a user. For example, release liner 70 can be removed from the substrate 25 prior to placement and/or securement of the wearable device 10 on the subject's skin.

As discussed above, the wearable device 10 can include a wireless transceiver 13 that can transmit data to (and/or receive data from) a separate device over a wireless communication protocol. Advantageously, the wearable device 10 can include one or more substrates positioned between the wireless transceiver 13 (and/or the circuit board 105) and the subject's skin (when the device 10 is in use) that reflect wireless signal(s) transmitted from the wireless transceiver 13 away from the subject's skin. Such configuration can, among other things, help to amplify the emitted signal (for example, in a direction away from the subject's skin), which may be important especially where the wireless communication protocol utilizes a relatively short range (for example, Bluetooth® wireless communication protocols).

For example, with reference to FIGS. 3A-3B, the wearable device 10 can include a substrate 60 that is configured to reflect such wireless signal(s) transmitted from the wireless transceiver 13 away from the subject's skin. Substrate 60 can be positioned between the circuit board 105 (and a wireless transceiver mounted to the circuit board 105) and substrate 50. Substrate 60 can be positioned between the circuit board 105 (and a wireless transceiver mounted to the circuit board 105) and any of substrates 50, 25, 65, and/or the release liner 70. Substrate 60 can be adhered to a surface of substrate 50 and/or one or more of the battery 110, the battery holder 115, and/or the mounting frame 130 (see FIGS. 3B and 5B). With reference to FIGS. 3A-3B, in some variants, the substrate 60 is sized and/or shaped to not cover the opening 55 in the substrate 50, which can allow the probe 140 (or probe 240) to extend through the opening 44. Substrate 60 can be a polypropylene film, such as a metalized propylene film, that is configured to reflect wireless signals (for example, transmitted over Bluetooth® wireless communication protocol) away from the subject's skin when the wearable device 10 is in use.

The wearable device 10 can include a substrate 65 positioned between a surface of substrate 25 (or a portion of a surface of substrate 25) and a surface of the substrate 50 (or a portion of a surface of the substrate 50). For example, the substrate 65 can be positioned between the opening 55 in the substrate 50 and a surface of the substrate 25. The substrate 65 can include an adhesive material configured to secure the substrate 50 (or a portion thereof) to the substrate 25 (or a portion thereof). Substrate 65 can be, for example a polypropylene film. Substrate 65 can cover the opening 55 when secured to substrate 50. When an end (for example, bottom end) of the probe 140 (or probe 240) extends through the opening 55 of the substrate 50, the substrate 65 can cover the end of the probe 140 (or probe 240) and/or "bulge" at and/or around the end, for example, as shown in FIG. 7. Substrate 65 can advantageously cover opening 55 and prevent ingress of fluid (for example, sweat) through opening 55 and toward electrical components (for example, the circuit board 105) of the wearable device 10 when in use. Such configuration is especially beneficial where substrate 25 is permeable (for example, a fabric material) and sweat from the subject's skin is present around the perimeter of the probe 140 near the opening 55.

One or more of substrates 60, 65, 25, or 70 can be transparent or semi-transparent. For example, FIG. 2D illustrates substrates 70, 25, 65 as being transparent such that probe 140 can be seen in FIG. 2D. However, any or all of substrates 60, 65, 25, or 70 can be not transparent.

Any or all of substrates 25, 50, 20 can be made of a material that can provide thermal insulation and/or provide thermal conductivity. For example, when the wearable device 10 is positioned on and/or secured to (for example, adhered to) a subject's skin surface, one or more of the substrates 25, 50, 20 can act to insulate the skin surface at, around, and/or proximate to a point or region where temperature is measured and/or where thermal energy is transmitted from the skin surface of the subject to or near one or more temperature sensors of the wearable device 10. For example, when the wearable device 10 is positioned on and/or secured to (for example, adhered to) a subject's skin surface, the substrates 25, 50, 20 can insulate the skin surface around the opening 55 and/or around the probe 140 (or probe 240) which can act as a conduit for thermal energy to flow from the skin surface to and/or toward one or more temperature sensors of the wearable device 10 (such as temperature sensor 150a). In the human body, there is a natural heat flux between the body core and the skin surface because the body core temperature is typically at a higher temperature than that of the skin surface. Thus, heat flows from the body core to the skin. By insulating the skin surface at and around the opening 55 and/or the probe 140 (or probe 240)—thereby preventing heat from escaping—the temperature gradient between the body core and the skin surface will decrease. The skin temperature, under the insulated area will rise until it reaches equilibrium with the warmest region (i.e., the body core) underneath the insulation, thereby approaching the body core temperature. When equilibrium is reached, the skin temperature is equal to the body core temperature. One or more of substrates 25, 50, 20, which can be in direct or indirect contact with the subject's skin around the opening 55, probe 140 (or probe 240), and/or one or more temperature sensors of the wearable device 10, can possess thermal insulation properties. In some configurations, the substrates 20 and/or 50 are made of thermally insulating materials including polyurethane foam, polystyrene foam, neoprene foam, neoprene rubber, polyester (Mylar), polytetrafluoroethylene (PTFE), silicone foam, silicone rubber, or the like, and the substrate 25 is made of a fabric having an adhesive material configured to secure to a subject's skin.

As discussed above and as shown in at least FIGS. 3A-3B, the wearable device 10 can include a housing 40 which can enclose, house, and/or protect various components of the wearable device 10. FIGS. 4A and 4B illustrate top and bottom views of the housing 40, respectively. The housing 40 can be made of any material that is capable of adequately protecting the electronic components of the wearable device 10. The housing 40 can be rigid or alternatively, flexible. The housing 40 can be made of and/or include thermoplastics and/or thermosetting polymers. With reference to FIG. 4A, the housing 40 can have a main body 41 that can include (and/or that can be defined by) a top portion 41a and one or more walls (or a single, continuous wall) 41b extending outward from the top portion 41a and/or around a perimeter of the top portion 41a (or a portion of a perimeter of the top portion 41a). The main body 41 can include a height that can be defined by a height of the wall(s) 41b. As discussed above, a portion of the housing 40 can be positioned within and/or extend through the opening 22 of the substrate 20. For example, the main body 41 can be positioned within and/or can extend through the opening 22. The main body 41 can be sized and/or shaped to be received in and/or through the opening 22 of the substrate 20. The main body 41 can be sized and/or shaped to create a tight fit when positioned within the opening 22 of the substrate 20.

As shown in FIGS. 4A-4B, the housing 40 can include a rim 44 extending around a portion of a perimeter of the main body 41. The rim 44 can extend around an entire perimeter of the main body 41 or a portion of the perimeter of the main body 41. The rim 44 can be connected to and/or can extend outward from the wall(s) 41b. The rim 44 can be used to secure the housing 40 in position relative to one or more substrates of the wearable device 10. For example, as discussed above the rim 44 can be positioned and/or sandwiched between the substrates 20, 50 when the wearable device 10 is assembled, which can allow the housing 40 to be secured to the substrates 20, 50 and/or any other substrates 60, 65, 25, and/or 70 discussed above.

The wearable device 10 can include one or more indicators configured to indicate a status of the wearable device 10, such as whether the wearable device 10 is in an operational ("on") mode, whether the wearable device 10 is pairing or has paired with a separate device, whether an error has been detected, and/or a power level of the wearable device 10. For example, with reference to at least FIG. 5A, the wearable device 10 can include an emitter 133 configured to emit light of one or more wavelengths to indicate a status of the wearable device 10. The emitter 133 can be coupled to the circuit board 105. The emitter 133 can include one or more light-emitting diodes (LEDs). The emitter 133 can emit light of certain colors to indicate certain statuses of the wearable device 10. For example, the emitter 133 can emit a green light to indicate that the wearable device 10 is powered "on" or a red light to indicate the wearable device 10 is "off". The housing 40 can be configured to allow light emitted from the emitter 133 to be visible from a location outside an interior of the housing 40. For example, the housing 40 (or a portion thereof such as the main body 41) can comprise a transparent or semi-transparent material that allows light emitted from the emitter 133 to be seen from a location outside an interior of the housing 40. Additionally or alternatively, the housing 40 can include an opening or hole that allows light emitted from the emitter 133 to pass through the housing 40. For example, as shown in FIGS. 4A-4B, the housing 40 can include a hole 46 that can allow light emitted from the emitter 133 to pass through the housing 40. The hole 46 can be located on the main body 41, for example, on the top portion 41a of the main body 41 of the housing 40. However, the hole 46 can be located in an alternative location, for example, on and/or along the wall(s) 41b of the housing 40. The hole 46 can be aligned with the emitter 133 to allow light emitted from the emitter 133 to more easily pass through the housing 40. For example, the hole 46 can be vertically aligned (or at least partially vertically aligned) with the emitter 133 so as to allow the light from the emitter 133 to pass through the housing 40.

As discussed previously, the housing 40 can include a slot through which the battery isolator 18 can be inserted during assembly. As shown in at least FIGS. 4A-4B, the slot 42 can be positioned on and/or can extend through the rim 44. However, the location of the slot 42 is not so limited. The slot 42 can be positioned on and/or can extend through a different portion of the housing 40, for example, the main body 41 or a portion thereof.

With reference to FIG. 4B, the housing 40 can include one or more features that can help secure, align, and/or position the housing 40 with respect to one or more other components of the wearable device 10. Such features can also assist assembly of the wearable device 10. For example, the housing 40 can include one or more features that can secure, align, and/or position the housing 40 with respect to the mounting frame 130 and/or circuit board 105. With reference to FIGS. 4B and 5A-6B, the housing 40 can comprise one or more cavities 49a, 49b configured to receive, retain, and/or secure one or more posts 135a, 135b of the mounting frame 130. The housing 40 can include one, both, or none of cavities 49a, 49b. The cavities 49a, 49b can be defined and/or formed by a wall having a cylindrical shape (see FIG. 4B), among other shapes. Such wall which can define and/or form the cavities 49a, 49b can extend from (for example, perpendicularly from) an interior surface of the top portion 41a of the housing 40. The cavities 49a, 49b can be positioned at or near the wall(s) 41b of the housing 40. The cavities 49a, 49b can be positioned at or near opposing walls 41b or other portions of the housing 40. The cavities 49a, 49b can be sized and/or shaped to receive, retain, and/or secure the one or more posts 135a, 135b of the mounting frame 130 so as to prevent movement of the mounting frame 130 (and/or other components coupled to the mounting frame 130 such as the circuit board 105 and/or the probe 140, 240) with respect to the housing 40 and/or the one or more substrates. The cavities 49a, 49b can be located opposite one another along portions of the housing 40, for example, at or near opposite sides of the housing 40 (and/or main body 41). While the figures illustrate the housing 40 having two cavities 49a, 49b, the housing 40 can have an alternative amount of cavities, such as less than or more than two cavities 49a, 49b. The number of cavities 49a, 49b can correspond with the number of posts 135a, 135b on the mounting frame 130.

With continued reference to FIG. 4B, the housing 40 can include a recess 43 (which can also be referred to as a "recessed portion"). The recess 43 can be located on a portion of the main body 41 of the housing 40, for example, on and/or along an interior surface of a top portion 41a of the main body 41. The recess 43 can align with one or more temperature sensors of the wearable device 10 that can be mounted to the circuit board 105. For example, with reference to FIGS. 3A-3B, 4B, 5A, and 7, the recess 43 can be aligned (for example, vertically aligned), with temperature sensor 150a. The recess 43 can advantageously provide more spacing and/or distance between the temperature sensor 150a and the housing 40 (such as the top portion 41a of the housing 40) to prevent the temperature sensor 150a from being influenced by a temperature of the housing 40 and/or by ambient temperature surrounding the housing 40 and/or wearable device 10. The recess 43 can be circular, among other shapes. The recess 43 can gradually transition from the interior surface of the top portion 41a of the main body 41 at, near, and/or around a perimeter the recess 43 (see FIGS. 4B and 7). With reference to FIG. 7, the recess 43 can be recessed a given depth $D_1$ from portions of the interior surface of the housing 40 (such as interior surface of the top portion 41a). The depth $D_1$ of the recess 43 can be less than a thickness $T_1$ of the housing 40 or a portion thereof (such as a thickness of the top portion 41a of the housing 40). The recess 43 can be larger than the temperature sensor 150a. For example, the recess 43 can have a width, length, and/or diameter that is larger than a width, length, and/or diameter of the temperature sensor 150a (see FIG. 7).

As discussed previously, the wearable device 10 can include an NFC tag 30 that can allow the wearable device 10 to interact with a separate computing device (such as an NFC reader of a separate device). As also discussed previously, the NFC tag 30 can be secured to a portion of the housing 40. With reference to FIG. 4B, the housing 40 can include an alignment feature 45 configured to align, position, retain, and/or secure the NFC tag 30. The alignment feature 45 can be located on an interior surface of the housing 40, such as on the top portion 41a of the main body 41. The alignment feature 45 can be formed by a protrusion 45a extending outward from an interior surface of the housing 40 (such as an interior surface of the top portion 41a of the housing 40) and extending continuously or intermittently along a portion of such interior surface. The protrusion 45a can have a height smaller than a height of the wall(s) 41b of the housing 40, for example. The alignment feature 45 can have a size and/or shape that matches a size and/or shape of the NFC tag 30. The alignment feature 45 can be configured to receive the NFC tag 30, for example, during assembly of the wearable device 10. The alignment feature 45 can comprise a rectangular shape where the NFC tag 30 comprises a rectangular shape. However, other shapes are possible for the alignment feature 45 and/or the NFC tag 30. The alignment feature 45 can comprise a protrusion 45a extending outward from and along an interior surface of the housing 40 in a rectangular shape. In some variants, the recess 43 interrupts a perimeter of the rectangular shape defined by the protrusions 45a.

The housing 40 can include one or more indicators configured to assist in the positioning and/or placement of the battery isolator 18 with respect to the housing 40 during assembly of the wearable device 10. For example, as shown in FIG. 4B, the housing 40 can include one or more of indicators 47a, 47b on the rim 44 of the housing 40. The indicators 47a, 47b can be straight and/or parallel lines and can be spaced apart from one another. During assembly, a portion of the battery isolator 18 can be placed through the slot 42 of the housing 40 and a width of the battery isolator 18 can be aligned with respect to a distance between the two indicators 47a, 47b. In some cases, the distance between the two indicators 47a, 47b can match a width of the battery isolator 18. In some cases, an end of the battery isolator 18 can be positioned between the two indicators 47a, 47b prior to removal of the battery isolator 18 from the housing 40 and/or wearable device 10. Such positioning can advantageously allow the battery isolator 18 to be properly positioned between an electrical contact of the battery 110 and the battery holder 115 which can be in electrical communication with the circuit board 105. For example, such positioning can ensure that a portion of the battery isolator 18 is positioned between a prong 115c of the battery holder 115 which can be in a middle portion of the battery holder 115 between two opposing arms 115a, 115b of the battery holder 115.

FIGS. 5A-5D show different views of a portion of the wearable device 10. As shown, the wearable device 10 can include a circuit board 105, a battery 110, a battery holder 115, a mounting frame 130, and a probe 140. The circuit board 105 can mechanically support and electrically connect various electrical components of the wearable device 10 to facilitate the performance of various functions of the wearable device 10. Such electrical components can include without limitation, the processor 11, storage device 12, wireless transceiver 13, and one or more temperature sensors 16 (such as temperature sensors 150a, 150b). The circuit board 105 can be double sided, having electronic components mounted on a first and/or second side or surface thereof. The circuit board 105 can include one or more electrical contacts 107 which can be electrically coupled (for example, soldered) to the battery holder 115 (or portions thereof). While the figures illustrate a circuit board 105 which can be, for example, a rigid circuit board (such as a rigid, printed circuit board), the wearable device 10 can alternatively include a flexible circuit that can electrically connect various electrical components of the wearable device 10.

The circuit board 105 or portions thereof can be sized and/or shaped to interact with the mounting frame 130. For example, the circuit board 105 or portions thereof can be sized and/or shaped to be secured to, be retained by, and/or be positioned by and/or with respect to, the mounting frame 130. As discussed in more detail below, a size and/or shape of an end 105a of the circuit board 105 can be configured to fit within a slot defined by one or more walls of the mounting frame 130. For example, the end 105a of the circuit board 105 can have a width that is sized to fit within a slot defined between walls 133c, 133d of the mounting frame 130. Additionally, as discussed further below, the circuit board 105 can include one or more openings 111 that are sized and/or shaped to receive the one or more posts 135a, 135b or portions thereof (such as a portion of a perimeter of the posts 135a, 135b). The openings 111 can be notches, for example, and can be positioned along sides or edges of the circuit board 105. The circuit board 105 can have an end 105a and an end 105b opposite the end 105a. As shown in at least FIGS. 5C-5D, the end 105b of the circuit board 105 can be curved. The curvature of the end 105b can match a curvature of a portion of the battery 110 and/or housing 40 (for example, the main body 41 of the housing), for example.

Figure 5C:
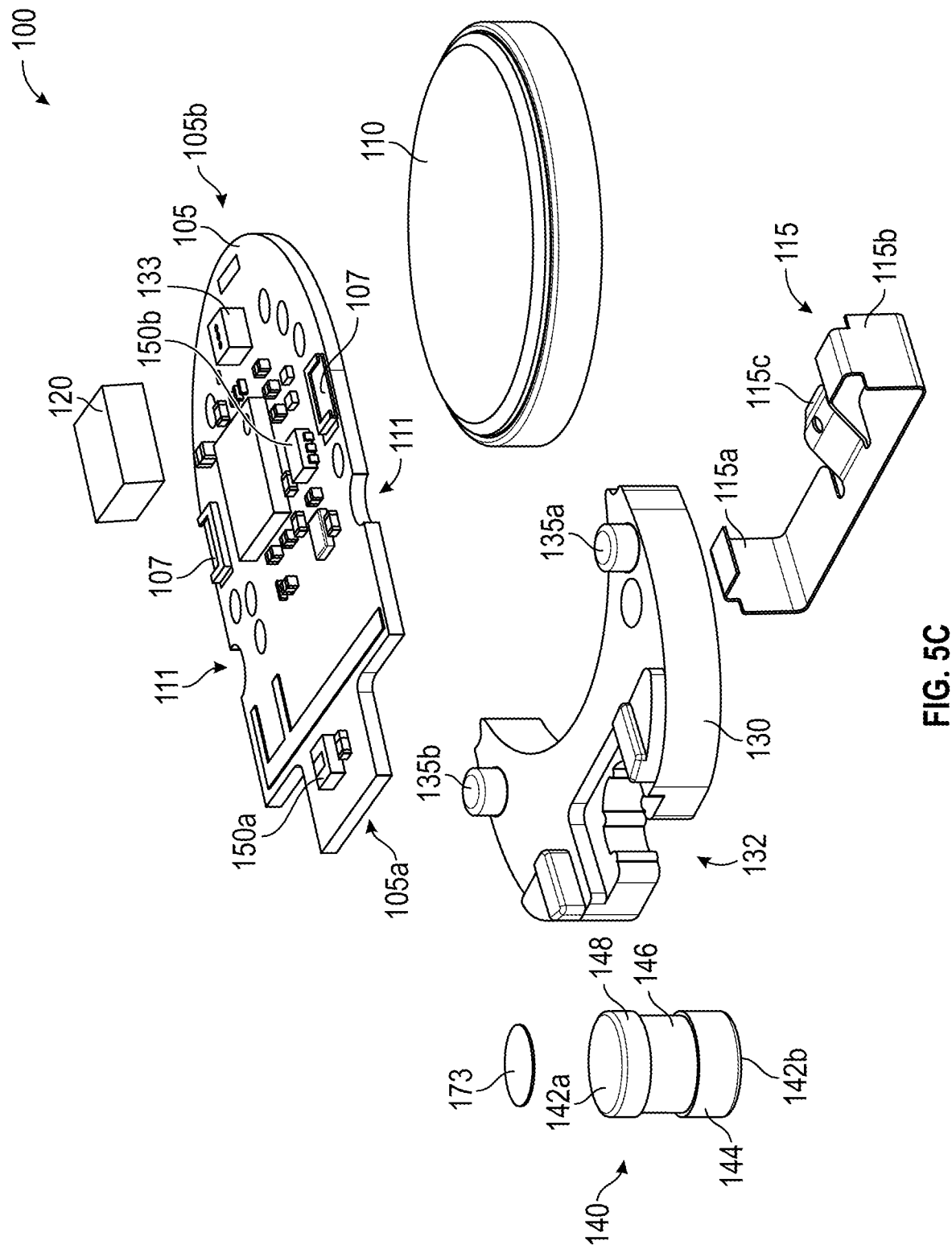
FIGS. 5C and 5D illustrate top and bottom exploded perspective views of the portion of the wearable device of FIGS. 5A and 5B in accordance with aspects of this disclosure.
Figure 5D:
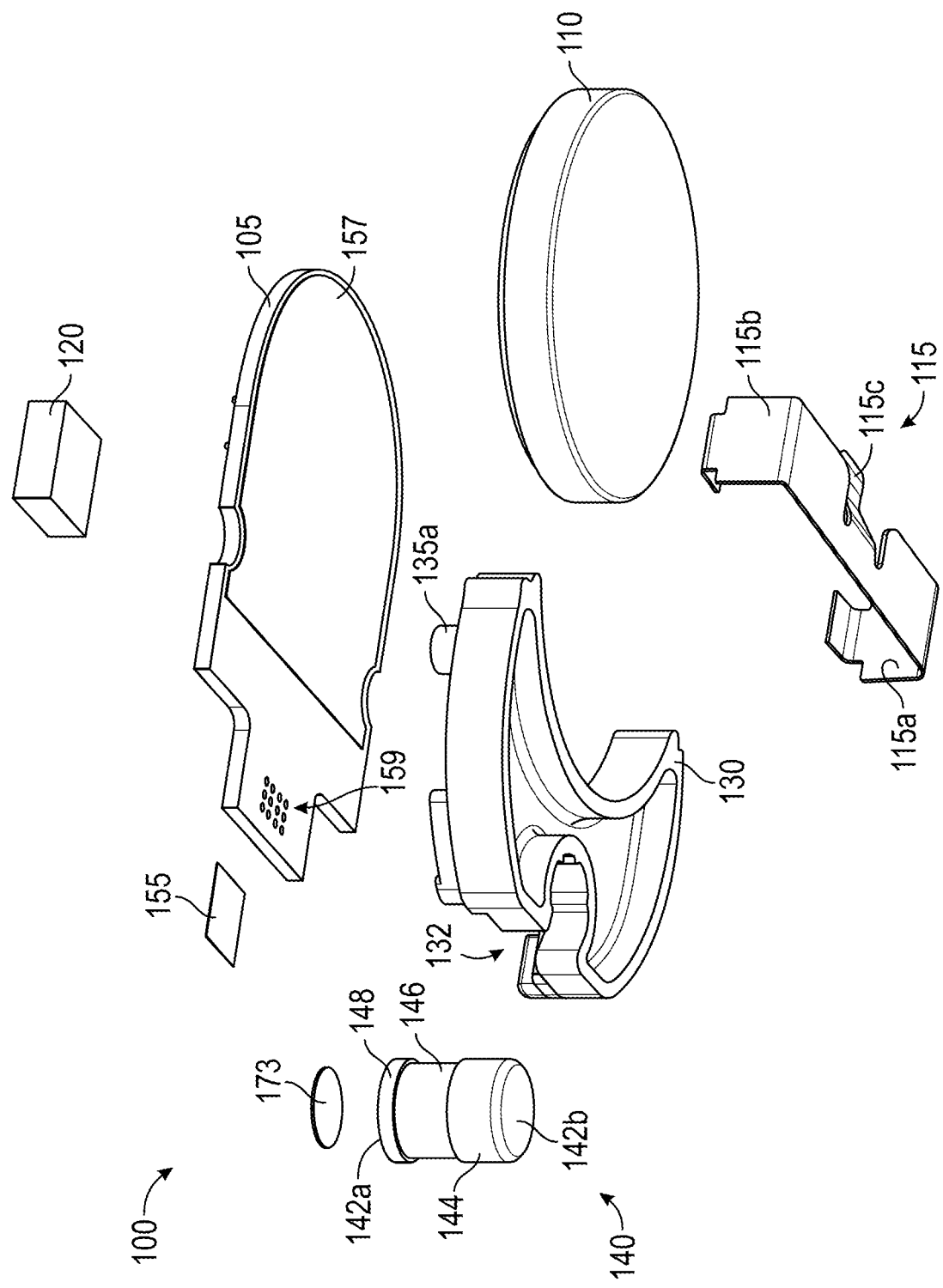

As illustrated in FIGS. 5A-5D, the battery holder 115 can be attached to electrical contacts 107 on two sides and/or edges of the circuit board 105. The battery holder 115 can form a support structure for the battery 110 and can hold the battery 110 in a stationary position relative to the circuit board 105. The battery holder 115 can be made of electrically conductive material. The battery 110 can provide power to the hardware components of the wearable device 10 which are described herein. The battery 110 can be a coin cell battery (such as a lithium coin cell battery). The battery 110 can have a cathode on a first (top) side and an anode on a second (bottom) side opposite the first side. As shown in at least FIG. 5C, the battery holder 115 can include two opposing arms 115a, 115b which can be electrically connected (for example, soldered) to electrical contacts 107 of the circuit board 105 and can also include a prong 115c that can contact the anode on the bottom side of the battery 110. The prong 115c can biased and/or can extend upward from a portion of the battery holder 115 so as to apply pressure to a portion of the battery 110 when the battery 110 is secured to the battery holder 115. During assembly and prior to use, the battery isolator 18 can be inserted between the anode of the battery 110 and the prong 115c to block electrical contact between the battery 110 and the circuit board 105. As shown in FIG. 5D, the circuit board 105 can include an electrical contact 157 configured to contact the cathode on the top side of the battery 110. The electrical contact 157 can be a gold plated copper pad.

Figure 6A:
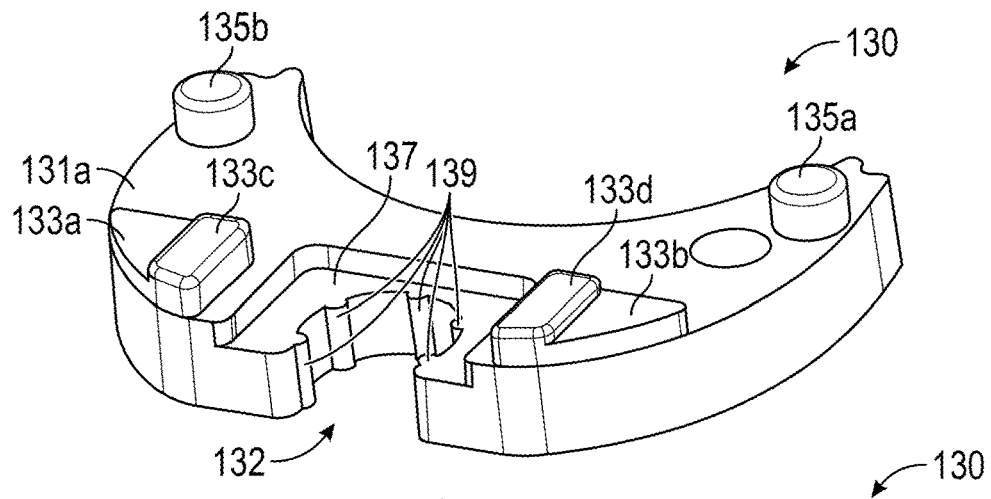
FIG. 6A illustrates a top perspective view of a mounting frame of the wearable device of FIG. 1 in accordance with aspects of this disclosure.
Figure 6B:
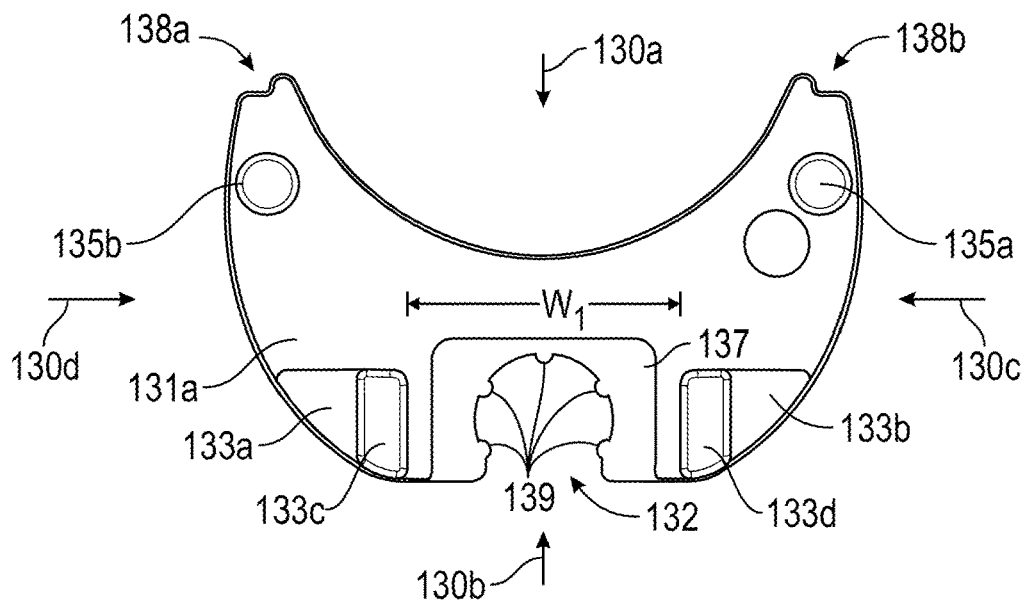
FIGS. 6B and 6C illustrate top and bottom views of the mounting frame of FIG. 6A in accordance with aspects of this disclosure.
Figure 6C:
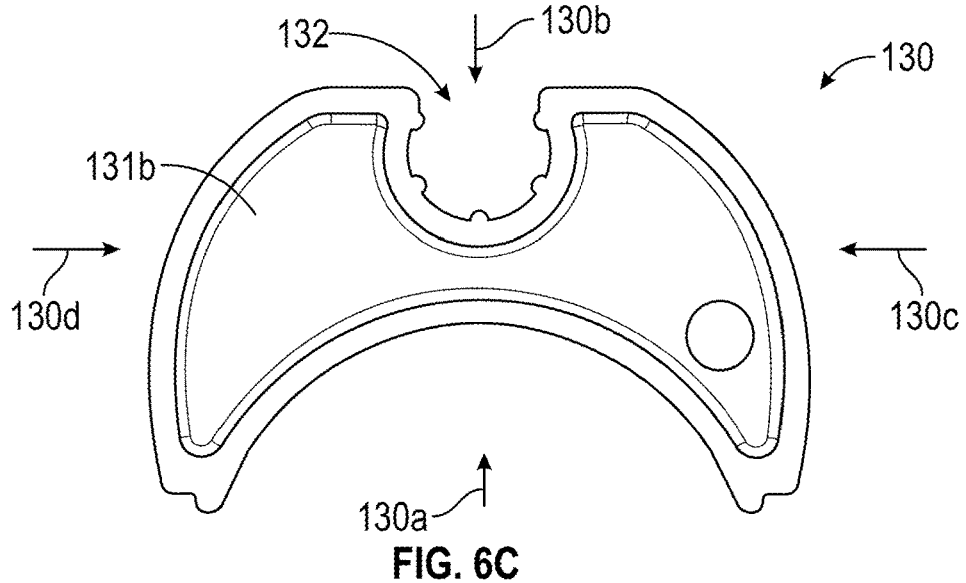

As shown in at least FIGS. 5A-5D and as discussed above, the wearable device 10 can include a mounting frame 130. FIGS. 6A-6C illustrate various views of the mounting frame 130. The mounting frame 130 can secure the circuit board 105 (and electrical components mounted to the circuit board 105) and/or the probe 140 to the housing 40 and/or the mounting frame 130 can operably position the circuit board 105 (and electrical components mounted to the circuit board 105) and/or the probe 140 to the housing 40. Additionally, because the battery holder 115 and battery 110 can be secured to the circuit board 105 as discussed above, the mounting frame 130 can secure the battery 110 and/or battery holder 115 to the housing 40.

With continued reference to FIGS. 6A-6C, the mounting frame 130 can have a first end 130a, a second end 130b opposite the first end 130a, a side 130c, and a side 130d opposite the side 130c. The mounting frame 130 can be sized and/or shaped to conform to a size and/or shape of the battery 110 or a portion thereof. For example, with reference to FIGS. 5A-5D and 6A-6C, the end 130a of the mounting frame 130 (or a portion of the end 130a) can be curved to conform to a portion of a perimeter of the battery 110. The end 130a (or a portion of the end 130a) can comprise a half-moon shape, among other shapes. The curvature of the end 130a can match or partially match a curvature of the battery 110 or a portion thereof. The end 130a can be curved inward toward the end 130b of the mounting frame 130. A surface of the end 130a that faces away from the end 130b can be concave, for example. At least a portion of the end 130 can be sized and/or shaped to surround a portion of the battery 110, such as a portion of a perimeter of the battery 110. For example, at least a portion of the end 130 can be sized and/or shaped to surround less than an entire perimeter of the battery 110, less than ½ of a perimeter of the battery 110, greater than ⅛ of a perimeter of the battery 110, greater than ⅖ of a perimeter of the battery 110, greater than ⅜ of a perimeter of the battery 110, between ⅛ and ⅞ of a perimeter of the battery 110, between ⅛ and ⅝ of a perimeter of the battery 110, between ⅛ and ⅝ of a perimeter of the battery 110, between ⅛ and ½ of a perimeter of the battery 110, approximately ½ of a perimeter of the battery 110, among other values or ranges.

Advantageously, where the end 130a is sized and/or shaped to conform to a size and/or shape of the battery 110 (or a portion of the battery 110) and/or where the end 130a is sized and/or shaped to surround a portion of the battery 110 as described above, such configuration can allow the wearable device 10 to have smaller dimensions while maximizing the size of the battery 110. Minimizing overall dimensions of the wearable device 10 can increase comfort and reduce the bulkiness of the wearable device 10 when placed on a subject and/or handled by a user. Additionally, maximizing the size of the battery 110 in such manner can allow the wearable device 10 to have a longer service life, for example, more than 1 day, more than 2 days, more than 3 days, more than 4 days, more than 5 days, more than 6 days, or more than 7 days.

The mounting frame 130 or a portion thereof can be sized and/or shaped to interact with, secure, retain, and/or position the circuit board 105. For example, the mounting frame 130 can include one or more posts 135a, 135b which are configured to fit within one or more openings 111 in the circuit board 105. With reference to FIGS. 5A-6B, the one or more posts 135a, 135b can fit within a space defined by openings 111 in the circuit board 105. While the figures illustrate the mounting frame 130 having two posts 135a, 135b, the mounting frame 130 can have an alternative amount of posts 135a, 135b. The mounting frame 130 can have one, two, three, four, five, or six or more posts 135a, 135b configured to interact with a corresponding number of openings 111 in the circuit board 105. The one or more posts 135a, 135b can be positioned proximate or adjacent sides 130c, 130d of the mounting frame 130, for example, where the circuit board 105 includes openings 111 on opposite sides and/or edges thereof. The one or more posts 135a, 135b can be positioned in an alternative location, however. The one or more posts 135a, 135b can be positioned closer to the end 130a than to the end 130b of the mounting frame 130 (see FIG. 6B). The one or more posts 135a, 135b can be at least partially retained within the openings 111 and can limit or prevent movement of the circuit board 105 relative to the mounting frame 130 in one or more directions. For example, the one or more posts 135a, 135b, when positioned within the openings 111, can limit or prevent movement of the circuit board 105 relative to the mounting frame 130 in one or more directions along a plane of the circuit board 105. Such plane can extend along and/or be defined by one or more surfaces of the circuit board 105 (for example, opposite surfaces of the circuit board 105). The one or more posts 135a, 135b can have a size and/or shape that corresponds to a size and/or shape of the openings 111 (or a portion thereof). For example, the one or more posts 135a, 135b can have a cylindrical shape that allows positioning within half-circle shaped openings 111. The one or more posts 135a, 135b can extend outward from a surface 131a of the mounting frame 130 (see FIGS. 6A-6B). For example, the one or more posts 135a, 135b can extend transverse (for example, perpendicular) to surface 131a of the mounting frame 130.

The one or more posts 135a, 135b can secure to a portion of the housing 40, as discussed above. For example, the one or more posts 135a, 135b can be sized and/or shaped to secure to and/or within the one or more cavities 49a, 49b of the housing 40. Accordingly, via interaction with the one or more openings 111 of the circuit board 105 and the one or more cavities 49a, 49b of the housing 40, the one or more posts 135a, 135b can secure the circuit board 105 (and components coupled thereto) and the mounting frame 130 to the housing 40. Where the mounting frame 130 is configured to secure the probe 140 (or probe 240) as discussed further below, the one or more posts 135a, 135b can additionally secure the probe 140 (or probe 240) to the housing 40. The securement of the one or more posts 135a, 135b to the one or more cavities 49a, 49b can be a friction fit, for example. As another example, the one or more posts 135a, 135b can comprise a smaller cross-section than the one or more cavities 49a, 49b, allowing the posts 135a, 135b to be received within the cavities 49a, 49b and reduce lateral movement of the mounting frame 130 and housing 40 relative to one another, but also allowing the posts 135a, 135b to more easily be inserted and/or removed from the cavities 49a, 49b (for example, during assembly of the wearable device 10).

The mounting frame 130 can include alternative or additional features that facilitation interaction with, securement and/or retaining of, and/or positioning of the circuit board 105. For example, the mounting frame 130 can include one or more raised portions and/or one or more walls which can extend from a surface 131a of the mounting frame 130 and can retain a portion or portions of the circuit board 105. For example, with reference to FIGS. 6A-6C, the mounting frame 130 can include one or both of raised portions 133a, 133b and/or one or both of walls 133c, 133d. The raised portions 133a, 133b and/or walls 133c, 133d can be positioned proximate or adjacent the end 130b of the mounting frame 130. The walls 133c, 133d can be spaced apart from one another by a distance that is sized to match a portion of the circuit board 105. For example, the walls 133c, 133d can be spaced apart from one another by a width $W_1$ that is sized to receive a width of an end 105a of the circuit board. The width of the end 105a can be smaller than a width of the opposite end 105b of the circuit board 105 and/or smaller than a width of another portion of the circuit board 105 (see FIG. 5C). Advantageously, such configuration can allow the end 105a of the circuit board 105 to be retained between the walls 133c, 133d and can limit or prevent movement of the circuit board 105 relative to the mounting frame 130 in one or more directions along a plane of the circuit board 105 (and/or mounting frame 130). Such plane can extend along and/or be defined by one or more surfaces of the circuit board 105 (for example, opposite surfaces of the circuit board 105). With reference to FIGS. 6A-6B and 5A, the raised portions 133a, 133b can provide additional or alternative securement between portions of the circuit board 105 and the mounting frame 130, for example, portions of the circuit board 105 between the openings 111 and the end 105a. Interaction between the raised portions 133a, 133b, and/or walls 133c, and the end 105a of the circuit board 105 can limit or prevent rotation of the circuit board 105 relative to the mounting frame 130, for example, about an axis extending perpendicular to a surface of the circuit board 105 (for example, a top and/or bottom surface of the circuit board 105). Additionally or alternatively, interaction between the one or more posts 135a, 135b and the openings 111 of the circuit board 105 can limit or prevent rotation of the circuit board 105 relative to the mounting frame 130, for example, about an axis extending perpendicular to a surface of the circuit board 105 (for example, a top and/or bottom surface of the circuit board 105).

As shown in at least FIGS. 6A-6C, one or both of sides 130c, 130d (or portions thereof) can be curved and/or rounded. For example, one or both of surfaces of the sides 130c, 130d can be convex. Alternatively, one or both of sides 130c, 130d can be straight. Where the mounting frame 130 includes one or more of raised portions 133a, 133b, one or both of the raised portions 133a, 133b can be adjacent the sides 130c, 130d and can be curved similarly as the sides 130c, 130d (see FIG. 6B).

With reference to FIG. 6B, the mounting frame 130 can include one or both of notches 138a, 138b at corners where the end 130a joins the sides 130c, 130d. The notches 138a, 138b can interact with the opposing arms 115a, 115b of the battery holder 115 to facilitate alignment, positioning, and/or engagement between the mounting frame 130 and the battery holder 115 (see FIGS. 5A-5B and FIG. 6B).

As discussed elsewhere herein and as shown in at least FIGS. 5A-5D, the wearable device 10 can include a probe 140 that can be configured to transmit thermal energy from the subject to, toward, and/or near one or more temperature sensors of the wearable device 10. The mounting frame 130 can be configured to secure the probe 140 and/or operably position the probe 140 with respect a subject's skin. For example, the mounting frame 130 can include an opening sized and/or shaped to receive and/or secure the probe 140 or a portion thereof. The opening can extend through a thickness or depth of the mounting frame 130. The opening can be positioned adjacent or proximate to end 130a, end 130b, side 130c, and/or 130d. The opening can be a slot, for example, the slot 132 shown in at least FIGS. 5C-6C. As shown, the slot 132 can be positioned at and/or along end 130b of the mounting frame 130. The slot 132 can be sized and/or shaped to receive and/or secure a portion of the probe 140. For example, the slot 132 can be shaped and/or sized to match a size and/or shape of a portion of a cross-section and/or exterior surface or perimeter of the probe 140. The slot 132 can comprise a circular or partially circular shape, for example, where the probe 140 has a cylindrical shape. The slot 132 can be positioned adjacent end 130b so as to allow the probe 140 to be inserted into the slot 132 along a direction that is transverse (for example, perpendicular) to an axis extending through a center of the slot 132. Additionally or alternatively, the slot 132 can be sized, shaped, and/or positioned to allow the probe 140 (or a portion thereof) to be inserted into the slot 132 along a direction that is parallel to such axis extending through a center of the slot 132. The slot 132 can be sized and/or shaped to surround a portion of the probe 140. For example, the slot 132 can be sized and/or shaped to surround a portion of a cross-section and/or exterior surface or perimeter of the probe 140. For example, the mounting frame 130 and/or the slot 132 can be configured such that, when the probe 140 is secured to the mounting frame 130, the mounting frame 130 surrounds less than an entire perimeter of a cross-section of the probe 140, greater than ¼ of a perimeter of a cross-section of the probe 140, greater than ½ of a perimeter of a cross-section of the probe 140, greater than ¾ of a perimeter of a cross-section of the probe 140, approximately ½ of a perimeter of a cross-section of the probe 140, approximately ¾ of a perimeter of a cross-section of the probe 140, or any value therebetween, or any range bounded by any combination of these values, although values and ranges outside these values or ranges can be used in some cases.

As discussed in more detail below, the probe 140 can have a body 144 having a recessed portion 146 which has a cross-section that is smaller than a cross-section of the body 144 of the probe 140. The slot 132 can be sized and/or shaped to receive a size and/or shape of the recessed portion 146 of the probe 140, for example. The slot 132 can have a depth (oriented vertically in the view of FIGS. 5C-5D) that is less than, equal to, or greater than a height (oriented vertically in the view of FIGS. 5C-5D) of the recessed portion 146 of the probe 140 which extends along a portion of a height of the body 144 of the probe 140. With reference to FIGS. 6A-6C, the slot 132 can include one or more protrusions 139 extending along the depth of the slot 132 (or a portion of the depth of the slot 132). For example, the slot 132 can include, one, two, three, four, five, or six or more protrusions 139. The one or more protrusions 139 can be spaced from one another, equidistantly or non-equidistantly, along a length (or width) of the slot 132 (see FIGS. 6A-6C). The protrusions 139 can extend outward from (for example, perpendicular to) a surface of the slot 132. The protrusions 139 can be rigid or alternatively, non-rigid (for example, flexible). The protrusions 139 can engage a portion of the probe 140 when the probe 140 is positioned within the slot 132. For example, the protrusions 139 can engage the recessed portion 146 of the probe 140 when the probe 140 is positioned within the slot 132. The slot 132 can secure the probe 140 in a friction-fit engagement and/or snap-fit engagement, or other type of engagement for example.

When the probe 140 is secured within the slot 132, the probe 140 (and/or an axis extending through a center of the probe 140) can be oriented transverse (for example, perpendicular) to a plane and/or surface of the mounting frame 130. For example, when the probe 140 is secured within the slot 132, the probe 140 can be oriented perpendicular to the surface 131a of the mounting frame 130. Additionally or alternatively, when the probe 140 is secured within the slot 132 of the mounting frame 130, the probe 140 can be oriented perpendicular to the circuit board 105 (and/or a surface or plane of the circuit board 105). Such positioning can help the probe 140 make contact with (whether direct, or indirect via substrates 65 and/or 25) and/or apply pressure to a portion of the subject's skin to facilitate transmission of thermal energy through the probe 140 to and/or near other portions of the wearable device 10 (such as toward temperature sensor 150*a*).

With reference to FIGS. 6A-6B, the mounting frame 130 can include a recessed portion 137 that can be recessed from surface 131*a* of the mounting frame 130. The recessed portion 137 can be positioned proximate or adjacent end 130*b* of the mounting frame 130. The recessed portion 137 can be positioned around the slot 132. A perimeter of the recessed portion 137 can be larger than a perimeter of the slot 132. The perimeter of the recessed portion 137 can be spaced outward from the perimeter of the slot 132 (see FIG. 6B). The recessed portion 137 can be recessed from the surface 131*a* a depth (oriented vertically in the view of FIGS. 5C-6A) that is sized to correspond to a height of a portion of the probe 140. For example, the recessed portion 137 can be recessed from the surface 131*a* a depth that is sized to correspond to a height (oriented vertically in the view of FIGS. 5C-5D) of a top portion 148 of the probe 140 which is discussed in more detail below. Such configuration can allow a height of the top portion 148 of the probe 140 to fit within the depth of the recessed portion 137 when the probe 140 is secured within the slot 132.

As discussed elsewhere herein and as illustrated in FIG. 7, the wearable device 10 can include a probe 140 that can act as a conduit to transmit thermal energy from the subject's skin to, toward, and/or near one or more temperature sensors of the wearable device 10. As shown in at least FIGS. 5C-5D, the probe 140 can comprise a first end 142*a*, a second end 142*b* opposite the first end 142*a*, and a body 144. The probe 140 (and/or body 144 of probe 140) can include a height extending between the first and second ends 142*a*, 142*b*. The probe 140 can comprise a variety of shapes and/or sizes. The probe 140 can comprise a cylindrical shape among others. As shown, the body 144 can comprise a recessed portion 146 extending along a portion of the body 144 of the probe 140. The recessed portion 146 can be recessed from an outer surface of the body 144. The recessed portion 146 can assist the probe 140 in securing to and/or within the slot 132 of the mounting frame 130. For example, a height of the recessed portion 146 can be sized to correspond to a depth of the slot 132 of the mounting frame 130 so as to allow portions of the body 144 proximate the recessed portion 146 to engage top and bottom surfaces of the mounting frame (and/or recessed portion 137 of the mounting frame 130) when the probe 140 is received within the slot 132. As discussed above, the slot 132 can include one or more protrusions 139 along a width of the slot 132. The recessed depth of the recessed portion 146 of the probe 140 can be sized to fit a distance that the one or more protrusions 139 extend outward from the surface of the slot 132. Additionally or alternatively, the height of the recessed portion 146 of the probe 140 can be sized to fit a height of the one or more protrusions 139. For example, the one or more protrusions 139 can extend outward from a surface of the slot 132 a given distance that corresponds to a depth of the recessed portion 146 (with respect to the outer surface of body 144). As another example, the one or more protrusions 139 can have a height extending along a depth of the slot 132 that corresponds to a height of the recessed portion 146. The height of the recessed portion 146 can extend along a portion of the height of the probe 140 ("vertically" given the orientation shown in FIGS. 5C-5D).

As discussed above, the wearable device 10 can include one or more temperature sensors. FIGS. 5A, 5C, and 5D illustrate a temperature sensor 150*a* positioned on a first surface of the circuit board 105. When the probe 140 is secured to the mounting frame 130, the probe 140 can be aligned with and/or positioned proximate to the temperature sensor 150*a*. For example, with respect to FIGS. 5A-5B, when the probe 140 is secured to the mounting frame 130 (for example, within the slot 132), the probe 140 can be vertically aligned with the temperature sensor 150*a*. For example, an axis extending through a center of the probe 140 can extend through the temperature sensor 150*a*, and such axis can be perpendicular to a surface or plane of the circuit board 105. When the probe 140 is secured to the mounting frame 130 (for example, within the slot 132), the end 142*a* of the probe 140 can be positioned proximate or adjacent a surface (for example, bottom surface) of the circuit board 105 proximate the temperature sensor 150*a*. As another example, when the probe 140 is secured to the mounting frame 130 (for example, within the slot 132), the end 142*a* of the probe 140 can be positioned adjacent a first surface (for example, bottom surface) of the circuit board 105 and the temperature sensor 150*a* can be positioned adjacent a second surface (for example, a top surface) of the circuit board 105 and the probe 140 and the temperature sensor 150*a* can be aligned. As another example, when the probe 140 is secured to the mounting frame 130 (for example, within the slot 132), the circuit board 105 can be positioned between the probe 140 and the temperature sensor 150*a*.

The wearable device 10 can include a thermally conductive material and/or layer between the end 142*a* of the probe 140 and a surface of the circuit board 105. For example, with reference to FIGS. 5C-5D, the wearable device 10 can include a thermal paste 173 positioned between the end 142*a* of the probe 140 and a surface of the circuit board 105 (for example, a bottom surface of the circuit board 105 given the orientation shown in FIGS. 5C-5D). The thermal paste 173 can be aligned (for example, vertically aligned) with the probe 140 and/or the temperature sensor 150*a*. The thermal paste 173 can comprise zinc oxide, for example. The thermal paste 173 can be silicone free. The thermal paste 173 can comprise a circular shape, among other shapes. For example, the thermal paste 173 can be in the form of a disc. The thermal paste 173 can conform to a shape of the probe 140 and/or can deform when positioned between the circuit board 105 and the probe 140. The thermal paste 173 can reduce or prevent air gaps between end 142*a* of the probe 140 and the circuit board 105 and thus increase thermal transmissivity.

With reference to FIG. 5D, the circuit board 105 can include one or more openings 159 extending through the circuit board 105. For example, the one or more openings 159 can extend through a thickness of the circuit board 105 and/or between opposing surfaces (for example, top and bottom surfaces) of the circuit board 105. The one or more openings 159 can be located adjacent to the temperature sensor 150*a*, the thermal paste 173, and/or the probe 140 (for example, end 142*a* of the probe 140). The one or more openings 159 can allow thermal energy to flow from the probe 140 and/or thermal paste 173 through the circuit board 105 to the temperature sensor 150*a*. In such configuration, the one or more openings 159 can provide a passageway by which such thermal energy can flow from the probe 140 and/or thermal paste 173 through the circuit board 105 and to the temperature sensor 150*a*. The circuit board 150 can include one, two, three, four, five, six, seven, eight, nine, or ten or more openings 159. The circuit board 150 can include between one and twenty openings 159, between one and ten openings 159, between one and five openings 159, for example. The circuit board 105 can include a plurality of openings 159, for example, more than two, more than three, more than four, more than five, more than six, more than seven, or more than eight openings 159. The circuit board 105 can include a plurality of openings 159 arranged in an array and/or pattern. For example, the circuit board 105 can include a plurality of openings 159 arranged in an array having a rectangular shape (see FIG. 5D), square shape, circular shape, among others. The plurality of openings 159 can be spaced equidistantly from one another in some cases.

Where such openings 159 are arranged in an array, dimensions of the array can correspond to dimensions of the probe 140 to ensure that thermal energy flowing through the end 142a of the probe 140 is conveyed through the circuit board 105 to the temperature sensor 150a efficiently. For example, where the probe 140 has a circular cross-section, the circuit board 105 can include a plurality of openings 159 arranged in a circular array having a diameter that is less than, equal to, or greater than a diameter of the circular cross-section of the probe 140. As another example, where the probe 140 has a circular cross-section, the circuit board 105 can include a plurality of openings 159 arranged in a non-circular array (e.g., a square or rectangular array) whose length and/or width dimensions are less than, equal to, or greater than a diameter of the circular cross-section of the probe 140. As another example, where the probe 140 has a cross-section having a length and width, a length and/or width of an array of the plurality of openings 159 can be less than, equal to, or greater than such length and/or width of the cross-section of the probe 140.

In some variants, the one or more openings 159 include (for example, are filled with) a thermally conductive material, such as gold and/or copper, to increase thermal transmissivity through the circuit board 105. When the wearable device 10 is assembled, the one or more openings 159 (and/or an array formed by a plurality of the openings 159) can align with the temperature sensor 150a, the thermal paste 173, the probe 140 (for example, an axis extending through a height of the probe 140), the slot 132 of the mounting frame 130, and/or the opening 55 of substrate 50. In some implementations, an axis extending through a center of an array defined by a plurality of openings 159 can align with the temperature sensor 150a, the thermal paste 173, the probe 140 (for example, an axis extending through a height of the probe 140), the slot 132 of the mounting frame 130, and/or the opening 55 of substrate 50. Each of the one or more openings 159 can be smaller than opening 55 of substrate 50 and/or smaller than slot 132 in mounting frame 130, each of which are discussed elsewhere herein. Where the circuit board 105 includes a plurality of openings 159 arranged in an array, the region or area defining and/or forming the boundary of such array can be smaller than opening 55 of substrate 50 and/or smaller than slot 132 in mounting frame 130.

With continued reference to FIGS. 5C-5D, the thermal paste 173 can be positioned between the one or more openings 159 of the circuit board 105 and the thermally conductive probe 140. The thermal paste 173 can be positioned between a surface of the circuit board 105 and the thermally conductive probe 140. The thermal paste 173 can be positioned between end 142a of the thermally conductive probe 140 and a surface of the circuit board 105. The thermal paste 173 can be positioned between end 142a of the thermally conductive probe 140 and the one or more openings 159 of the circuit board 105.

With continued reference to FIG. 5D, the wearable device 10 can include a thermally conductive pad 155 positioned adjacent to the one or more openings 159 and a surface (for example, a bottom surface) of the circuit board 105. The thermally conductive pad 155 can be positioned between the one or more openings 159 and the thermal paste 173 and/or the probe 140. The thermally conductive pad 155 can increase thermal transmissivity of thermal energy from the probe 140 and the thermal paste 173 to the one or more openings 159 through the circuit board 105 and to the temperature sensor 150a. The thermally conductive pad 155 can be metallic. For example, the thermally conductive pad 155 can include gold and/or copper.

FIG. 7 illustrates a cross-section view taken along a portion of the assembled view of the wearable device 10 shown in FIG. 2C when placed adjacent skin of a subject. As shown, when the probe 140 is secured to the mounting frame 130 (for example, within the slot 132) and the mounting frame 130 is secured to the housing 40, the end 142b of the probe 140 can be positioned in proximity to the subject's skin. As also shown, the probe 140 can apply pressure to and/or press against a portion of the skin of a subject when the wearable device 10 is placed on and/or secured to the subject. Where the wearable device 10 includes substrates 65 and/or 25 coupled with the housing 40 (for example, via securement to substrate 50), the substrates 65, 25 can be positioned between the end 142b of the probe 140 and the skin of the subject when the wearable device 10 is secured to the user. As discussed previously, the substrate 50 (which can comprise foam), can include an opening 55 that is sized and/or shaped to allow a portion of the probe 140 to extend therethough.

In some implementations, the probe 140 extends through opening 55 and beyond a surface of substrate 50 (for example, a "bottom" surface of substrate 50) a distance that is equal to or greater than approximately 0.01 inch, approximately 0.02 inch, approximately 0.03 inch, approximately 0.04 inch, approximately 0.05 inch, approximately 0.06 inch, approximately 0.07 inch, approximately 0.08 inch, approximately 0.09 inch, approximately 0.1 inch, approximately 0.2 inch, approximately 0.3 inch, approximately 0.4 inch, or approximately 0.5 inch, or any value or range between any of these values, or any value or range bounded by any combination of these values. In some implementations, the probe 140 extends through opening 55 and beyond a surface of substrate 50 (for example, a "bottom" surface of substrate 50) a distance that is between approximately 0.01 inch and approximately 0.5 inch, for example, between approximately 0.02 inch and approximately 0.4 inch, between approximately 0.03 inch and approximately 0.3 inch, between approximately 0.04 inch and approximately 0.2 inch, between approximately 0.05 inch and approximately 0.1 inch, between approximately 0.06 inch and approximately 0.09 inch, between approximately 0.07 inch and approximately 0.08 inch, between approximately 0.05 inch and approximately 0.2 inch, or between approximately 0.09 inch and approximately 0.2 inch, or any value or range between any of these values or ranges, or any value or range bounded by any combination of these values. Alternatively, in some implementations, the probe 140 does not extend beyond the bottom surface of the substrate 50. For example, in some implementations, the probe 140 extends through the opening 55 but terminates at the bottom surface of the substrate 50 such that a plane of the end 142b of the probe 140 is generally parallel to a plane of the bottom surface of the substrate 50.

When the wearable device 10 is assembled and placed and/or secured to the subject's skin and the end 142b of the probe 140 extends through the opening 55 of substrate 50, the substrate 65 and/or substrate 25 can be positioned between the subject's skin surface and the end 142b of the probe 140. Accordingly, in such configuration, the probe 140 (for example, the end 142*b* of the probe 140) can indirectly contact a portion of the subject's skin. As discussed above, the substrate 65 can cover the opening 55 and the end 142*b* of the probe 140 and prevent fluid (for example, sweat) ingress through the opening 55 and to an interior of the housing 40, for example, to and/or toward electrical components of the wearable device 10. As also discussed above, substrate 25 can comprise a thermally conductive material and/or can be configured to allow thermal energy to pass from the subject's skin to the end 142*b* of the probe 140. As also discussed above, any of substrates 25, 65, 50, and/or 20 can advantageously insulate portions of the subject's skin. When a portion of the probe 140 is positioned through the opening 55 (for example, the end 142*b* through the opening 55 of the substrate 55), the substrates 25, 20, 65, and/or 50 can insulate portions of the subject's skin around and/or underneath the end 142*b* of the probe 140, which can allow the probe 140 to transmit thermal energy indicative of the subject's core body temperature, as discussed previously.

The probe 140 can comprise thermally conductive material that allows the probe 140 to transmit and/or act as a conduit for thermal energy of the subject. Thus, thermal energy from the subject's skin can pass through substrates 25 and/or 65, and the probe 140. As discussed above, the probe 140 can comprise aluminum, for example, among other thermally conductive materials. As also discussed above, the probe 140 can be rigid, which can allow the probe 140 to apply pressure to a portion of the subject's skin. Such application of pressure to a portion of the subject's skin can allow the probe 140 to better receive thermal energy from the subject. For example, the probe 140 can be not compressible and/or not extendible (for example, not compressible and/or not extendible relative to a longitudinal axis extending along a height of the probe 140). As another example, the probe 140 can be not compressible and/or not extendible relative to a longitudinal axis extending through a center of a cross-section of the probe 140.

As discussed above and as illustrated in FIG. 7, the end 142*a* of the probe 140 can be positioned adjacent a first surface of the circuit board 105 (for example, a "bottom" surface of the circuit board 105) and the temperature sensor 150*a* can be positioned adjacent a second surface of the circuit board 105 (for example, a "top" surface of the circuit board 105). As also discussed above, a thermal paste 173 can be positioned between the end 142*a* of the probe 140 and the circuit board 150. As also discussed above, a thermally conductive pad 155 can be positioned between one or more openings 159 in the circuit board 105 and the thermal paste 173 and/or the probe 140. The one or more openings 159 can allow thermal energy to pass through the circuit board 105 to the temperature sensor 150*a*.

As thermal energy is transmitted to the temperature sensor 150*a*, the temperature sensor 150*a* can determine a body temperature of the subject and/or can generate and transmit one or more signals responsive to the thermal energy to the processor 11 of the wearable device 10. The temperature sensor 150*a* can be or include, a thermocouple and/or a thermistor, for example. The temperature sensor 150*a* can be a chip that is electrically and mechanically coupled with the circuit board 105. The temperature sensor 150*a* can be configured to generate one or more signals responsive to detected thermal energy, determine body temperature, and/or transmit such generated one or more signals and/or such determined body temperature to the processor 11 of the wearable device 10 continuously and/or intermittently. For example, temperature sensor 150*a* can be configured to generate one or more signals responsive to detected thermal energy, determine body temperature, and/or transmit such generated one or more signals and/or such determined body temperature every 0.5 seconds, 1 second, 2 second, 3 seconds, 4 seconds, 5 seconds, 10 seconds, 30 seconds, 1 minute, 2 minute, 3 minutes, 4 minutes, 5 minutes, or at other intervals.

In addition to temperature sensor 150*a*, the wearable device 10 can include one or more additional temperature sensors. For example, with reference to FIG. 5C, the wearable device 10 can include temperature sensor 150*b*. Similar to temperature sensor 150*a*, temperature sensor 150*b* can be electrically and/or mechanically coupled to the circuit board 105. Temperature sensor 150*b* can be spaced away from the temperature sensor 150*a*. Temperature sensor 150*b* can be used to detect a temperature within an interior of the housing 40 and/or proximate the circuit board 105, for example. Temperature sensor 150*b* can be used to measure an ambient temperature, for example, a temperature outside the interior of the housing 40.

In some implementations, the temperature sensor 150*b* is surrounded by a material in order to isolate the temperature sensor 150*b* from nearby electrical components and/or to prevent the temperature sensor 150*b* from being thermally influenced by the temperature of the interior of the housing 40 so that the temperature sensor 150*b* can better measure ambient temperatures outside the housing 40. For example, with reference to FIGS. 5A and 5C, the wearable device 10 can include a thermal putty 120 which can be positioned around and/or adjacent to the temperature sensor 150*b*. Thermal putty 120 can be positioned between the temperature sensor 150*b* and an interior surface of the top portion 41*a* of the housing 40 (see FIGS. 5A, 5C, and 4B). For example, the thermal putty 120 can extend from a surface of the circuit board 105 around the temperature sensor 150*b* outward (for example, "upward" given the view shown in FIGS. 5A and 5C) to the interior surface of the top portion 41*a* of the housing 40. Advantageously, the thermal putty 120 can transmit thermal energy from the surface of the housing 40 (which is in thermal contact with ambient) to the temperature sensor 150*b*. The thermal putty 120 can deform and/or conform to a shape of a portion of the interior surface of the top portion 41*a* of the housing 40 in order to better facilitate the transfer of thermal energy from the interior surface (and ambient) to the temperature sensor 150*b*. The temperature sensor 150*b* can be configured to generate one or more signals based on received thermal energy, whether from the interior of the housing 40 or from ambient (for example, via the thermal putty 120). The thermal putty 120 can be a ceramic filled silicone sheet, for example.

The temperature sensor 150*b* can be configured to generate one or more signals responsive to detected thermal energy, determine temperature, and/or transmit such generated one or more signals and/or such determined temperature to the processor 11 of the wearable device 10 continuously and/or intermittently. For example, temperature sensor 150*b* can be configured to generate one or more signals responsive to detected thermal energy, determine temperature, and/or transmit such generated one or more signals and/or such determined temperature every 0.5 seconds, 1 second, 2 second, 3 seconds, 4 seconds, 5 seconds, 10 seconds, 30 seconds, 1 minute, 2 minute, 3 minutes, 4 minutes, 5 minutes, or at other intervals. Such generated one or more signals, determined temperature, and/or transmission of such generated one or more signals and/or determined temperature can be simultaneous or non-simultaneous with the generated one or more signals, determined body temperature, and/or transmitted one or more signals and/or determined body temperature from temperature sensor 150a.

Advantageously, incorporating both of temperature sensors 150a, 150b can allow the wearable device 10 to more accurately determine a core body temperature of the user. For example, the processor 11 can utilize temperature data from the temperature sensor 150b in order to adjust or "correct" temperature data received from the first temperature sensor 150a in order to more accurately determine a subject's core body temperature. For example, the processor 11 can compare temperature data received from both of the temperature sensors 150a, 150b and determine a corrected body temperature based on such comparison. The processor 11 can apply weight factors to one or both of temperature data received from temperature sensors 150a, 150b and/or otherwise compare such received data to determine a corrected body temperature.

As discussed above and with continued reference to FIG. 7, the housing 40 can include a recess 43 that is recessed a depth $D_1$ from portions of the interior surface of the housing 40 (such as interior surface of the top portion 41a) which is less than a thickness $T_1$ of the housing 40 (such as a thickness of the top portion 41a of the housing 40). The recess 43, depth $D_1$, and thickness Tare illustrated in FIG. 7. As discussed above, the recess 43 can advantageously provide more spacing and/or distance between the temperature sensor 150a and the housing 40 (such as the top portion 41a of the housing 40) to prevent the temperature sensor 150a from being influenced by the temperature of the housing 40 and/or ambient temperature surrounding the housing 40 and/or wearable device 10.

FIGS. 8A-8D illustrate an alternative design for an electronics assembly 200 that can be incorporated within the wearable device 10. The electronics assembly 200 can be the same in some or many respects to the electronics assembly 100 discussed above. More specifically, some or many of the components that can form and/or be part of the electronics assembly 100 as discussed above can also form and/or be part of the electronics assembly 200. For example, the electronics assembly 200 can be formed from the circuit board 105, battery 110, battery holder 115, mounting frame 130, temperature sensor 150a, thermal putty 120, temperature sensor 150b, thermal paste 173, thermally conductive pad 155, one or more openings 159, and/or emitter 133, along with one or more other components that are discussed below with reference to FIGS. 8A-10B. Accordingly, the discussion above with reference to any or all of these components and/or other components discussed above is equally applicable to the electronics assembly 200 and components that can form the electronics assembly 200. As mentioned above, the use of the phrase "electronics assembly" or the reference numeral "200" in the present disclosure is not intended to be limiting, but rather, is merely intended as a way to refer to one or more components of the wearable device 10, for example, which can be enclosed by the housing 40 and/or one or more of substrates 70, 25, 65, 50, 65, and/or 20.

Figure 8A:
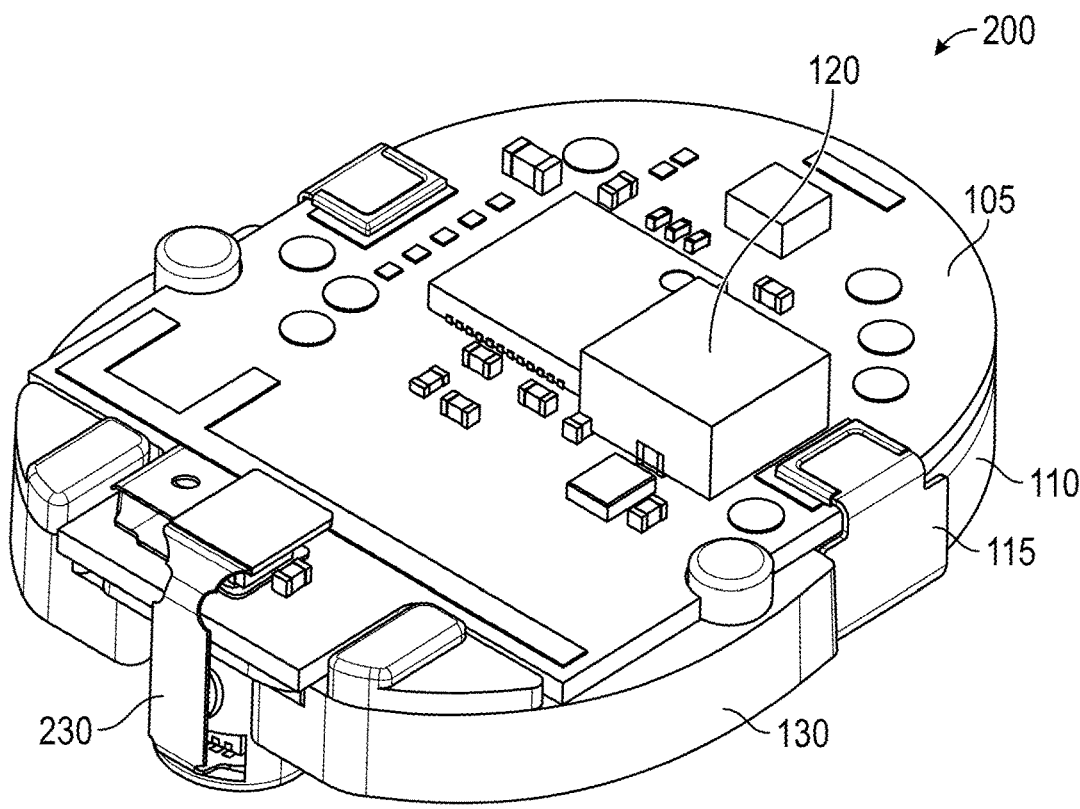
FIGS. 8A and 8B illustrate top and bottom perspective views of a portion of the wearable device of FIG. 1 in accordance with aspects of this disclosure.
Figure 8B:
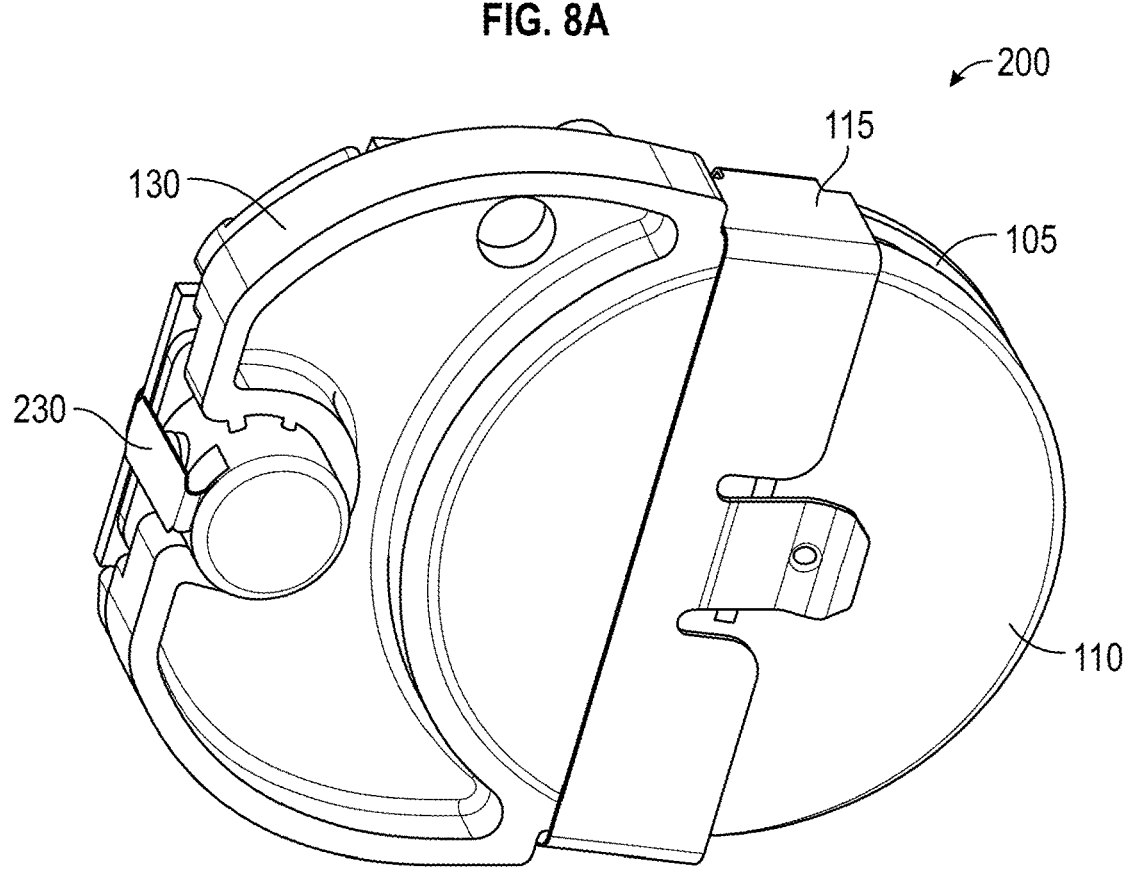

FIGS. 8A-8D illustrate an alternative design for a probe 240. FIGS. 8A-8B illustrate an assembled view where probe 240 is secured to the mounting frame 130 (and other components of the wearable device 10) and FIGS. 5C-5D illustrate an exploded view of the probe 240 along with other components of the wearable device 10. FIGS. 8A-8D also illustrate a flexible circuit 230 and a temperature sensor 150c which can be coupled to a portion of the flexible circuit 230. The flexible circuit 230 can include a first end or portion 232 which can be coupled to temperature sensor 150a and/or the circuit board 105 proximate a first surface of the circuit board 105 (for example, a "top" surface of the circuit board 105) and a second end or portion 234 that can be coupled with and/or can support the temperature sensor 150c. The flexible circuit 230 can include a stem 236 which can be connected to the first and second portions (or ends) 232, 234 of the flexible circuit 230.

Similar to as discussed with respect to probe 140, the probe 240 can be rigid. For example, the probe 240 can be not compressible and/or not extendible (for example, not compressible and/or not extendible relative to a longitudinal axis extending along a height of the probe 240). As another example, the probe 240 can be not compressible and/or not extendible relative to a longitudinal axis extending through a center of a cross-section of the probe 240.

Figure 9A:
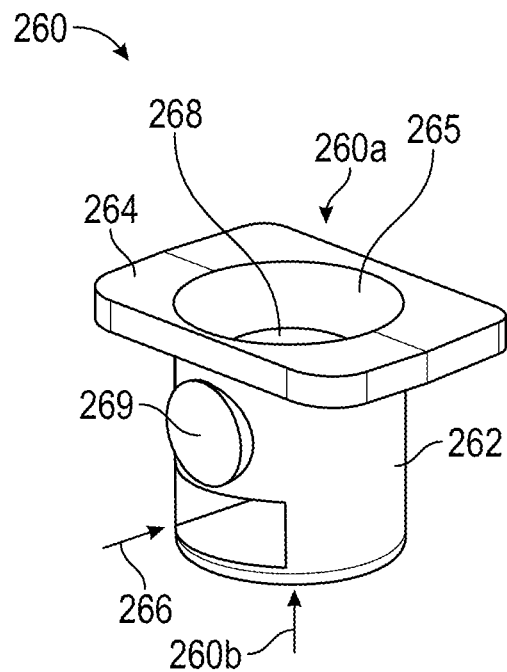
FIGS. 9A-10B illustrate various views of portions of a probe of the portion the wearable device illustrated in FIGS. 8C-8D in accordance with aspects of this disclosure.
Figure 9B:
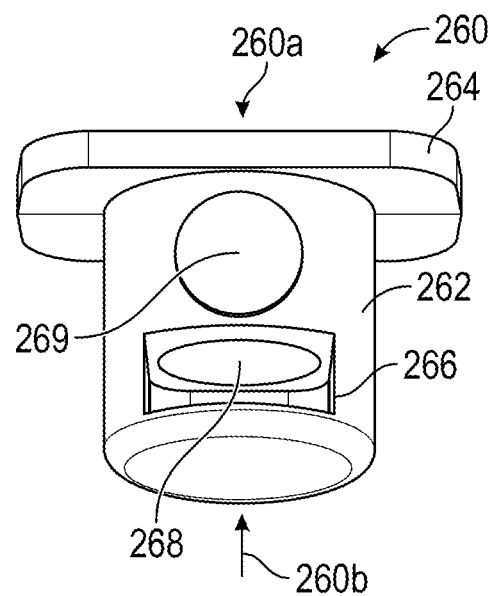
Figure 10A:
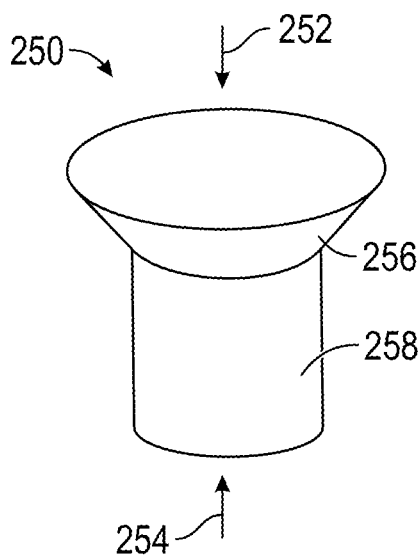
Figure 10B:
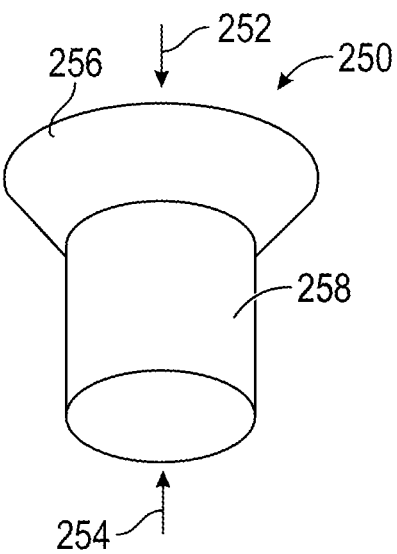

FIGS. 9A-10B together illustrate the probe 240. The probe 240 can include a receptacle 260 (FIGS. 9A-9B) and an insert 250 (FIGS. 10A-10B) configured to be received within a portion of the receptacle 260 (which can also be referred to as a "housing 260"). The insert 250 can include a first end 252, a second end 254 opposite the first end 252, a body 258, and a head 256. The body 258 can comprise a cylindrical shape, among others. The head 256 of the insert 250 can be flared outward around a portion of the body 258. The head 256 of the insert 250 can be tapered. The head 256 of the insert 250 can extend around a portion of a perimeter of the body 258 and/or can be positioned at or near the end 252. The head 256 can have a cross-section that increases from a region where the head 256 connects to the body 258 to the end 252. The head 256 can have a frustoconical shape, as illustrated in FIGS. 10A-10B. As discussed below, the body 258 can be sized and/or shaped to fit within a cavity 268 of the receptacle 260. As also discussed below, the head 256 can be sized and/or shaped to fit within a tapered recess 265 of the receptacle 260.

The receptacle 260 can include a first end 260a, a second end opposite the first end 260b, and a body 262. The receptacle 260 can include a head 264 which extends outward from the body 262 and/or which has a cross-section that is greater than a cross-section of the body 262. The head 264 can be located at or near the end 260a of the receptacle 260. The body 262 can be cylindrical, among other shapes, similar to the shape of the body of the probe 140, for example. The head 264 can be sized and/or shaped to fit within the recessed portion 137 of the mounting frame 130 discussed above with reference to FIGS. 6A-6C. The head 264 can comprise a square or rectangular shape, for example, and the head 264 can have rounded corners. A height (or thickness) of the head 264 can be sized to match a depth of the recessed portion 137 of the mounting frame 130 so as to allow the head 264 to fit within the space defined by the recessed portion 137. Such configuration can allow the receptacle 260 (and the probe 240) to be at least partially secured to the mounting frame 130. Similar to the body 144 of the probe 140, the body 262 of the receptacle 260 can be sized and/or shaped to fit within the slot 132 of the mounting frame 130. Accordingly, the discussion above with reference to the securement and/or positioning of the probe 140 within the slot 132 of the mounting frame 130 is equally applicable to the probe 240 (and receptacle 260).

The receptacle 260 can include a protrusion 269 extending outward from a portion of a surface of the body 262 (see FIGS. 9A-9B). The protrusion 269 can extend outward from the surface of the body 262 and have a flat or planar end which can provide a flat surface by which the stem 236 of the flexible circuit 230 can rest against and/or contact, which can help with alignment and/or positioning of the stem 236 and flexible circuit 230 with respect to the receptacle 260 and the probe 240. The protrusion 269 can be circular shaped, for example, or another shape.

The receptacle 260 can include a cavity 268 extending through a portion of a height of the receptacle 260 (for example, the body 262). The cavity 268 can extend along an axis aligned with a height of the receptacle 260 and/or extending through a center of a cross-section of the receptacle 260. The receptacle 260 can additionally include an opening 266 positioned along an outer surface of the body 262. The opening 266 can extend inward from the outer surface of the body 262 towards an interior of the body 262. The opening 266 can meet and/or join the cavity 268 within an interior of the body 262. An axis extending through the opening 266 (e.g., a center of the opening 266) can be transverse (for example, perpendicular) to an axis extending through the cavity 268 (e.g., a center of the cavity 268). The opening 266 can be positioned proximate the end 260b of the receptacle 260. The opening 266 can be positioned closer to the end 260b than to the end 260a of the receptacle 260.

The cavity 268 can be sized and/or shaped to receive the insert 250 or a portion thereof. For example, the cavity 268 can be sized and/or shaped to receive the body 258 of the insert 250. The cavity 258 can be cylindrical, among other shapes, for example. The head 264 of the receptacle 260 can include a tapered recess 265 around the cavity 268. The tapered recess 265 can be sized and/or shaped to receive the head 256 of the insert 250 such that, when the body 258 is positioned within the cavity 268, the end 252 of the insert 250 sits "flush" (for example, on the same plane) with a surface of the end 260a and/or the head 264 of the receptacle 260.

Figure 8C:
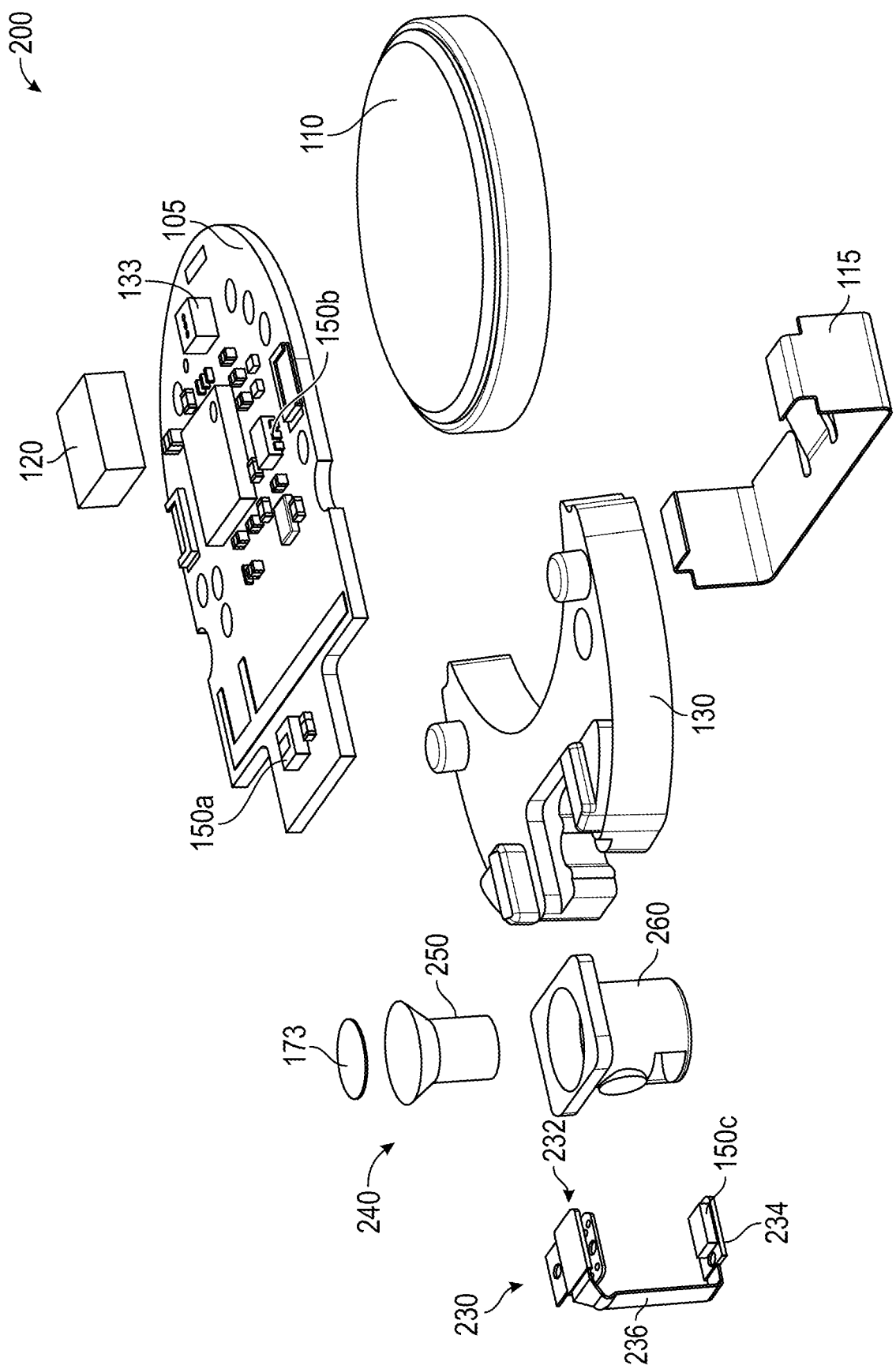
FIGS. 8C and 8D illustrate top and bottom exploded perspective views of the portion of the wearable device of FIGS. 8A and 8B in accordance with aspects of this disclosure.
Figure 8D:
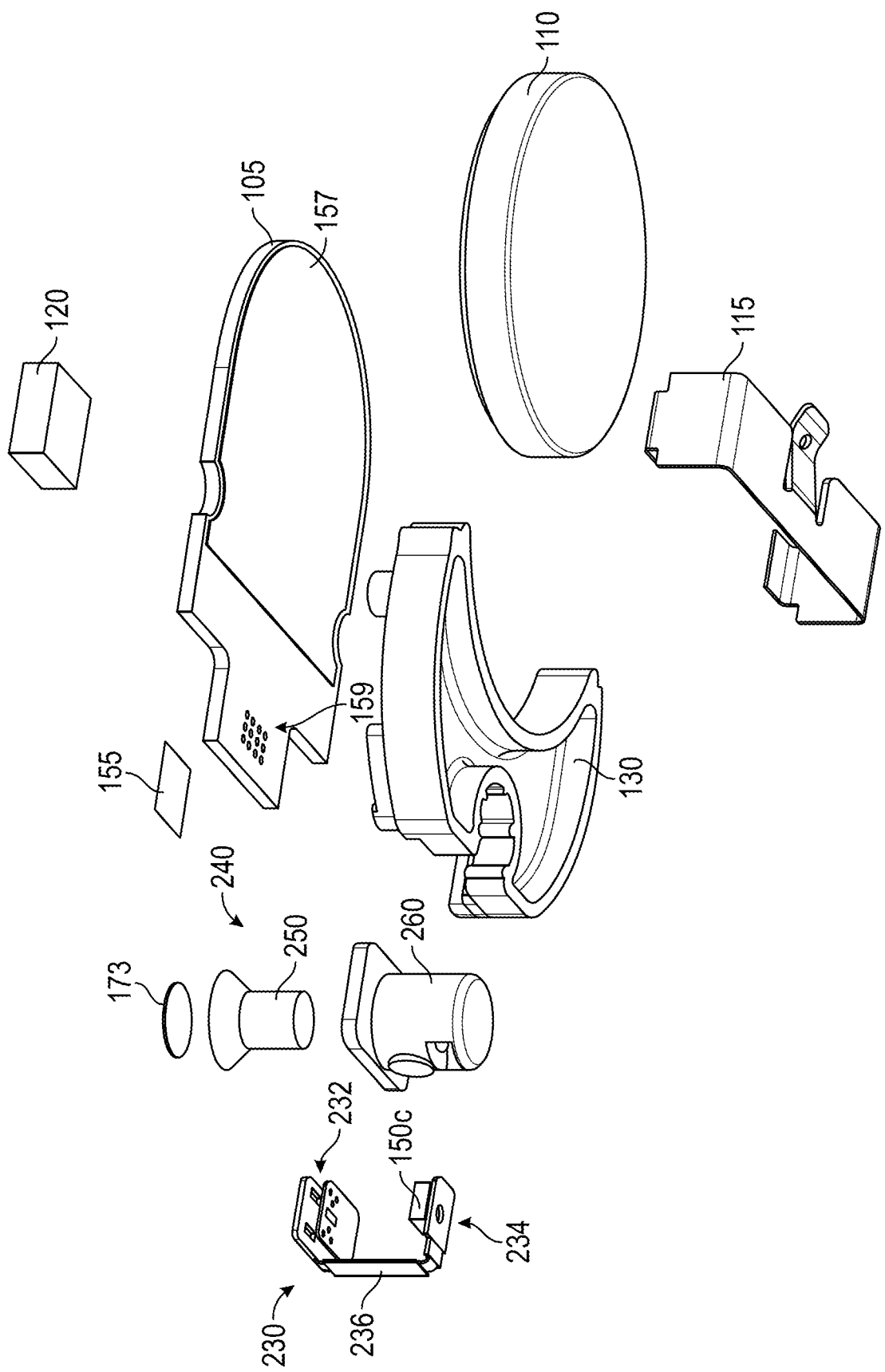

With reference to FIGS. 8C-8D, the temperature sensor 150c can be coupled to the end 234 of the flexible circuit 230 which can be positioned within the opening 266 of the receptacle 260. The insert 250 can be positioned within the cavity 268 of the receptacle 260 such that the end 254 of the insert 250 is positioned proximate or adjacent (for example, above) the temperature sensor 150c. For example, when the insert 250 is positioned within the cavity 268 of the receptacle 260, the end 254 of the insert 250 can contact the temperature sensor 150c. When the probe 240 is secured to the mounting frame 130, for example, via securement of the receptacle 260 within the slot 132 of the mounting frame 130, the probe 240 can transmit thermal energy from a subject in a similar manner as the probe 140 described above. For example, the end 260b of the probe 240 can be positioned adjacent skin of the subject when the wearable device 10 is secured to the subject. Similar to the end 142b of the probe 140, the end 260b can contact (for example, indirectly via substrates 25 and/or 65), apply pressure to, and/or press into the subject skin. Where the wearable device 10 includes one or more of substrates 25 and/or 65, the substrates 25 and/or 65 can be positioned between the end 260b of the probe 240 and the subject's skin when the wearable device 10 is secured to or placed on the subject's skin. The probe 240 or portions thereof (such as the receptacle 260 and/or the insert 250) can comprise thermally conductive material similar to that described with reference to the probe 140. For example, the probe 240 or portions thereof (such as the receptacle 260 and/or the insert 250) can comprise a metallic material, such as aluminum.

Similar to that discussed with reference to probe 140, a portion of the probe 240 (for example, a portion of the receptacle 260) can be positioned through an opening 55 in the substrate 50. The discussion above with reference to the extent to which probe 140 can extend through opening 55 and/or beyond a surface of the substrate 50 is equally applicable to probe 240. In such configuration, when portions of the substrate 25 and/or 65 are secured to the subject's skin around the probe 240, the end 260b can apply pressure to and/or press into a portion of the skin, which can allow the probe 240 to better transmit thermal energy from within the skin. Thermal energy from the skin surface, which can be insulated and/or isolated by one or more of substrates 25, 50, 65 and/or 20, can be transmitted through the end 260b to the temperature sensor 150c positioned within the opening 266. The temperature sensor 150c can determine a body temperature of the subject and/or can generate and transmit one or more signals responsive to the detected thermal energy to the processor 11, for example, via the flexible circuit 230. The thermal energy from the subject's skin surface can also be transmitted from the end 260b through the receptacle 260 and/or insert 250 to the temperature sensor 150a. Such transmitted thermal energy can be transmitted through the thermal paste 173, through the thermally conductive pad 155, and the one or more openings 159 in the circuit board 105 similar to as discussed above with reference to FIG. 5D.

The temperature sensor 150c can be configured to generate one or more signals responsive to detected thermal energy, determined body temperature, and/or transmit such generated one or more signals and/or such determined body temperature to the processor 11 of the wearable device 10 continuously and/or intermittently. For example, temperature sensor 150c can be configured to generate one or more signals responsive to detected thermal energy, determine body temperature, and/or transmit such generated one or more signals and/or such determined temperature every 0.5 seconds, 1 second, 2 second, 3 seconds, 4 seconds, 5 seconds, 10 seconds, 30 seconds, 1 minute, 2 minute, 3 minutes, 4 minutes, 5 minutes, or at other intervals. Such temperature data can be measured and/or transmitted simultaneous of non-simultaneous with temperature data measure and/or transmitted by temperature sensor 150a and/or 150b which is discussed elsewhere herein.

Incorporating both of temperature sensor 150a and 150c can advantageously provide more robust measurements of core body temperature. As shown, temperature sensor 150c can be aligned (for example, vertically aligned with temperature sensor 150a and spaced from temperature sensor 150a along an axis that extends parallel to a height of the probe 240. Similar to temperature sensor 150a, temperature sensor 150c can be spaced away from the temperature sensor 150b. Because the temperature sensor 150c is positioned closer to the subject's skin surface and also closer to the end 260b of the probe than the temperature sensor 150a, the difference or gradient of detected temperature values from sensors 150a, 150c can be used by the processor 11 for purposes of comparison. Additionally, where the wearable device 10 includes all of temperature sensors 150a, 150b, 150c, the processor 11 can determine a core body temperature of the subject based on comparisons of temperature data measured by each of the temperature sensors 150a, 150b, 150c. The processor 11 can apply weight factors to any or all of temperature data received from temperature sensors 150a, 150b, 150c and/or otherwise compare such received data to determine a corrected body temperature.

The various devices, methods, and/or systems discussed above can be used for monitoring a subject's physiological information. For example, as discussed above, the wearable device 10 can be used to measure a subject's temperature, among other things, over time. As discussed above, the wearable device 10 can be configured to wirelessly communicate with (for example, via a wireless transceiver 13 of the wearable device 10) a separate computing device, such as a patient monitor and/or a mobile device (e.g., smart phone). The wearable device 10 can wirelessly transmit physiological data (such as temperature data) over time (continuously or periodically) to such separate computing device for display, among other things. As also discussed above, the wearable device 10 can wirelessly transmit processed or unprocessed obtained physiological information to a mobile phone (for example) which can include one or more hardware processors configured to execute an application that generates a graphical user interface displaying information representative of the processed or unprocessed physiological information obtained from the wearable device 10. Such graphical user interfaces can display continuous and/or periodic measurements obtained from the wearable device 10, display and/or issue various types of alerts, display physiological trend information (for example, temperature trends), among other things. Features or aspects displayed by such graphical user interfaces can include, without limitation, a splash screen, onboarding, device setup, instructions (for example, both visual/graphical and textual) for securing the wearable device 10 to a subject and/or pairing the wearable device 10 to the separate computing device, temperature data and/or trending dashboard, user scenarios, notes (such as medication notes and reminders as well as other user activity notes), temperature trending data and information, user settings and profiles, app settings, and alerts and push notifications.

Any and all of the wearable devices discussed herein can be utilized in systems and/or methods for monitoring and managing health status, exposure levels, and/or risk state of one or more users in relation to a variety of infections or illnesses, such as those described in co-pending U.S. patent application Ser. No. 17/206,794, filed on Mar. 19, 2021, titled "HEALTH MONITORING SYSTEM FOR LIMITING THE SPREAD OF AN INFECTION IN AN ORGANIZATION," which is hereby incorporated by reference in its entirety.

Any and all of the wearable devices discussed herein can be utilized in systems and/or methods for remote patient care and monitoring of one or more users in relation to a variety of infections or illnesses, such as those described in co-pending U.S. patent application Ser. No. 17/207,469, filed on Mar. 19, 2021, titled "REMOTE PATIENT MANAGEMENT AND MONITORING SYSTEMS AND METHODS," which is hereby incorporated by reference in its entirety.

Additional Considerations and Terminology

Although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

Conditional language used herein, such as, among others, "can," "could," "might," "may" "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

Although certain embodiments and examples have been described herein, it will be understood by those skilled in the art that many aspects of the systems and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Any methods disclosed herein need not be performed in the order recited. The methods disclosed herein may include certain actions taken by a practitioner; however, they can also include any third-party instruction of those actions, either expressly or by implication.

The methods and tasks described herein may be performed and fully automated by a computer system. The computer system may in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (for example, not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

Various illustrative logical blocks, modules, routines, and algorithm steps that may be described in connection with the disclosure herein can be implemented as electronic hardware (e.g., ASICs or FPGA devices), computer software that runs on general purpose computer hardware, or combinations of both. Various illustrative components, blocks, and steps may be described herein generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, various illustrative logical blocks and modules that may be described in connection with the disclosure herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. A processor can include an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of any method, process, routine, or algorithm described in connection with the disclosure herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A wearable device configured for noninvasive measurement of a user's body temperature, the wearable device comprising:
    a housing;
    one or more substrates coupled to the housing and configured to be secured to skin of the user;
    a circuit board at least partially enclosed by the housing, said circuit board comprising a first surface, a second surface, and at least one opening extending through a thickness of the circuit board and the first and second surfaces;
    a temperature sensor secured to the circuit board adjacent said first surface and covering a top portion of said at least one opening; and
    a thermally conductive probe comprising a first end and a second end opposite said first end, said first end arranged adjacent said second surface and a bottom portion of said at least one opening, said second end configured to be covered by at least a portion of said one or more substrates and positioned proximate the user's skin when the wearable device is in use, said thermally conductive probe configured to transmit thermal energy from the user's skin towards said temperature sensor via said at least one opening when the wearable device is in use.

2. The wearable device of claim 1, wherein an axis extending through a center of a cross-section of the thermally conductive probe and along a height of the thermally conductive probe is oriented perpendicular with respect to a plane of the circuit board.

3. The wearable device of claim 1, further comprising:
a first thermally conductive material positioned adjacent the first end of the thermally conductive probe, wherein the first thermally conductive material comprises a thermal paste, wherein said thermal paste comprises zinc oxide; and
a second thermally conductive material positioned adjacent the at least one opening and between the thermal paste and the second surface of the circuit board, wherein the second thermally conductive material comprises a metallic material, said metallic material comprising at least one of gold and copper.

4. The wearable device of claim 1, further comprising a mounting frame configured to secure the thermally conductive probe and the circuit board to the housing.

5. The wearable device of claim 4, wherein the mounting frame comprises a slot configured to receive and secure the thermally conductive probe.

6. The wearable device of claim 1, wherein the temperature sensor comprises a thermistor.

7. The wearable device of claim 1, wherein the thermally conductive probe is rigid.

8. The wearable device of claim 5, wherein the slot is configured to surround less than an entire perimeter of a cross-section of the thermally conductive probe.

9. The wearable device of claim 5, wherein the thermally conductive probe comprises a cylindrically-shaped body having a recessed portion spaced from the first and second ends of the thermally conductive probe and arranged within the slot of the mounting frame.

10. The wearable device of claim 1, wherein the at least one opening comprises a plurality of openings spaced from one another.

11. The wearable device of claim 1, wherein the wearable device is configured to wirelessly transmit one or more body temperature values of the user to a separate computing device.

12. The wearable device of claim 1, further comprising a thermally conductive material positioned between the first end of the thermally conductive probe and the second surface of circuit board.

13. The wearable device of claim 12, wherein said thermally conductive material comprises a thermal paste.

14. The wearable device of claim 1, wherein said at least one opening is filled with a thermally conductive material.

15. The wearable device of claim 1, wherein the thermally conductive probe comprises a solid body.

16. A wearable device configured for noninvasive measurement of a user's body temperature, the wearable device comprising:
a housing;
one or more substrates configured to secure the housing to skin of the user;
a circuit board at least partially enclosed by the housing, said circuit board comprising a first surface, a second surface, and at least one opening extending through a thickness of the circuit board and the first and second surfaces;
a temperature sensor mounted to said first surface and covering a top portion of said at least one opening; and
a thermally conductive probe comprising a first end and a second end opposite said first end, said first end arranged proximate said second surface and a bottom portion of said at least one opening, said second end configured to be covered by at least a portion of said one or more substrates and configured to be positioned closer to the user's skin than said first end when the wearable device is in use, said thermally conductive probe configured to transmit thermal energy from the user's skin towards said at least one opening when the wearable device is in use.

17. The wearable device of claim 16, further comprising a thermally conductive material positioned between the first end of the thermally conductive probe and the second surface of circuit board.

18. The wearable device of claim 17, wherein said thermally conductive material comprises a thermal paste.

19. The wearable device of claim 16, wherein said at least one opening is filled with a thermally conductive material.

20. The wearable device of claim 16, wherein the thermally conductive probe comprises a solid body.

* * * * *